United States Patent
Gielen et al.

(10) Patent No.: US 8,293,977 B2
(45) Date of Patent: Oct. 23, 2012

(54) TRANSGENIC PLANTS AND METHODS FOR CONTROLLING BOLTING IN SUGAR BEET

(75) Inventors: Johannes Jacobus Ludgerus Gielen, Bouloc (FR); Petronella Maria Van Roggen, Landskrona (SE); Signe Irene Elisabet Wremert Weich, Landskrona (SE)

(73) Assignee: Syngenta Participations AG, Basel (CH)

( * ) Notice: Subject to any disclaimer, the term of this patent is extended or adjusted under 35 U.S.C. 154(b) by 614 days.

(21) Appl. No.: 12/255,213

(22) Filed: Oct. 21, 2008

(65) Prior Publication Data

US 2009/0162904 A1  Jun. 25, 2009

Related U.S. Application Data

(63) Continuation of application No. 12/297,908, filed as application No. PCT/EP2007/053325 on Apr. 4, 2007.

(30) Foreign Application Priority Data

Apr. 21, 2006  (EP) .................................. 06290670
Jan. 9, 2007  (EP) .................................. 07290025

(51) Int. Cl.
  *A01H 5/00* (2006.01)
(52) U.S. Cl. ..................................... 800/298

(58) Field of Classification Search ........................ None
See application file for complete search history.

(56) References Cited

U.S. PATENT DOCUMENTS

2005/0034194 A1   2/2005   Lee

FOREIGN PATENT DOCUMENTS

WO   WO 00/50615   8/2000

OTHER PUBLICATIONS

Colliver et al (1997, Plant Mol. Biol. 35:509-522).*
Montgomery et al (Trends in Genetics, Jul. 1998, 14(7):255-258).*
Parcy, Flowering: a time for integration, Int. J. Dev. Biol., 49, 585-293 (2005).
Kim et al., The Function of the Flowering Time Gene AGL20 is Conserved in Crucifers, Mol. Cells, 16, 1, 136-141(2003).
Michaels et al., Flowering Locus C Encodes a Novel MADS Domain Protein that Acts as a Repressor of Flowering, The Plant Cell, 11, 949-956 (1999).

\* cited by examiner

*Primary Examiner* — Stuart F. Baum
(74) *Attorney, Agent, or Firm* — Joshua L. Price

(57) ABSTRACT

This invention relates to the field of sugar beet bolting and flowering control, specifically methods and transgenic sugar beet plants for suppressing the vernalization response. In particular, the present invention includes sugar beet plants and methods for modulating sugar beet vernalization by over expression of an FLC gene or by suppressing AGL20 gene expression.

4 Claims, 12 Drawing Sheets

```
                         10              20              30
                          +               +               +
  1  MGRRKIEMKKRIEDKSSRQVTFSKRRSGLIIK  Contig_71
  1  MGRRKIEMKKRIEDKSSRQVTFSKRRSGLIIK  Contig_78
  1  MGRRKIEMKKRIEDKSSRQVTFSKRRSGLIIK  Contig_79

40              50              60
                          +               +               +
 31  KARELSILLCCDVDVAVLVFSNRGRLYEFVNS  Contig_71
 31  KARELSILLCCDVDVAVLVFSNRGRLYEFVNS  Contig_78
 31  KARELSILLCDVDVAVLVFSNRGRLYEFVNS   Contig_79

70              80              90
                          +               +               +
 61  SSLSQITLKRYQDSTAADGKASIAAVET      Contig_71
 61  SSLSQITLKRYQDSTAADGKASIAAVET      Contig_78
 61  SSLSQITLKRYQDSTAADGKASIAAVET      Contig_79

100             110             120
                          +               +               +
 91  -SSPSSCAEVQTCGELVKSVERYLEGPEL     Contig_71
 91  EQSPSSCAEVQTCGGLVKSVERYLEGPEL     Contig_78
 91  EQSPSSCAEVQTCGGLVKSVERYLEGPEL     Contig_79

130             140             150
                          +               +               +
120  ENLRLEDFMRLERQLADALVQTRTRK--      Contig_71
121  ENLRLEDFMRLERQLADALVQTRTRKTQLM    Contig_78
121  ENLRLEDFMRLERQLADALVQTRTRK--      Contig_79

160             170             180
                          +               +               +
146  ---------EKLLKQENEQLKDEVANLIG     Contig_71
151  LSIGTISBQBKLLKQENEQLKDEVANLIG     Contig_78
147  ---------BKLLKQENEQLKDEVANLIG     Contig_79
```

FIG. 8A

```
              190             200            210
              |               |              |
166  I P K S R M H K D L G V N N L M E V D A D R Q Y S Q P L R T  Contig_71
181  I P K S R N H K D L G V N N L M E V D A D R Q Y S Q P L R T  Contig_78
167  I P K S R N H K D L G V N N L M E V D A D R Q Y S Q P L R T  Contig_79

196  L P L L R                                                    Contig_71
211  L P L L R                                                    Contig_78
197  L P L L R                                                    Contig_79
```

FIG. 8B

Degenerate primer HNK5279

```
           1                                                  50
Contig_71  GCNTAYGARC TNTCNGTNCT NTGYGAYGCN GATGTTGCTG TTCTTGTTT
Contig_78  GCNTAYGARC TNTCNGTNCT NTGYGAYGCN GATGTTGCTG TTCTTGTTT
Contig_79  GCNTAYGARC TNTCNGTNCT NTGYGAYGCN GATGTTGCTG TTCTTGTTT 51                                                 100
Contig_71  CTCTAATCGT GGTCGTCTTT ACGAATTCGT CAATAGTTCT TCTTCTTCCA
Contig_78  CTCTAATCGT GGTCGTCTTT ACGAATTCGT CAATAGTTCT TCTTCTTCCA
Contig_79  CTCTAATCGT GGTCGTCTTT ACGAATTCGT CAATAGTTCT TCTTCTTCCA 101                                                150
Contig_71  GTTTGTCTCA GATTCTTAAG CGCTATCAAG ATTCCACTGC AGCAGACGGG
Contig_78  GTTTGTCTCA GATTCTTAAG CGCTATCAAG ATTCCACTGC AGCAGACGGG
Contig_79  GTTTGTCTCA GATTCTTAAG CGCTATCAAG ATTCCACTGC AGCAGACGGG 151                                                200
Contig_71  AAAGCTTCAA TAGCTGCTGT TGAAACAGAG ....AGTTCAC CTTCTAGTTG
Contig_78  AAAGCTTCAA TAGCTGCTGT TGAAACAGAG CAGAGTTCAC CTTCTAGTTG
Contig_79  AAAGCTTCAA TAGCTGCTGT TGAAACAGAG CAGAGTTCAC CTTCTAGTTG 201                                                250
Contig_71  TGCAGAAGTC CAAACATGTG GTGAGCTAGT AAAATCAGTT GAAAGGTACC
Contig_78  TGCAGAAGTC CAAACATGTG GTGAGCTAGT AAAATCAGTT GAAAGGTACC
Contig_79  TGCAGAAGTC CAAACATGTG GTGAGCTAGT AAAATCAGTT GAAAGGTACC 251                                                300
Contig_71  TAGAAGGACC AGAGCTTGAA AATCTTAGGC TTGAGGACTT CATGAGGCTG
Contig_78  TAGAAGGACC AGAGCTTGAA AATCTTAGGC TTGAGGACTT CATGAGGCTG
Contig_79  TAGAAGGACC AGAGCTTGAA AATCTTAGGC TTGAGGACTT CATGAGGCTG 301                                                350
Contig_71  GAGAGGCAAC TAGCTAATGC CCTTGTACAG ACCAGAACCC GAAAG.....
Contig_78  GAGAGGCAAC TAGCTAATGC CCTTGTACAG ACCAGAACCC GAAAGACTCA
Contig_79  GAGAGGCAAC TAGCTAATGC CCTTGTACAG ACCAGAACCC GAAAG.....

351                                                400
Contig_71  .......... .......... .......... .......GAG AAGCTGTTGA
Contig_78  ACTTATGCTA GAATCTATCG GAACACTAAG TGAACAGGAG AAGCTGTTGA
Contig_79  .......... .......... .......... .......GAG AAGCTGTTGA 401                                                450
Contig_71  AACAAGAGAA TGAACAGTTG AAGGATGAGG TAGCAAATCT GATAGGCATT
Contig_78  AACAAGAGAA TGAACAGTTG AAGGATGAGG TAGCAAATCT GATAGGCATT
Contig_79  AACAAGAGAA TGAACAGTTG AAGGATGAGG TAGCAAATCT GATAGGCATT 451                                                500
Contig_71  CCCAAGAGCC GAAACCATAA GGATTTAGGG GTTAACAACT TGATGGAGGT
Contig_78  CCCAAGAGCC GAAACCATAA GGATTTAGGG GTTAACAACT TGATGGAGGT
Contig_79  CCCAAGAGCC GAAACCATAA GGATTTAGGG GTTAACAACT TGATGGAGGT
```

FIG. 9A

```
         501                                                    550
Contig_71 GGATGCTGAT AGACAATACT CTCAGCCACT CAGAACACTT CCACTGCTGA
Contig_78 GGATGCTGAT AGACAATACT CTCAGCCACT CAGAACACTT CCACTGCTGA
Contig_79 GGATGCTGAT AGACAATACT CTCAGCCACT CAGAACACTT CCACTGCTGA 551                                           592
Contig_71 GGTAACTGCT GTAAGAGTCG GCATTGAGCA GCATTTTGSM CT
Contig_78 GGTAACTGCT GTAAGAGTCG GCATTGAGCA GCATTTTGSM CT
Contig_79 GGTAACTGCT GTAAGAGTCG GCATTGAGCA GCATTTTGSM CT
```

TRANSGENIC PLANTS AND METHODS FOR CONTROLLING BOLTING IN SUGAR BEET

FIELD OF THE INVENTION

This invention relates to the field of sugar beet bolting and flowering control, specifically to methods and transgenic sugar beet plants for suppressing the vernalization response.

BACKGROUND OF THE INVENTION

Sugar beet has been cultivated for thousands of years as a sweets source, but its potential as a source of sugar was not discovered until the 18$^{th}$ century. The sugar beet is a biennial plant belonging to the Chenopodiaceae. Its usual life cycle is completed in two years. In the first year a large succulent root is developed, which serves as a reserve for energy in the form of sucrose. For this reason it is farmed as an annual. In the second year it produces flowers and seeds. If there happens to be prolonged cool periods in the first year, the seed stalk can already sprout. This genetically determined thermal induction leads to a phenomenon called bolting. Cropping the beet for sugar extraction cuts the biennial cycle in half, whilst the sucrose is at its peak.

As already mentioned an obligate part of the complete sugar beet life cycle is the cold-induced vernalization, which induces bolting of the plants. The likelihood of bolting is increased in relationship to the number of days on which the maximum temperature does not exceed 12° C. This can lead to loss of yield when the early sowing method is applied, as 1% bolters in a crop have been estimated to reduce sugar yield by 0.4-0.7%.

There exist two methods for cropping sugar beet, spring and autumn cropping, whereas they are practiced in the southern, milder, climate or in northern latitudes respectively. Both rely on varieties with different degrees of bolting resistance. Bolting resistance influences temperature, length and irradiation limits tolerable for seed stalk induction and is a key trait in sugar beet breeding. To allow for complete control of bolting and flowering, by either blocking vernalization, devernalizing vernalized plants or suppressing flower or viable seed production would allow the sugar beet crop to be sown in autumn in northern latitudes without the risk of bolting and flowering in the following season. This shift from a spring into a winter crop would permit growers to drill their crop in autumn and to harvest the next summer. Comparison of winter to spring cultivars in crops like wheat and oilseed rape has shown that winter cultivars consistently yield higher than spring crops. The result would be an improvement of the economic viability and profitability of the crop. A further advantage would be the possibility to combine the growing of spring and winter crops, which would result in an extension of the harvest campaign by starting two to three months earlier, thus allowing for the improved capitalization on investments in equipment and infrastructure necessary for sugar beet harvesting, transport and processing.

In *Arabidopsis thaliana* functional analysis has distinguished four distinct flowering pathways (Levy and Dean, 1998). These four pathways can be assigned to environmental stimuli, such as photoperiodic and vernalization promotion pathways, or inherent developmental signals, e.g. autonomous promotion and floral repression pathways. In some species the timing of flowering is primarily influenced by environmental factors, such as photoperiod, light quality/quantity, vernalization and water or nutrient availability. Other species are influenced less by exogenous signals and rely more on endogenous ones, such as plant size or number of nodes.

One locus of interest is the FLOWERING LOCUS C (FLC) discovered in naturally occurring late-flowering ecotypes of *Arabidopsis* (Koornneef et al, 1994; Lee et al. 1994). FLC is a MADS box transcriptional regulator (Michaels, S D and R M Amasino, 1999) that represses flowering.

In contrast, there are genes that cause the switch from vegetative to reproductive growth, including the "flowering locus T" (FT), "leafy" (LFY), and "suppressor of over expression of constans" referred to as "Agamous-like 20" (AGL20). (Nilsson et al, 1998; Kobayashi et al. 1999; Blazquez et al., 2000; Lee et al, 2000; Samach et al., 2000; Borner et al., 2000) Overexpression of AGL20 causes early flowering in *Arabidopsis*, whereas its down-regulation causes late flowering.

In the case of sugar beet, it has been shown that the vernalization response is one of the most important factors of flower induction. Although bolting resistant varieties are known and available to sugar beet farmers, still there are major problems with the cultivation of the higher yielding winter beet due to bolting incidents. Currently, there are no plants or methods for predictably delaying sugar beet vernalization.

Vernalization and its effect on biennial sugar beet have been described in detail (e.g. Jaggard et al, 1983). Sugar beet responds to temperatures between 3 and 12° C. and cooling degrees accumulate. Several weeks of 3-12° C. are required for the beet to start bolting. The ITB Bolting Model shows that in France, vernalization occurs up to 90 days (13 weeks) after drilling. Seventeen days of 7° C. is the critical number during these 90 days to initiate bolting.

SUMMARY OF THE INVENTION

The present invention includes sugar beet plants and methods for modulating sugar beet vernalization response by over expressing the FLC gene or by suppressing AGL20 gene expression in sugar beet.

In one embodiment, the invention relates to sugar beet plants and methods for modulating sugar beet vernalization response by overexpressing the FLC gene and by suppressing AGL20 gene expression in the same sugar beet plant.

BRIEF DESCRIPTION OF THE FIGURES AND SEQ IDs

FIG. 4 is a table containing the phenotypic results of FLC events.

FIG. 5 is a table containing the phenotypic results of AGL20 events.

FIGS. 8A and 8B depict an alignment of the three protein sequences for the Beta vulgaris FLC gene (BvFLC) that shows the INDELs discriminating between the three different splicing variants.

FIGS. 9A and 9B depict an aliment of the three splicing variants of the putative FLC homologue from sugar beet showing the two in-frame INDELs. The sequence of degenerate primer HiNK5279that was used to amplify these three cDNA fragments is boxed.

Figure 10:
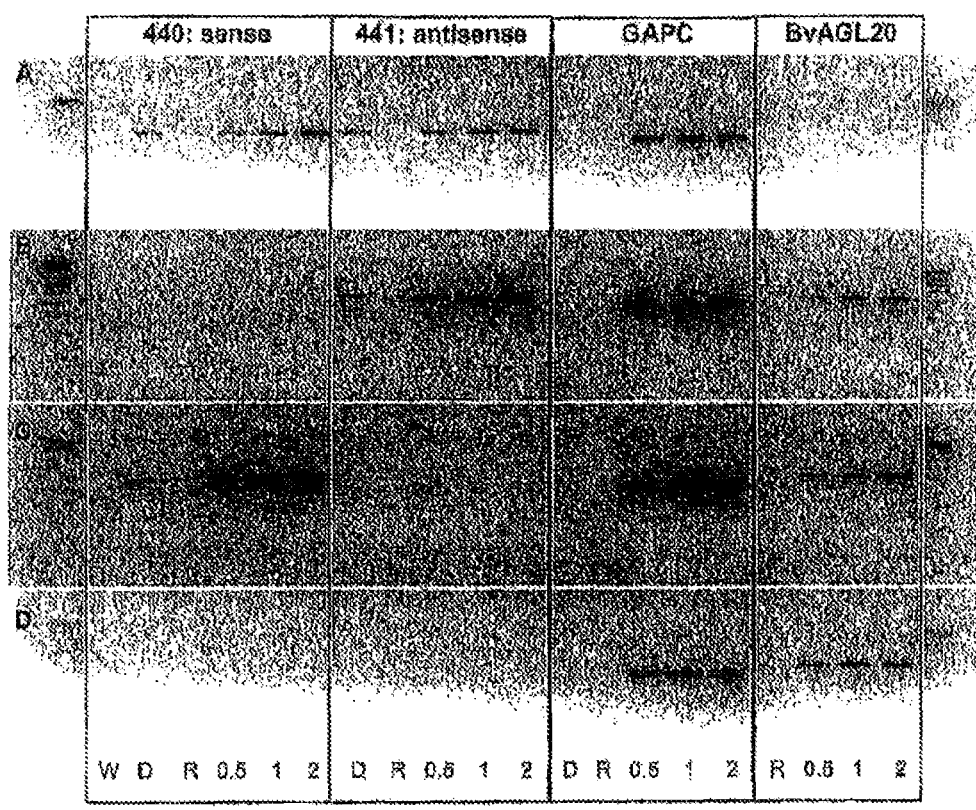

FIG. 10 shows the result of the expression of the RNAi components of pHiNK 440 and 441, control gene GAPC and the endogenous sugar beet gene BvAGL20 by RT-PCR. The endogenous BvAGL20 gene was down regulated in the hybrid (A), but not in the plants, transgene for only one dsRNA component (B and C), nor the NT (D). W=water; D=DNA; R=RNA; 0.5, 1 and 2=amount of cDNA in μl per RT-PCR reaction.

SEQ ID NO: 1 depicts the nucleotide sequence of binary vector pHiNK260 that carries an expression cassette comprising the *Arabidopsis* FLC gene.

SEQ ID NO: 2 depicts the nucleotide sequence of binary vector pHiNK382 that carries an expression cassette comprising an inverted repeat of the sugar beet AGL20 homologue.

SEQ ID NO: 3 depicts the nucleotide sequence of the *Arabidopsis* FLC cDNA (Accession No. AF537203)

SEQ ID NO: 4 depicts the nucleotide sequence of the partial genomic sequence of the sugar beet AGL20 homologue.

SEQ ID NO: 5 depicts the nucleotide sequence of a 0.28 Kb cDNA fragment consisting of exons 3 to 7 of the AGL20 homologue from sugar beet.

SEQ ID NO: 6 depicts the nucleotide sequence of the sugar beet AGL20 homolgue (BvAGL20).

SEQ ID NO: 7 depicts the nucleotide sequence of primer HiNK529.

SEQ ID NO: 8 depicts the nucleotide sequence of primer HiNK792

SEQ ID NO: 9 depicts the nucleotide sequence of primer HiNK793

SEQ ID NO: 10 depicts the nucleotide sequence of primer HiNK794

SEQ ID NO: 11 depicts the nucleotide sequence of primer HiNK795

SEQ ID NO: 12 depicts the nucleotide sequence of primer HiNK796

SEQ ID NO: 13 depicts the nucleotide sequence of primer HiNK624

SEQ ID NO: 14 depicts the nucleotide sequence of primer HiNK619

SEQ ID NO: 15 depicts the nucleotide sequence of primer HiNK725

SEQ ID NO: 16 depicts the nucleotide sequence of primer HiNK729

SEQ ID NO: 17 depicts the nucleotide sequence of primer HiNK2617

SEQ ID NO: 18 depicts the nucleotide sequence of primer HiNK2618

SEQ ID NO: 19 depicts the nucleotide sequence depicts the nucleotide sequence of binary vector pHiNK440 that carries an expression cassette comprising a fragment of the sugar beet AGL20 homologue in sense orientation.

SEQ ID NO: 20 depicts the nucleotide sequence depicts the nucleotide sequence of binary vector pHiNK441 that carries an expression cassette comprising a fragment of the sugar beet AGL20 homologue in antisense orientation.

SEQ ID NO: 21 depicts the nucleotide sequence of contig__71+EST identifying the coding region of splicing variant 1 of the endogenous sugar beet FLC gene.

SEQ ID NO: 22 depicts the amino acid sequence of the expression product of the coding region of splicing variant 1 of the endogenous sugar beet FLC gene.

SEQ ID NO: 23 depicts the nucleotide sequence of contig__78+EST identifying the coding region of splicing variant 2 of the endogenous sugar beet FLC gene.

SEQ ID NO: 24 depicts the amino acid sequence of the expression product of the coding region of splicing variant 2 of the endogenous sugar beet FLC gene SEQ ID NO: 25 depicts the nucleotide sequence of contig__79+EST identifying the coding region of splicing variant 3 of the endogenous sugar beet FLC gene.

SEQ ID NO: 26 depicts the amino acid sequence of the expression product of the coding region of splicing variant 3 of the endogenous sugar beet FLC gene.

SEQ ID NO: 27 depicts the nucleotide sequence of contig__71+EST

SEQ ID NO: 28 depicts the nucleotide sequence of contig__78+EST

SEQ ID NO: 29 depicts the nucleotide sequence of contig__79+EST

SEQ ID NO: 30 depicts the nucleotide sequence of primer HiNK5277

SEQ ID NO: 31 depicts the nucleotide sequence of primer HiNK5279

SEQ ID NO: 32 depicts the nucleotide sequence of primer AGL20 A

SEQ ID NO: 33 depicts the nucleotide sequence of primer AGL20 B

SEQ ID NO: 34 depicts the nucleotide sequence of primer HiNK023

SEQ ID NO: 35 depicts the nucleotide sequence of primer gapCex5/6F

SEQ ID NO: 36 depicts the nucleotide sequence of primer gapCex8R

SEQ ID NO: 37 depicts the nucleotide sequence of primer HiNK HiNK 819

DEFINITIONS

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

"Sugar beet" refers to all species and subspecies within the genus *Beta* as well as all kinds of cultivated beets of *Beta vulgaris*. Cultivated beets have been separated into four groups: leaf beet, garden beet, fodder beet and sugar beet. "Sugar beet" refers also to all cultivated beets including those grown for other purposes than the production of sugar, such as ethanol, plastics or other industrial products. In particular, "Sugar beet" refers to fodder beet and sugar beet, but especially to sugar beet.

"Bolting" refers to the transition from the vegetative rosette stage to the inflorescence or reproductive growth stage.

"Vernalization" refers to the process by which floral induction in some plants is promoted by exposing the plants to chilling for a certain duration.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The term "heterologous" when used in reference to a gene or nucleic acid refers to a gene encoding a factor that is not in its natural environment (i.e., has been altered by the hand of man). For example, a heterologous gene may include a gene from one species introduced into another species. A heterologous gene may also include a gene native to an organism that has been altered in some way (e.g., mutated, added in multiple copies, linked to a non-native promoter or enhancer sequence, etc.). Heterologous genes further may comprise plant gene sequences that comprise cDNA forms of a plant gene; the cDNA sequences may be expressed in either a sense (to produce mRNA) or anti-sense orientation (to produce an antisense RNA transcript that is complementary to the mRNA transcript). In one aspect of the invention, heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

"Inverted repeat" refers to a nucleotide sequence found at two sites on the same nucleic acid sequence, but in opposite orientation.

"Expression cassette" as used herein means a nucleic acid molecule capable of directing expression of a particular nucleotide sequence or sequences in an appropriate host cell, comprising a promoter operably linked to the nucleotide sequence or sequences of interest which is/are operably linked to termination signals. It also typically comprises sequences required for proper translation of the nucleotide sequence(s). The expression cassette may also comprise sequences not necessary in the direct expression of a nucleotide sequence of interest but which are present due to convenient restriction sites for removal of the cassette from an expression vector. The expression cassette comprising the nucleotide sequence(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence(s) in the expression cassette may be under the control of a constitutive promoter or of an inducible promoter that initiates transcription only when the host cell is exposed to some particular stimulus, which may be an external stimulus or an internal stimulus being provided from the host itself. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

"Operably-linked" refers to the association of nucleic acid sequences on a single nucleic acid fragment so that the function of one affects the function of the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Primers" as used herein are isolated nucleic acids that are capable of becoming annealed to a complimentary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods.

"Suppression" refers to the absence or observable decrease in the level of protein and/or mRNA product from a target gene. In particular, "suppression" refers to a decrease in the level of protein and/or mRNA product from a target gene in the range of between 20% and 100%, particularly of between 40% and 80%, more particularly of between 50% and 90%, even more particularly of between 60% and 95%, but especially of between 75% and 98% and up to 100%. The consequences of inhibition can be confirmed by examination of the outward properties of the cell or organism or by biochemical and gene expression detection techniques known to those skilled in the art. For example, suppression of the AGL20 gene expression is indicated by an absence or delay of the vernalization response in a growing sugar beet plant.

Substantially identical or homologous in the context of two nucleic acid or protein sequences, refers to two or more sequences or subsequences that have at least 60%, preferably 80%, more preferably 90%, even more preferably 95%, and most preferably at least 99% nucleotide or amino acid residue identity, when compared and aligned for maximum correspondence, as measured using one of the following sequence comparison algorithms or by visual inspection. In particular, the substantial identity exists over a region of the sequences that is at least about 50 residues in length, more particularly over a region of at least about 100 residues, and especially the sequences are substantially identical over at least about 150 residues. In a specific embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman (1981), by the homology alignment algorithm of Needleman & Wunsch (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra). One example of an algorithm that is suitable for determining percent sequence identity and sequence similarity is the BLAST algorithm, which is described in Altschul et al. (1990).

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993).

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refers to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another sugar beet line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected.

A "transgene" refers to a gene introduced into the genome of an organism by genetic manipulation in order to alter its genotype.

A "transgenic plant" is a plant having one or more plant cells that contain an expression vector.

The term "Messenger RNA (mRNA) refers to the RNA that is without introns and that can be translated into protein by the cell.

"cDNA" refers to a single- or a double-stranded DNA that is complementary to and derived from mRNA.

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process.

"Overexpression" refers to the level of expression in transgenic cells or organisms that exceeds levels of expression in normal or untransformed (nontransgenic) cells or organisms.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes. Gene silencing includes virus-induced gene silencing.

"RNA interference" (RNAi) refers to the process of sequence-specific post-transcriptional gene silencing in plants and animals mediated by short interfering RNAs (siRNAs). Various terms such as siRNA, target RNA molecule, dicer or ribonuclease III enzyme are concepts known to those skilled in the art and full descriptions of these terms and other concepts pertinent to RNAi can be found in the literature. For reference, several terms pertinent to RNAi are defined below. However, it is understood that any particular hypothesis describing the mechanisms of RNAi are not necessary to practice the present invention.

The term "siRNAs" refers to short interfering RNAs. In some embodiments, siRNAs comprise a duplex, or double-stranded region, of about 21-23 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of a siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such RNA target molecules include unprocessed mRNA, ribosomal RNA, and viral RNA genomes.

"RNA-inducing silencing complex" (RISC) mediates cleavage of single-stranded RNA having sequence complementary to the antisense strands of siRNA duplex. Cleavage of the target RNA takes place in the middle of the region of complementary to the antisense strand of the siRNA duplex (Elbashier et al. 2001).

The term "sufficient complementary" means that a first or a second strand sequence of RNA introduced into a plant cell is capable of hybridizing or annealing sufficiently to the RNA produced by a target gene (mRNA) under conditions found in the cytoplasm of said plant cell, such that suppression of the expression of the target gene is triggered. For example, the strand of the first or second strand sequence of RNA that binds to the mRNA produced by the target gene is at least 50% identical to the corresponding mRNA sequence of the target gene, more desirably at least 70% identical, yet more desirable is at least 90% identity and even more desirable is at least 95% identical.

It is to be understood that the percentage of identity between the strand of the first or second strand sequence of RNA and the mRNA produced by the target gene, which is in the range of between at least 70% identity and at least 95% identity, can be any numerical value within this range.

DETAILED DESCRIPTION OF THE INVENTION

The present invention includes transgenic sugar beet plants and methods for modulating sugar beet vernalization response by over expressing an FLC gene and/or by suppressing AGL20 gene expression in sugar beet.

One embodiment of the invention includes constitutively expressing an FLC gene resulting in modulation of bolting resistance in sugar beet. According to the present invention, transgenic sugar beet plants overexpressing a FLC gene no longer respond to a typical vernalization period of 18 weeks by bolting and subsequent flowering, but to the contrary continue vegetative growth (non-bolting) and develop a normal taproot.

The invention includes a transgenic sugar beet plant comprising in its genome the coding region of a heterologous FLC gene, wherein expression of the FLC gene causes overexpression of the FLC gene product thereby suppressing the vernalization response of the sugar beet plant. A gene is considered to be overexpressed if the expression rate is above the basic level of expression normally found in the native, untransformed sugar beet plant. In particular, overexpression refers to an expression rate which exceeds the basic level of expression normally found in the native, untransformed sugar beet plant by at least 10%, particularly by at least 20%, more particularly by at least 30%, even more particularly by at least 40%, but especially by at least 50% to 100% or higher.

In a specific embodiment of the invention, a sugar beet plant is provided wherein said heterologous FLC gene comprises the heterologous FLC coding region consisting of the FLC cDNA depicted under Accession No. AF537203 (http://ftp.dna.affrc.go.jp-/pub/dna_all/A/F5/37/20/AF537203/AF537203), particularly under the control of a heterologous constitutive promoter causing overexpression of the FLC gene product thereby suppressing the vernalization response of the sugar beet plant.

The present invention also includes a transgenic sugar beet plant comprising a heterologous FLC gene as depicted by SEQ ID NO: 3, wherein expression of the FLC gene causes overexpression of the FLC gene product thereby suppressing the vernalization response of the sugar beet plant.

The present invention also includes a transgenic sugar beet plant comprising an endogenous FLC gene as depicted in SEQ ID NOs: 27, 28 and 29 or the encoding part thereof, particularly under the control of a heterologous constitutive promoter causing overexpression of the endogenous gene product thereby suppressing the vernalization response of the sugar beet plant.

The present invention also includes a transgenic sugar beet plant comprising an endogenous FLC gene as depicted in SEQ ID NOs: 21, 23 and 25 or the encoding part thereof, particularly under the control of a heterologous constitutive promoter causing overexpression of the endogenous gene product thereby suppressing the vernalization response of the sugar beet plant.

The invention also includes a transgenic sugar beet plant comprising a heterologous FLC gene that has at least 99%, 98%, 97%, 96%, 95%, 94% or 93% sequence identity with the nucleotide sequence of the FLC cDNA depicted under Accession No. AF537203, particularly under the control of a heterologous constitutive promoter causing overexpression of the FLC gene product thereby suppressing the vernalization response of the sugar beet plant.

In a specific embodiment, a heterologous FLC gene is provided that has at least 99%, 98%, 97%, 96%, 95%, 94% or 93% sequence identity with the nucleotide sequence of the FLC cDNA as depicted by SEQ ID NO: 3, wherein expression of the FLC gene causes overexpression of the FLC gene product thereby suppressing the vernalization response of the sugar beet plant.

The invention also includes a transgenic sugar beet plant comprising an endogenous FLC gene that has at least 99%, 98%, 97%, 96%, 95%, 94% or 93% sequence identity with the nucleotide sequence depicted in SEQ ID NOs: 27, 28 and 29 or the encoding part thereof, which encoding part may be under the control of a heterologous constitutive promoter, wherein expression of the FLC gene causes overexpression of the FLC gene product thereby suppressing the vernalization response of the sugar beet plant.

The invention also includes a transgenic sugar beet plant comprising an endogenous FLC gene that has at least 99%, 98%, 97%, 96%, 95%, 94% or 93% sequence identity with the nucleotide sequence depicted in SEQ ID NOs: 21, 23 and 25 or the encoding part thereof, which encoding part may be under the control of a heterologous constitutive promoter, wherein expression of the FLC gene causes overexpression of the FLC gene product thereby suppressing the vernalization response of the sugar beet plant.

The invention also includes a seed of the transgenic sugar beet plant comprising a heterologous FLC gene comprising a coding region consisting of the FLC cDNA depicted under Accession No. AF537203, particularly under the control of a heterologous constitutive promoter causing overexpression of the FLC gene product thereby suppressing the vernalization response of the sugar beet plant.

In a specific embodiment, a heterologous FLC gene is provided as depicted by SEQ ID NO: 3, wherein expression of the FLC gene in a plant grown form said seed causes overexpression of the FLC gene product thereby suppressing the vernalization response of the sugar beet plant.

The invention also includes a seed of the transgenic sugar beet plant comprising an endogenous FLC gene as depicted in SEQ ID NOs: 27, 28 and 29 or the encoding part thereof, particularly the encoding part of an endogenous FLC gene under the control of a heterologous constitutive promoter, wherein expression of the FLC gene in a plant grown form said seed causes overexpression of the FLC gene product thereby suppressing the vernalization response of the sugar beet plant.

The invention also includes a seed of the transgenic sugar beet plant comprising an endogenous FLC gene as depicted in SEQ ID NOs: 21, 23 and 25 or the encoding part thereof, particularly the encoding part of an endogenous FLC gene under the control of a heterologous constitutive promoter, wherein expression of the FLC gene in a plant grown form said seed causes overexpression of the FLC gene product thereby suppressing the vernalization response of the sugar beet plant.

The invention also includes a seed of a transgenic sugar beet plant, wherein the seed comprises a heterologous FLC gene that has at least 99%, 98%, 97%, 96%, 95%, 94% or 93% sequence identity with the nucleotide sequence of the FLC cDNA depicted under Accession No. AF537203, particularly under the control of a heterologous constitutive promoter causing overexpression of the FLC gene product thereby suppressing the vernalization response of the sugar beet plant.

In a specific embodiment, a heterologous FLC gene is provided that has at least 99%, 98%, 97%, 96%, 95%, 94% or 93% sequence identity with the nucleotide sequence of the FLC cDNA as depicted by SEQ ID NO: 3, wherein expression of the FLC gene in a plant grown form said seed causes overexpression of the FLC gene product thereby suppressing the vernalization response of the sugar beet plant.

The invention also includes a seed of a transgenic sugar beet plant, wherein the seed comprises an endogenous FLC gene that has at least 99%, 98%, 97%, 96%, 95%, 94% or 93% sequence identity with the nucleotide sequence depicted in SEQ ID NOs: 27, 28 and 29 or with the encoding part thereof, which encoding part may be under the control of a heterologous constitutive promoter, wherein expression of the FLC gene in a plant grown form said seed causes overexpression of the FLC gene product thereby suppressing the vernalization response of the sugar beet plant.

The invention also includes a seed of a transgenic sugar beet plant, wherein the seed comprises an endogenous FLC gene that has at least 99%, 98%, 97%, 96%, 95%, 94% or 93% sequence identity with the nucleotide sequence depicted in SEQ ID NOs: 21, 23 and 25 or with the encoding part thereof, which encoding part may be under the control of a heterologous constitutive promoter, wherein expression of the FLC gene in a plant grown form said seed causes overexpression of the FLC gene product thereby suppressing the vernalization response of the sugar beet plant.

One embodiment of the invention includes a transgenic sugar beet plant according to the invention comprising a heterologous FLC gene as disclosed herein before incorporated in an expression cassette, particularly an expression cassette depicted by nucleotide sequence 786-2817 of SEQ ID NO: 1.

One embodiment of the invention includes a transgenic sugar beet plant according to the invention comprising a heterologous FLC gene as disclosed herein before incorporated in an expression cassette, particularly an expression cassette depicted by nucleotide sequence 786-2817 of SEQ ID NO: 1, wherein the expression cassette comprises a constitutive promoter.

One embodiment of the invention includes a transgenic sugar beet plant according to the invention comprising a heterologous FLC gene as disclosed herein before incorporated in an expression cassette, particularly an expression cassette depicted by nucleotide sequence 786-2817 of SEQ ID NO: 1, wherein the expression cassette comprises a CaMV35S promoter.

In another specific embodiment, the invention relates to a transgenic sugar beet plant comprising a heterologous FLC gene as disclosed herein before, particularly incorporated in an expression cassette under the control of a constitutive promoter, particularly the constitutive CaMV 35S promoter and a terminator, particularly the mannopine synthase (mas) terminator from *Agrobacterium tumefaciens*.

In one embodiment, the invention relates to a transgenic sugar beet plant comprising an expression cassette comprising a coding region of an endogenous FLC gene, particularly an FLC gene as depicted in SEQ ID NOs: 27, 28 and 29.

In one embodiment, the invention relates to a transgenic sugar beet plant comprising an expression cassette comprising a coding region of an endogenous FLC gene, particularly an FLC gene as depicted in SEQ ID NOs: 21, 23 and 25.

In a specific embodiment, said coding region of the endogenous FLC gene is under the control of a constitutive promoter, particularly under the control of a constitutive CaMV 35S promoter, but especially under the control of the constitutive CaMV 35S promoter and a terminator, particularly the mannopine synthase (mas) terminator from *Agrobacterium tumefaciens*.

Another embodiment of the invention is a method of producing a transgenic sugar beet plant according to the invention comprising:

transforming a sugar beet plant cell with a transgene comprising regulatory sequences operably linked to a heterologous or an endogenous plant FLC gene coding region;

identifying a sugar beet plant cell carrying the inserted transgene; and regenerating a transgenic plant from the plant cell identified in b).

The present invention further includes producing biofuels, such as ethanol, butanol, methanol, biogas and diesel derived from a transgenic sugar beet plant according to the invention and as described herein before comprising in its genome the coding region of a heterologous or of an endogenous FLC gene, wherein expression of said FLC gene causes over expression of the FLC gene product thereby suppressing the vernalization response of said sugar beet plant.

The present invention further includes producing other industrial applications such as plastics derived from a transgenic sugar beet plant according to the invention and as described herein before comprising in its genome the coding region of a heterologous or of an endogenous FLC gene, wherein expression of said FLC gene causes over expression of the FLC gene product thereby suppressing the vernalization response of said sugar beet plant.

The present invention also includes a method of suppressing the expression of an endogenous AGL20 gene of a sugar beet plant cell, comprising introducing into said plant cell a first RNA strand and a second RNA strand, wherein said first RNA strand or, in the alternative, said second strand is sufficiently complimentary to at least a portion of an RNA strand of said endogenous AGL20 gene to hybridize or anneal to the RNA produced by the AGL20 gene such as to cause suppression of the expression of the endogenous AGL20 gene and said first RNA strand and said second RNA strand form a double stranded RNA, wherein said double stranded RNA participates in RNA interference of expression of said endogenous AGL20 gene.

One embodiment of the invention includes a method of suppressing the expression of an endogenous AGL20 gene of a sugar beet plant cell comprising introducing into said plant cell a first RNA strand and a second RNA strand, wherein introducing into said plant cell a first RNA strand and a second RNA strand comprises transforming said cell with an heterologous DNA, which when transcribed in the plant cell, yields a nucleotide sequence corresponding to said first RNA strand and a nucleotide sequence corresponding to said second RNA strand.

In another embodiment of the invention said heterologous DNA includes an inverted repeat, which when transcribed, yields a nucleotide sequence corresponding to said first RNA strand and a nucleotide sequence corresponding to said second RNA strand.

In a specific embodiment, the invention relates to a method of suppressing the expression of an endogenous AGL20 gene according to the invention and as described herein before, wherein said first RNA strand has a degree of complimentarity to a portion of RNA of a sugar beet AGL20 gene fragment approximately 0.6 Kb in size obtainable from sugar beet cDNA obtained from total RNA extracted from sugar beet leaves in a reverse trascriptase reaction using pimer 5'-CCRATGAACARTTS-NGTCTCNACWTC-3' (SEQ ID NO: 14), which cDNA is used as a template in a PCR reaction employing a degenerate forward primer with the nucleotide sequence 5'-ATGGTKMGRGGNAARACNCAGATGA-3' (SEQ ID NO: 13), which shares sequence homology to the extreme NH2-terminus starting at the ATG codon and spanning codons 1 to 9; and a degenerate reverse primer with the nucleotide sequence 5'-CCRATGAACARTTSNGTCTC-NACWTC-3' (SEQ ID NO: 14), which is complementary to the COOH-terminus, hybridizing just upstream of the stop codon at exon 8, such as to allow said first RNA strand to hybridize or anneal to the RNA strand of said AGL20 gene fragment resulting in the suppression of the expression of the endogenous AGL20 gene.

Yet another embodiment of the invention includes the method of suppressing the expression of an endogenous AGL20 gene as described herein before, wherein said first RNA strand is sufficiently complimentary to a portion of RNA of the sugar beet AGL20 gene fragment depicted in SEQ ID NO: 6 to hybridize or anneal to the RNA produced by the AGL20 gene such as to cause suppression of the expression of the endogeous AGL20 gene.

This suppression of the AGL20 gene leads to a delay of the vernalization response in a growing sugar beet plant or causes the sugar beet plant to develop a non-bolting phenotype, which means that the sugar beet plant does no longer respond to a typical vernalization period of 18 weeks by bolting and subsequent flowering, but to the contrary continue vegetative growth (non-bolting) and develop a normal taproot.

Plants expressing said delayed vernalisation response or said non-bolting phenotype can be easily identified and selected by applying a phenotypic analysis experiment employing standardized growth conditions.

The invention also includes the method of suppressing the expression of an endogenous AGL20 gene as described herein before, wherein said first RNA strand comprises a sequence fragment about 21 to about 23 nucleotides in length that is sufficiently complementary to a portion of RNA of said sugar beet AGL20 gene such as to cause suppression of the expression of the endogeous AGL20 gene.

The invention includes the method of suppressing the expression of an endogenous AGL20 gene as described herein before, wherein said first RNA strand comprises a sequence fragment about 21 to about 25 nucleotides in length that is sufficiently complementary to a portion of RNA of said sugar beet AGL20 gene such as to cause suppression of the expression of the endogeous AGL20 gene.

The invention further includes the method of suppressing the expression of an endogenous AGL20 gene according to the invention, wherein said first RNA strand comprises a sequence fragment about 21 to about 30 nucleotides in length that is sufficiently complementary to a portion of RNA of said sugar beet AGL20 gene such as to cause suppression of the expression of the endogeous AGL20 gene.

One embodiment of the invention further includes the method of suppressing the expression of an endogenous AGL20 gene according to the invention, wherein said first RNA strand comprises a sequence fragment about 18 to about 23 nucleotides in length that is sufficiently complementary to a portion of RNA of said sugar beet AGL20 gene to result in the suppression of the expression of the endogenous AGL20 gene.

One embodiment of the invention further includes the method of suppressing the expression of an endogenous AGL20 gene according to the invention, wherein said first RNA strand comprises a sequence fragment about 18 through 25 nucleotides in length that is sufficiently complementary to a portion of RNA of said sugar beet AGL20 gene to result in the suppression of the expression of the endogenous AGL20 gene.

One embodiment of the invention further includes the method of suppressing the expression of an endogenous AGL20 gene according to the invention, wherein said first RNA strand comprises a sequence fragment about 18 through 30 nucleotides in length that is sufficiently to a portion of RNA of said sugar beet AGL20 gene to result in the suppression of the expression of the endogeous AGL20 gene.

In one embodiment, the invention relates to a method of suppressing expression of an AGL20 gene according to the invention and as described herein before, wherein the heterologous DNA that transcribes said first RNA strand is obtainable from a 0.28 Kb cDNA fragment consisting of exons 3 to 7 of the AGL20 gene fragment approximately 0.6 Kb in size obtainable from sugar beet cDNA obtained from total RNA extracted from sugar beet leaves in a reverse trascriptase reaction using pimer 5'-CCRATGAACARTTSNGTCTC-NACWTC-3' (SEQ ID NO: 14), which cDNA is used as a template in a PCR reaction employing a degenerate forward primer with the nucleotide sequence 5'-ATGGTKMGRG-GNAARACNCAGATGA-3' (SEQ ID NO: 13), which shares sequence homology to the extreme NH2-terminus starting at the ATG codon and spanning codons 1 to 9; and a degenerate reverse primer with the nucleotide sequence 5'-CCRAT-GAACARTTSNGTCTCNACWTC-3' (SEQ ID NO: 14), which is complementary to the COOH-terminus, hybridizing just upstream of the stop codon at exon 8, in a PCR reaction using a forward primer with the nucleotide sequence 5'-CTAT GGATCCGCATGCTG ATCTCCTGATC-3' (SEQ ID NO: 8) and a reverse primer with the nucleotide sequence 5'-GAAGCAGAAACTTACCT AAGAAGTTAAAAAGTCT-CGA-AC-3' (SEQ ID NO: 9).

One embodiment of the invention further includes the method of suppressing expression of an AGL20 gene, wherein the heterologous DNA that transcribes said first RNA strand is depicted by SEQ ID NO: 5.

In one aspect, the invention relates to an expression cassette comprising a heterologous DNA comprising a first RNA strand and a second RNA strand, wherein said first RNA strand has a degree of complemantarity to at least a portion of an RNA strand of an endogenous AGL20 gene which allows said first RNA strand to hybridize or anneal to the RNA strand of said endogenous AGL20 gene and wherein said first RNA strand and said second RNA strand form a double stranded RNA such that upon expression in a plant suppression of the endogenous AGL20 gene is caused.

In a specific embodiment of the invention, an expression cassette is provided comprising an inverted repeat, which, when transcribed in the sugar beet cell, forms a double stranded RNA molecule in said plant cell comprising said first and second RNA strands.

In another specific embodiment of the invention, an expression cassette is provided, wherein said inverted repeat is operatively linked to a constitutive promoter, particularly a CaMV promoter.

In one embodiment, the invention relates to an expression cassette as described herein before comprising a heterologous DNA that transcribes said first RNA strand, which heterologous DNA is obtainable from a 0.28 Kb cDNA fragment consisting of exons 3 to 7 of an AGL20 gene fragment approximately 0.6 Kb in size obtainable from sugar beet cDNA obtained from total RNA extracted from sugar beet leaves in a reverse trascriptase reaction using pimer 5'-CCRATGAACARTTSNGTCTCNACWTC-3' (SEQ ID NO: 14), which cDNA is used as a template in a PCR reaction employing a degenerate forward primer with the nucleotide sequence 5'-ATGGTKMGRGGNAARA-CNCAGATGA-3' (SEQ ID NO: 13), which shares sequence homology to the extreme NH2-terminus starting at the ATG codon and spanning codons 1 to 9; and a degenerate reverse primer with the nucleotide sequence 5'-CCRATGAACARTTSNGTCTCN-ACWTC-3' (SEQ ID NO: 14), which is complementary to the COOH-terminus, hybridizing just upstream of the stop codon at exon 8, in a PCR reaction using a forward primer with the nucleotide sequence 5'-CTATGGATCCGCATGCTG ATCTCCTGATC-3' and a reverse primer with the nucleotide sequence 5'-GAAGCAGAAACTTACCT/ AAGA AGT-TAAAAAGTCTCGAAC-3'.

In another specific embodiment of the invention the expression cassette comprises a heterologous DNA as depicted by SEQ ID NO: 5.

In one embodiment an expression cassette according to the invention and as described herein above comprises an inverted repeat, which, when transcribed in the sugar beet cell, forms a double stranded RNA molecule in said plant cell comprising said first and second RNA strands.

In a specific embodiment, said inverted repeat is operatively linked to a constitutive promoter, particularly a CaMV promoter.

In one embodiment, the invention relates to an expression cassette as described herein before, wherein said heterolgous DNA is inserted between a promoter and terminator which heterologous DNA is obtainable by
  a) amplifying a 0.28 Kb cDNA fragment consisting of exons 3 to 7 of the 0.6 Kb AGL20 gene fragment according to the invention and as described herein before, in a recombinant PCR reaction using a forward primer with the nucleotide sequence 5'-CTAT GGATCCGCATGCTG ATCTCCTGATC-3' (SEQ ID NO: 8) and a reverse primer with the nucleotide sequence 5'- AAACTTACCTAAGA AGTTAAAAAG-TCTCGAAC-3' (SEQ ID NO: 9);
  b) amplifying a 0.19 Kb fragment comprising the ST-LS1 intron and flanking splicing sites using forward primer 5'-ATCCAACCGCGGACCTGCACATC-AACAA-3' (SEQ ID NO: 7) and reverse primer 5'- GTTCGAGACTTTT TA- ACTTCTTT AGGTAAGTTTCT-GCTTCTAC-3' (SEQ ID NO: 12);
  c) fusing the amplification products obtained in steps a) and b) to each other by means of a second round of PCR using primers of SEQ ID NO:8 and SEQ ID NO:7 and using a mix of both amplification products as template, yielding a fusion product of 0.47 Kb in length;
  d) amplifying the 0.28 Kb BvAGL20 fragment a second time, using forward primer 5'-TAAA TCCGCGGAAGAAGTTAAAAAGTCTCGAAC-3' (SEQ ID NO: 10) and reverse primer 5'-CTATTT GTCGACGCATGCTGATCTCCT-GATC-3' (SEQ ID NO: 11) that differ from the primer used in step a) with respect to their linkers;
  e) fusing both fragments at the Sac II restriction sites to create an inverted repeat for the BvAGL20 sequence separated by the intron from the potato ST-LS1 gene.

In a specific embodiment, an expression cassette is provided as depicted by the nucleotide sequence 233-2657 of SEQ ID NO: 2.

One embodiment of the invention further includes the method of suppressing the expression of an endogenous AGL20 gene according to the invention, wherein introducing said first and second RNA strands is by insertion of an expression cassette according to the invention and as described herein before comprising said heterologous DNA into the genome of said plant cell.

One embodiment of the invention further includes the method of suppressing the expression of an endogenous AGL20 gene according to the invention, wherein said expression cassette is depicted by the nucleotide sequence 233-2657 of SEQ ID NO: 2.

One embodiment of the invention further includes the method of suppressing the expression of an endogenous AGL20 gene according to the invention, wherein introducing said first and second RNA strands is by insertion of said strands into the plant cell by injection.

One embodiment of the invention further includes the method of suppressing the expression of an endogenous AGL20 gene according to the invention, further comprising introducing into the genome of the plant an expression cassette that includes an inverted repeat, which when transcribed, forms a double stranded RNA molecule in said plant cell comprising said first and second RNA strands.

One embodiment of the invention further includes the method of suppressing the expression of an endogenous AGL20 gene according to the invention, wherein said first RNA sequence is sufficiently complementary to an RNA sequence of the nucleic acid sequence depicted by SEQ ID NO: 6.

The invention further includes the method of suppressing the expression of an endogenous AGL20 gene according to the invention, wherein said inverted repeat is operatively linked to a constitutive promoter.

The invention includes the method of suppressing the expression of an endogenous AGL20 gene according to the invention, further comprising an intron located between said first and second RNA strands.

The invention also includes the method of suppressing the expression of an endogenous AGL20 gene according to the invention, wherein said intron is depicted by the nucleotide sequence depicted by 817-1009 of SEQ ID NO: 2.

The invention includes a transgenic sugar beet cell, particularly a transgenic sugar beet plant, comprising a heterologous gene construct, said construct comprising a heterologous DNA, which when transcribed in the sugar beet cell, yields a first RNA nucleotide sequence and a second RNA nucleotide sequence, wherein said first RNA nucleotide sequence is sufficiently complimentary to at least a portion of a RNA strand of said endogenous AGL20 gene to hybridize or anneal to the RNA produced by the AGL20 gene such as to cause suppression of the expression of the endogeous AGL20 gene and said first RNA nucleotide sequence and said second RNA nucleotide sequence form a double stranded RNA, wherein the double stranded RNA participate in RNA interference of expression of said endogenous AGL20 gene.

In one embodiment, a transgenic sugar beet cell is provided, particularly a transgenic sugar beet plant, wherein the heterologous DNA is obtainable from a 0.28 Kb cDNA fragment consisting of exons 3 to 7 of the AGL20 gene fragment according to the invention and as described herein before, in a PCR reaction using a forward primer with the nucleotide sequence 5'-CTATGGATCCGCATGCTG ATCTCCT-GATC-3' (SEQ ID NO: 8) and a reverse primer with the nucleotide sequence 5'- GAAGCAG AAACT TACCT AAGA AGT TAAAAAGTCTCGAAC-3' (SEQ ID NO: 9).

In a specific embodiment the transgenic sugar beet cell, particularly the transgenic sugar beet plant, according to the invention comprises a heterologous gene construct, wherein the heterologous DNA is depicted by SEQ ID NO: 5.

In still another specific embodiment the transgenic sugar beet cell, particularly the transgenic sugar beet plant, according to the invention comprises a heterologous gene construct, wherein said gene construct includes an inverted repeat, which when transcribed, forms a double stranded RNA molecule in said plant cell comprising said first and second RNA strands, wherein said double stranded RNA molecule triggers AGL20 gene silencing.

In a specific embodiment of the invention, a transgenic sugar beet cell is provided, particularly a transgenic sugar beet plant, comprising a heterolgous DNA inserted between a promoter and terminator, which heterologous DNA is obtainable by a. amplifying a 0.28 Kb cDNA fragment consisting of exons 3 to 7 of the 0.6 Kb AGL20 gene fragment according to the invention and as described herein before, in a recombinant PCR reaction using a forward primer with the nucleotide sequence 5'-CTAT GGATCCGCATGCTG ATCTCCTGATC-3' (SEQ ID NO: 8) and a reverse primer with the nucleotide sequence 5'- GAAGCAG AAACTTA CCT AAGA AGT TAAAAAGTCTCGAAC-3' (SEQ ID NO: 9);

b. amplifying a 0.19 Kb fragment comprising the ST-LS1 intron and flanking splicing sites using forward primer 5'-ATCCAACCGCGGACCTGCACATC-AACAA-3' (SEQ ID NO: 7) and reverse primer 5'-GTTCGAG ACTTT TTA ACTTGTT AGGTAAGTTTCTGCT-TCTAC-3' (SEQ ID NO: 12);

c. fusing the amplification products obtained in steps a) and b) to each other by means of a second round of PCR using primers of SEQ ID NO:8 and SEQ ID NO:7 and using a mix of both amplification products as template, yielding a fusion product of 0.47 Kb in length;

d. amplifying the 0.28 Kb BvAGL20 fragment a second time, using forward primer 5'-TAAA TCCGCGGAAGAAGTTAAAAAGTCTCGAAC-3' (SEQ ID NO: 10) and reverse primer 5'-CTATTT GTCGACGCATGCTGATCTCCT-GATC-3' (SEQ ID NO: 11) that differ from the primer used in step a) with respect to their linkers;

e. fusing both fragments at the Sac II restriction sites to create an inverted repeat for the BvAGL20 sequence separated by the intron from the potato ST-LS1 gene.

In another specific embodiment the transgenic sugar beet cell, particularly the transgenic sugar beet plant, according to the invention comprises a heterologous gene construct, wherein said gene construct comprises an expression cassette depicted by nucleotide sequence 233-2657 of SEQ ID NO: 2.

In another specific embodiment of the invention, a transgenic sugar beet cell, particularly a transgenic sugar beet plant, is provided comprising an expression cassette according to the invention and as described herein before.

In one embodiment, the invention relates to a method of producing a transgenic sugar beet plant according to the invention and as described herein before comprising:

a. transforming a sugar beet cell with an expression cassette according to the invention and as described herein before;

b. identifying a sugar beet cell containing the heterologous DNA, c. regenerating a transgenic plant from said plant cell identified in step b)

d. identifying a sugar beet plant exhibiting a delay of the vernalization response or a complete suppression of the vernalization response resulting in a non bolting (NB) phenotype, e. optionally confirming the presence of the heterologous DNA in the plant cell genome introduced in step a)

The invention also includes a method of suppressing the expression of an AGL20 gene in a sugar beet plant cell, comprising introducing into the plant cell a first RNA fragment that is sufficiently identical or complementary to a portion of the AGL20 gene, a second RNA fragment that is sufficiently complementary to the first RNA fragment, to result in the suppression of the expression of the endogeous AGL20 gene, wherein the first and second RNA fragments form a double stranded RNA molecule in the plant cell, wherein the double stranded RNA molecule suppresses by siRNA mediated silencing the expression of the AGL20 gene.

The invention also includes a method of suppressing the expression of an endogenous AGL20 gene in a sugar beet plant, comprising:
a) introducing into a sugar beet plant cell a first RNA strand;
b) growing said plant cell into a first plant;
c) introducing into a second sugar beet plant cell a second RNA strand, wherein said first RNA strand is sufficiently complimentary to at least a portion of a RNA strand of said endogenous AGL20 gene to hybridize or anneal to the RNA produced by the AGL20 gene such as to cause suppression of the expression of the endogenous AGL20 gene and said first RNA strand and said second RNA strand are capable of forming a double stranded RNA;
d) growing said second sugar beet plant cell into a second plant;
e) crossing said first plant with said second plant to produce seed; and
f) growing a plant from said seed, wherein said first and second RNA strands form double stranded RNA which participates in RNA interference of expression of said endogenous AGL20 gene.

In a specific aspect, the invention relates to a transgenic sugar beet cell, particularly a transgenic sugar beet plant, comprising in its genome
i. a first heterologous gene construct comprising the coding region of a heterologous or of an endogenous FLC gene, and
ii. a second heterologous gene construct capable of encoding a RNA composition, said construct comprising a heterologous DNA, which when transcribed, yields a first RNA nucleotide sequence and a second RNA nucleotide sequence, wherein said first RNA nucleotide sequence is sufficiently complimentary to at least a portion of a RNA strand of said endogenous AGL20 gene to hybridize or anneal to the RNA produced by the AGL20 gene and said first RNA nucleotide sequence and said second RNA nucleotide sequence form a double stranded RNA, wherein the double stranded RNA participate in RNA interference of expression of said endogenous AGL20 gene.

In one embodiment of the invention, a transgenic sugar beet cell, particularly a transgenic sugar beet plant, is provided, wherein said first heterologous gene construct comprises the FLC coding region consisting of the FLC cDNA of Accession No. AF537203.

In a specific embodiment of the invention said FLC gene is depicted by SEQ ID NO: 3.

In another embodiment of the invention, a transgenic sugar beet cell, particularly a transgenic sugar beet plant, is provided, wherein said FLC gene comprises the FLC coding region which has at least 99%, 98%, 97%, 96%, 95%, 94% or 93% sequence identity with the nucleotide sequence of the FLC cDNA of Accession No. AF537203.

In a specific embodiment of the invention said FLC gene has at least between 93% and 99% sequence identity with the nucleotide sequence depicted by SEQ ID NO: 3.

In another specific embodiment, said FLC gene comprises the FLC coding region of an endogenous FLC gene as depicted in SEQ ID NOs: 21, 23 and 25.

In still another specific embodiment, said FLC gene comprises an FLC coding region which has at least 99%, 98%, 97%, 96%, 95%, 94% or 93% sequence identity with the nucleotide sequence the FLC coding region of an endogenous FLC gene as depicted in SEQ ID NOs: 21, 23 and 25.

In one embodiment, the invention relates to a transgenic sugar beet cell, particularly a transgenic sugar beet plant, according to the invention and as described herein before, wherein said heterologous DNA comprised in the second gene construct is obtainable from a 0.28 Kb cDNA fragment consisting of exons 3 to 7 of the AGL20 gene fragment according to the invention and as described herein before, in a PCR reaction using a forward primer with the nucleotide sequence 5'-CTATGGATCC-GCATGCTG ATCTCCT-GATC-3' (SEQ ID NO: 8) and a reverse primer with the nucleotide sequence 5'- GAAGCAGAAACTT ACCTAAGA AGT-TAAAAAGTCTCGAAC-3' (SEQ ID NO: 9).

In one embodiment, the invention relates to a transgenic sugar beet cell, particularly a transgenic sugar beet according to the invention and as described herein before, wherein the heterologous DNA that transcribes said first RNA strand is depicted by SEQ ID NO: 5.

In one embodiment, the invention relates to a transgenic sugar beet cell or plant according to the invention and as described herein before, wherein said heterologous DNA comprised in the second gene construct includes an inverted repeat, which when transcribed, forms a double stranded RNA molecule in said plant cell comprising said first and second RNA strands, wherein said double stranded RNA molecule triggers AGL20 gene silencing.

In one embodiment, the invention relates to a transgenic sugar beet cell or plant according to the invention and as described herein before, comprising in the second gene construct a heterologous DNA inserted between a promoter and terminator, which heterologous DNA is obtainable by
a. amplifying a 0.28 Kb cDNA fragment consisting of exons 3 to 7 of the 0.6 Kb AGL20 gene fragment according to the invention and as described herein before, in a recombinant PCR reaction using a forward primer with the nucleotide sequence 5'-CTAT GGATCCGCATGCTG ATCTCCTGATC-3' (SEQ ID NO: 8) and a reverse primer with the nucleotide sequence 5'- AACTTACCTAAGA AGT-TAAAAAGTCTCGAAC-3' (SEQ ID NO: 9);
b. amplifying a 0.19 Kb fragment comprising the ST-LS1 intron and flanking splicing sites using forward primer 5'-ATCCAACCGCGGACCT-GCACATCAACAA-3' (SEQ ID NO: 7) and reverse primer 5'-GTTC- GAGACTT TTTAAG AGGTAAGTTTCTGCTTC-TAC-3' (SEQ ID NO: 12);
c. fusing the amplification products obtained in steps a) and b) to each other by means of a second round of PCR using primers of SEQ ID NO:8 and SEQ ID NO:7 and using a mix of both amplification products as template, yielding a fusion product of 0.47 Kb in length;
d. amplifying the 0.28 Kb BvAGL20 fragment a second time, using forward primer 5'-TAAA TCCGCGGAAGAAGTTAAAAAGTCTCGAAC-3' (SEQ ID NO: 10) and reverse primer 5'-CTATTT GTCGACGCATGCTGATCTCCT-GATC-3' (SEQ ID NO: 11) that differ from the primer used in step a) with respect to their linkers;
e. fusing both fragments at the Sac II restriction sites to create an inverted repeat for the BvAGL20 sequence separated by the intron from the potato ST-LS1 gene.

In one embodiment, the invention relates to transgenic sugar beet cell or plant according to the invention and as described herein before wherein said heterologous DNA comprised in the second gene construct is depicted by nucleotide sequence 233-2657 of SEQ ID NO: 2.

In one embodiment of the invention, a transgenic sugar beet cell, particularly a transgenic sugar beet plant, is provided, wherein said second heterologous gene construct is comprised in an expression cassette according to the invention and as described herein before.

In a specific aspect, the invention relates to a transgenic sugar beet plant as described herein before, wherein co-expression of the first and second heterologous gene construct leads to a synergistic delay of the vernalization response in said sugar beet plant.

In one embodiment, in invention thus relates to a transgenic sugar beet cell, particularly a transgenic sugar beet plant comprising the AGL20 and the FLC expression product in a synergistically effective amount.

In another specific aspect, the invention relates to a transgenic sugar beet plant as described herein before, wherein co-expression of the first and second heterologous gene construct leads to a complete suppression of the vernalization response in said sugar beet plant resulting in a non-bolting (NB) phenotype.

In still another specific aspect, the invention relates to a transgenic sugar beet plant as described herein before which plant is obtainable by a cross of two parent plants wherein the first heterologous gene construct is contributed by parent 1 and the second heterologous gene construct is contributed by parent 2, wherein at least one of the parent plants does not exhibit a non bolting (NB) phenotype.

In one embodiment, the invention relates to a method of producing a transgenic sugar beet plant according to the invention comprising:
  a. transforming a sugar beet cell with an expression cassette comprising a heterologous FLC gene wherein said FLC gene is operably linked to regulatory sequences and/or an expression cassette according to the invention and as described herein before comprising a heterologous gene construct capable of suppressing expression of an endogenous AGL20 gene;
  b. identifying a sugar beet cell containing the heterologous DNA,
  c. optionally transforming the sugar beet cell identified in step b) with an expression cassette comprising a heterologous FLC gene wherein said FLC gene is operably linked to regulatory sequences or with an expression cassette according to the invention and as described herein before comprising a heterologous gene construct capable of suppressing expression of an endogenous AGL20 gene and identifying a sugar beet cell containing both the introduced heterologous DNAs;
  d. regenerating a transgenic plant from said plant cell identified in step b)
  e. identifying a sugar beet plant exhibiting a delay of the vernalization response or a complete suppression of the vernalization response resulting in a non bolting (NB) phenotype,
  f. optionally confirming the presence of the heterologous DNAs in the plant cell genome introduced in step a) and, optionally, step c).

In a specific embodiment, the method of producing a transgenic sugar beet plant comprises crossing of two parent plants wherein the first heterologous gene construct is contributed by parent 1 represented by a sugar beet plant comprising a FLC gene according to the invention and as described herein before and the second heterologous gene construct is contributed by parent 2 represented by a sugar beet plant comprising a heterologous gene construct capable of suppressing expression of an endogenous AGL20 gene according to the invention and as described herein before; and to the plant resulting from said cross, particularly a plant that contains the gene construct contributed by both parent 1 and parent 2, more particularly a plant that contains the gene construct contributed by both parent 1 and parent 2 and exhibits the delayed vernalization response or non-bolting phenotype.

In a specific embodiment, the invention relates to a method of producing a transgenic sugar beet plant, wherein at least one of the parent plants does not exhibit a non bolting (NB) phenotype.

The present invention includes a root of the transgenic sugar beet plant according to the invention and as described herein before, wherein the root is derived from a plant derived from a transgenic sugar beet cell comprising
  a) a heterologous gene construct, said construct comprising a heterologous DNA, which when transcribed in the sugar beet cell, yields a first RNA nucleotide sequence and a second RNA nucleotide sequence, wherein said first RNA nucleotide sequence is sufficiently complimentary to at least a portion of a RNA strand of said endogenous AGL20 gene to hybridize or anneal to the RNA produced by the AGL20 gene such as to cause suppression of the expression of the endogenous AGL20 gene and said first RNA nucleotide sequence and said second RNA nucleotide sequence form a double stranded RNA, wherein the double stranded RNA participate in RNA interference of expression of said endogenous AGL20 gene
  b) a heterologous gene construct, said construct comprising a heterologous or an endogenous FLC gene
  c) a combination of a) and b).

The present invention includes a plant derived from a transgenic sugar beet cell according to the invention and as described herein before comprising a heterologous gene construct, said construct comprising
  a) a heterologous DNA, which when transcribed in the sugar beet cell, yields a first RNA nucleotide sequence and a second RNA nucleotide sequence, wherein said first RNA nucleotide sequence is sufficiently complimentary to at least a portion of a RNA strand of said endogenous AGL20 gene to hybridize or anneal to the RNA produced by the AGL20 gene such as to cause suppression of the expression of the endogenous AGL20 gene and said first RNA nucleotide sequence and said second RNA nucleotide sequence form a double stranded RNA, wherein the double stranded RNA participate in RNA interference of expression of said endogenous AGL20 gene.
  b) a heterologous gene construct, said construct comprising a heterologous or an endogenous FLC gene
  c) a combination of a) and b).

The present invention also includes a progeny plant derived from a transgenic sugar beet plant according to the invention and as described herein before comprising a heterologous gene construct, said construct
  a) heterologous DNA, which when transcribed in the sugar beet cell, yields a first RNA nucleotide sequence and a second RNA nucleotide sequence, wherein said first RNA nucleotide sequence is sufficiently complimentary to at least a portion of a RNA strand of said endogenous AGL20 gene to hybridize or anneal to the RNA produced by the AGL20 gene such as to cause suppression of the expression of the endogenous AGL20 gene and said first RNA nucleotide sequence and said second RNA nucleotide sequence form a double stranded RNA, wherein the double stranded RNA participate in RNA interference of expression of said endogenous AGL20 gene.

b) a heterologous gene construct, said construct comprising a heterologous or an endogenous FLC gene c) a combination of a) and b).

The present invention includes sugar derived from the transgenic sugar beet root comprising heterologous gene construct, said construct comprising a) heterologous DNA, which when transcribed in the sugar beet cell, yields a first RNA nucleotide sequence and a second RNA nucleotide sequence, wherein said first RNA nucleotide sequence is sufficiently complimentary to at least a portion of a RNA strand of said endogenous AGL20 gene to hybridize or anneal to the RNA produced by the AGL20 gene such as to cause suppression of the expression of the endogeous AGL20 gene and said first RNA nucleotide sequence and said second RNA nucleotide sequence form a double stranded RNA, wherein the double stranded RNA participate in RNA interference of expression of said endogenous AGL20 gene.

b) a heterologous gene construct, said construct comprising a heterologous or an endogenous FLC gene c) a combination of a) and b).

The present invention includes biofuels such as ethanol, butanol, methanol, biogas and diesel derived from the transgenic sugar beet root comprising heterologous gene construct, said construct comprising a) heterologous DNA, which when transcribed in the sugar beet cell, yields a first RNA nucleotide sequence and a second RNA nucleotide sequence, wherein said first RNA nucleotide sequence is sufficiently complimentary to at least a portion of a RNA strand of said endogenous AGL20 gene to hybridize or anneal to the RNA produced by the AGL20 gene such as to cause suppression of the expression of the endogeous AGL20 gene and said first RNA nucleotide sequence and said second RNA nucleotide sequence form a double stranded RNA, wherein the double stranded RNA participate in RNA interference of expression of said endogenous AGL20 gene.

b) a heterologous gene construct, said construct comprising a heterologous or an endogenous FLC gene c) a combination of a) and b).

The present invention includes other industrial applications such as plastics derived from the transgenic sugar beet root comprising heterologous gene construct, said construct comprising a) heterologous DNA, which when transcribed in the sugar beet cell, yields a first RNA nucleotide sequence and a second RNA nucleotide sequence, wherein said first RNA nucleotide sequence is sufficiently complimentary to at least a portion of a RNA strand of said endogenous AGL20 gene to hybridize or anneal to the RNA produced by the AGL20 gene such as to cause suppression of the expression of the endogeous AGL20 gene and said first RNA nucleotide sequence and said second RNA nucleotide sequence form a double stranded RNA, wherein the double stranded RNA participate in RNA interference of expression of said endogenous AGL20 gene.

b) a heterologous gene construct, said construct comprising a heterologous or an endogenous FLC gene c) a combination of a) and b).

The present invention also includes a method of producing sugar, ethanol, biogas and/or diesel fuel comprising processing a sugar beet plant according to any of the preceding claims and deriving sugar from the sugar beet plant comprising a heterologous gene construct, said construct comprising a) heterologous DNA, which when transcribed in the sugar beet cell, yields a first RNA nucleotide sequence and a second RNA nucleotide sequence, wherein said first RNA nucleotide sequence is sufficiently complimentary to at least a portion of a RNA strand of said endogenous AGL20 gene to hybridize or anneal to the RNA produced by the AGL20 gene such as to cause suppression of the expression of the endogeous AGL20 gene and said first RNA nucleotide sequence and said second RNA nucleotide sequence form a double stranded RNA, wherein the double stranded RNA participate in RNA interference of expression of said endogenous AGL20 gene.

b) a heterologous gene construct, said construct comprising a heterologous or an endogenous FLC gene c) a combination of a) and b).

The present invention is further directed to novel compositions and methods relating to RNA interference (RNAi). The compositions include dsRNA containing RNA strands that are sufficiently complementary or identical to a target mRNA, such as AGL20 mRNA. As currently understood, the dsRNA are processed by Dicer by cutting the dsRNA into short interfering RNA (siRNA). According to one embodiment of the present invention, novel siRNA compositions are incorporated into the RISC complex for RNA interference of a target gene mRNA, such as the sugar beet AGL20 gene mRNA. Interfering with sugar beet AGL20 gene mRNA expression results in suppression or delay of the sugar beet vernalization response. A delay in the vernalization response results in the sugar beet plant continuing its vegetative growth and to develop a normal taproot.

In one embodiment of the invention, the siRNA includes a first RNA strand that is between 21 and 23 nucleotides in length and a second RNA strand that hybridizes to the first sequence under biological conditions, such as those conditions found in the cell, particularly in the cytoplasm and/or the nucleus of the cell.

In yet another embodiment of the invention, the siRNA includes a first RNA strand that is between 19 and 30 nucleotides in length and a second RNA strand that hybridizes to the first sequence under biological conditions, such as those conditions found cell, particularly in the cytoplasm and/or the nucleus of the cell.

The invention includes siRNAs of any length, provided that the novel siRNA play a role in triggering RNA interference of a target gene mRNA, such as the sugar beet AGL20 gene mRNA.

In another embodiment of the invention, the siRNA first or second strands are sufficiently complementary or identical to a nucleotide sequence of RNA produced by the AGL20 gene to trigger RNA silencing. The term "sufficient complementary" means that the first or second strand sequences of the siRNA are capable of hybridizing or annealing sufficiently to the RNA produced by the target gene (mRNA) under conditions found in the cytoplasm, such that RNAi is triggered which leads to a suppression of the expression of the target gene. This suppression of the AGL20 gene causes the sugar beet plant to develop a non-bolting phenotype which means that the sugar beet plant does no longer respond to a typical vernalization period of 18 weeks by bolting and subsequent flowering, but to the contrary continue vegetative growth (non-bolting) and develop a normal taproot.

Plants expressing said non-bolting phenotype can be easily identified and selected by applying a phenotypic analysis experiment employing standardized growth conditions.

In one embodiment, a siRNA molecule of the invention includes a nucleic acid strand that is sufficiently complementary or identical to at least a portion of the AGL20 gene. It is known that if the siRNA strand is identical, the target mRNA is cut into useless RNA fragments. However, if the pairing is less than identical, the RISC complex binds to the mRNA and is capable of blocking ribosome movement along the native mRNA, but is not capable of cutting the mRNA into small fragments. Nevertheless, in either case, expression of the gene from which the mRNA is transcribed, is silenced—no AGL20 protein is formed. The present invention, therefore, further includes one strand of the siRNA that is sufficiently complementary or identical to a corresponding sequence of the mRNA transcribed from the gene whose expression is altered. For example, the strand of the siRNA that binds to the mRNA is at least 50% identical to the corresponding mRNA sequence of the target gene, more desirably at least 70% identical, yet more desirable is at least 90% identity and even more desirable is at least 95% identical.

It is to be understood that the percentage of identity between the one strand of the siRNA that is sufficiently complementary or identical to a corresponding sequence of the mRNA transcribed from the gene whose expression is altered and the mRNA produced by the target gene, which is in the range of between at least 70% identity and at least 95% identity, can be any numerical value within this range.

It is known that RNA sequences with insertions, deletions, and single point mutations relative to the target sequence are also effective for target gene expression suppression. Sequence identity between the siRNA molecule and the target gene transcription product (for example, the target gene mRNA) may be optimized by alignment algorithms known in the art and calculating the percent similarity between the nucleotide sequences. Alternatively, the siRNA molecule of the present invention may be identified not by its sequence similarity to the target molecule, but by its capability to hybridize to and silence expression of the target sequence.

According to another embodiment of the present invention, novel siRNA compositions can be used by RNA dependent RNA polymerase (RdRp) to make a new dsRNA, which can then be processed to form more siRNA.

Yet another embodiment of the invention occurs when the single stranded siRNA compositions of the invention not associated with RISC bind to their corresponding mRNA, for example AGL20 transcribed mRNA, wherein RNA dependent RNA polymerase serves as a primer to produce dsRNA.

In yet another embodiment of the invention, a method of gene silencing includes separately introducing into a plant cell a sense RNA fragment of a target gene, such as AGL20, and an antisense RNA fragment of the same gene, wherein the sense RNA fragment and the antisense RNA are capable of forming a double-stranded RNA molecule, wherein the expression of the target gene in the cell is altered. In a preferred embodiment, the RNA fragments are comprised in two different RNA molecules. In another preferred embodiment, the RNA fragments are mixed before being introduced into the cell under conditions allowing them to form a double-stranded RNA molecule. In another preferred embodiment, the RNA fragments are introduced into said cell sequentially. In yet another embodiment, the RNA fragments are comprised in one RNA molecule. In such case, the RNA molecule is preferably capable of folding such that said RNA fragments comprised therein form a double stranded RNA molecule.

Various methods of using sense and antisense RNA fragments to silence a target gene are described in WO99/61631.

The present invention further provides for a method of introducing into a plant cell a dsRNA molecule comprises of sense and antisense fragments of a target gene mRNA.

It is understood, however, that the underlying mechanics of RNAi silencing may not be entirely understood, and thus the present invention is not to be bound to any particular RNAi silencing theory. Thus, in the context of the present invention, the term "siRNA mediated silencing" is not restricted to a particular RNA interference cellular mechanism.

EXAMPLES

Example 1

Figure 1:
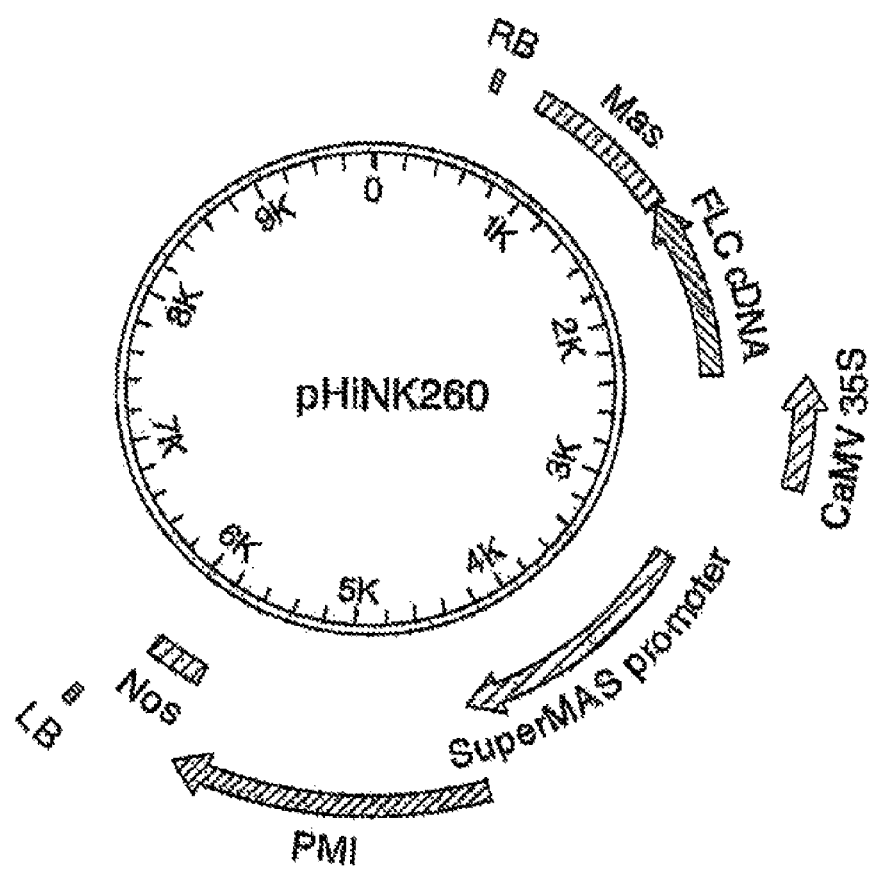
FIG. 1 is a plasmid map of binary vector pHiNK260.

Assembly of the Binary Transformation Vector for the Constitutive Expression of FLC in Transgenic Sugar Beet The FLC gene cassette is under the control of the constitutive CaMV 35S promoter. The FLC coding region consists of the FLC cDNA from *Arabidopsis thaliana* (Accession No. AF537203, SEQ ID NO: 3) followed by the mannopine synthase (mas) terminator from *Agrobacterium tumefaciens*. The gene cassette was introduced as a 2.4 Kb Asc I-Pac I fragment on the T-DNA of the proprietary binary transformation vector pVictorHiNK carrying the SuperMAS::PMI::NOS selectable marker gene for mannose selection in sugar beet (Joersbo et al, 1998), yielding binary vector pHiNK260 (FIG. 1). The complete nucleotide sequence of pHiNK260 is disclosed in SEQ. 1. Upon completion, binary vector pHiNK260 was transformed into *Agrobacterium tumefaciens* strain EHA101 (Hood et al., 1986) by means of a heatshock as described in Holsters et al., 1978.

Example 2

Amplification and Cloning of Homologues from Sugar Beet *Beta vulgaris*

2.1 Amplification and Cloning of the Putative FLC Homologue from Sugar Beet

In order to amplify and clone the FLC homologue from sugar beet, degenerate primers were designed against the conserved MADS_MEF2-like domain that is present at the NH2 terminus of all Type 2 members of the MADS box family of transcription factors to which FLC belongs (Pařenicová et al, 2003). Degenerate primer HiNK5277 (5'-CGNCG-NAAYGGNCTNCTNAARAARGC-3', SEQ ID NO: 30) targets the conserved amino acid sequence motif "RRNGLLKKA"; primer HiNK5279 (5'-GCNTAYGARCT-NTCNGTNCTNTGYGAYGCNGA-3', SEQ ID NO:31) hybridizes immediately downstream of HiNK5277 and targets amino acid sequence motif "AYELSVLCDAE".

Total RNA was extracted from sugar beet leaves and apices using the RNeasy Plant Mini kit from Qiagen and converted into cDNA using the FirstChoice RLM-RACE kit from Ambion, Inc. Experimental conditions were essentially as described by the 3' RLM-RACE protocol supplied with the kit using the 3' RACE adapter as primer in the reverse transcriptase reaction. The putative FLC homologue was subsequently amplified starting from the cDNA reaction as initial template in two successive rounds of PCR using the 3' RACE Outer Primer in combination with degenerate primer HiNK5277 followed by the combination of the 3' RACE Inner Primer with degenerate primer HiNK5279 in typical PCR reactions. The thus obtained amplification fragment measured approximately 0.6 Kb in size as expected according to the sequence of the FLC homologues from *Brassica* species. However, the obtained DNA band is expected to contain multiple sequences due to the degenerate nature of primers HiNK5277 and HiNK5279 that in principle will allow for the amplification of multiple members of the MADS box family of transcription factors. The PCR products were excised, purified, cloned and subsequently submitted for sequence analysis. Amongst the various sequences obtained that, as expected all share part of the MADS box motif, three highly homologous sequences were identified as putative homologues of FLC, referred to as contig__71, __78 and __79. These three cDNA fragments differ from each other by small in-frame deletions which suggest that they represent alternative splicing variants of one and the same gene (Fig. X). At the 5' end all three cDNA fragments show extensive sequence homology to a public sugar beet EST with accession number BQ595637. Combining the EST sequence with the three cDNA fragments allowed for the reconstitution of the full-length cDNAs transcribed from the putative FLC homologue (SEQ ID NO 21, 23 and 25) and the corresponding translation products (SEQ ID NO 22, 24 and 26). The alignment of three putative FLC proteins is shown in FIG. 9.

2.2 Amplification and Cloning of the AGL20 Homologue from Sugar Beet

Figure 2:
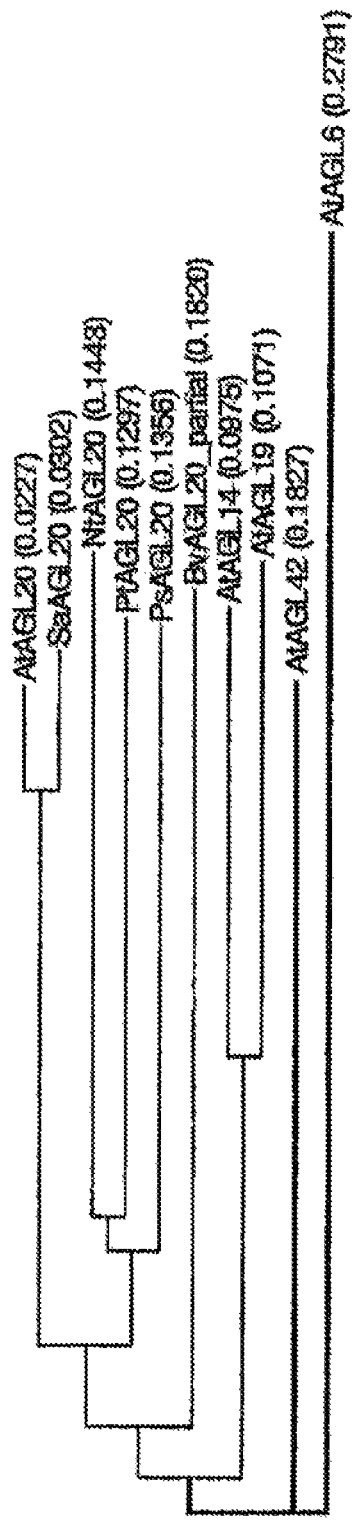
FIG. 2 is a phylogenetic tree inferred from the alignment of the coding region of the AGL20 homologue from sugar beet to the AGL20 homologues from *Arabidopsis thaliana, Pinus taeda, Pisum sativum, Sinapsis alba* and *Nicotiana tabacum*.

In order to amplify and clone the AGL20 homologue from sugar beet, degenerate primers were designed against the conserved nucleotide sequences when aligning the AGL20 cDNA from *Arabidopsis* to the AGL20 homologues from mustard and tobacco (FIG. 2). Since AGL20 belongs to the large family of MADS box transcription factors, the primers were designed to regions conserved between the various AGL20 homologues, but distinct to most of the other MADS box family members. Primer HiNK624 (5'-ATGGTK-MGRGGNAARACNCAGATGA-3', SEQ ID NO: 13), shares sequence homology to the extreme NH2-terminus starting at the ATG codon and spanning codons 1 to 9; primer HiNK619 (5'-CCRATGAACARTTSNGTCTCNACWTC-3', SEQ ID NO: 14), is complementary to the COOH-terminus, hybridizing just upstream of the stop codon at exon 8, spanning codons 198 to 206 according to the AGL20 sequence from *Arabidopsis*.

Figure 3:
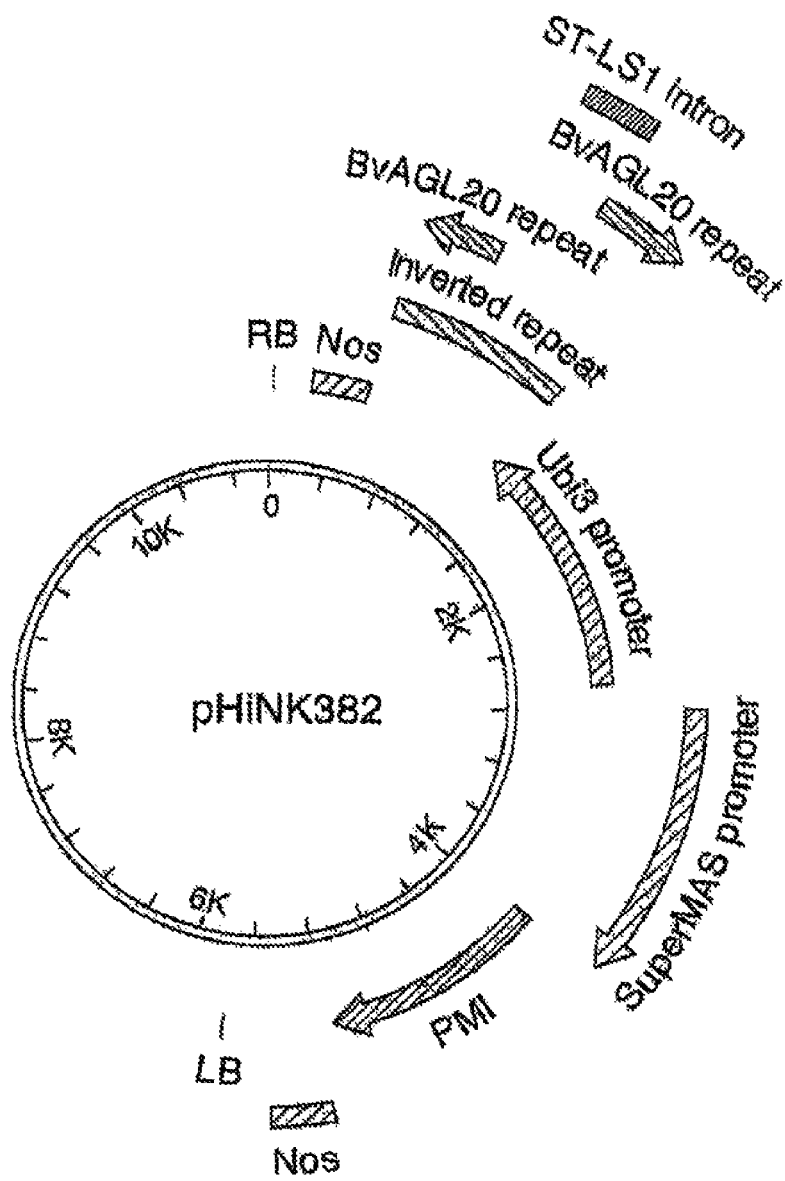
FIG. 3 is a plasmid map of binary vector pHiNK382.

Total RNA was extracted from sugar beet leaves using the RNeasy Plant Mini kit from Qiagen and converted into cDNA using the Superscript™ II RNase H⁻ reverse transcriptase from Life Technologies. Experimental conditions were essentially as described by the suppliers, but using HiNK619 as primer in the reverse transcriptase reaction. The putative AGL20 homologue was amplified starting from the cDNA reaction as template and using primers HiNK619 and HiNK624 in a typical PCR reaction. The thus obtained amplification fragment measured approximately 0.6 Kb in size as was expected according to the sequence of the AGL20 homologues from heterologous species. Upon cloning and sequence analysis, the nucleotide sequence of the sugar beet homologue as listed in FIG. 3 was shown to share strong homology to the AGL20 gene from *Arabidopsis* (FIG. 4) and is referred to as BvAGL20 hereinafter (SEQ ID NO: 6). Albeit that the BvAGL20 fragment did not share as strong homology as observed for the AGL20 homologues from other species, including pine and pea, the homology to AGL20 was stronger than to the any of the other members of the MADS box transcription factors from *Arabidopsis*. A partial genomic sequence including introns 2 to 6 was obtained by designing primers to exons 2 and 7 HiNK725 (5'-ACTAAGACAAT-TATCGGTACCAAAAGC-3', SEQ ID NO: 15) and HiNK729 (5'-AAGGTAGCAGATCTGGTGAAGAAT-TGAG-3', SEQ ID NO: 16), respectively that were used to amplify and sequence the genomic fragment obtained using sugar beet DNA as template in a typical PCR reaction. The partial genomic sequence of the sugar beet homologue (SEQ ID NO: 4) showed strong conservation with respect to the position of the intervening sequences when compared to the *Arabidopsis* sequence, regardless of the fact that the introns in sugar beet are substantially longer than in *Arabidopsis*.

Example 3

Figure 4:
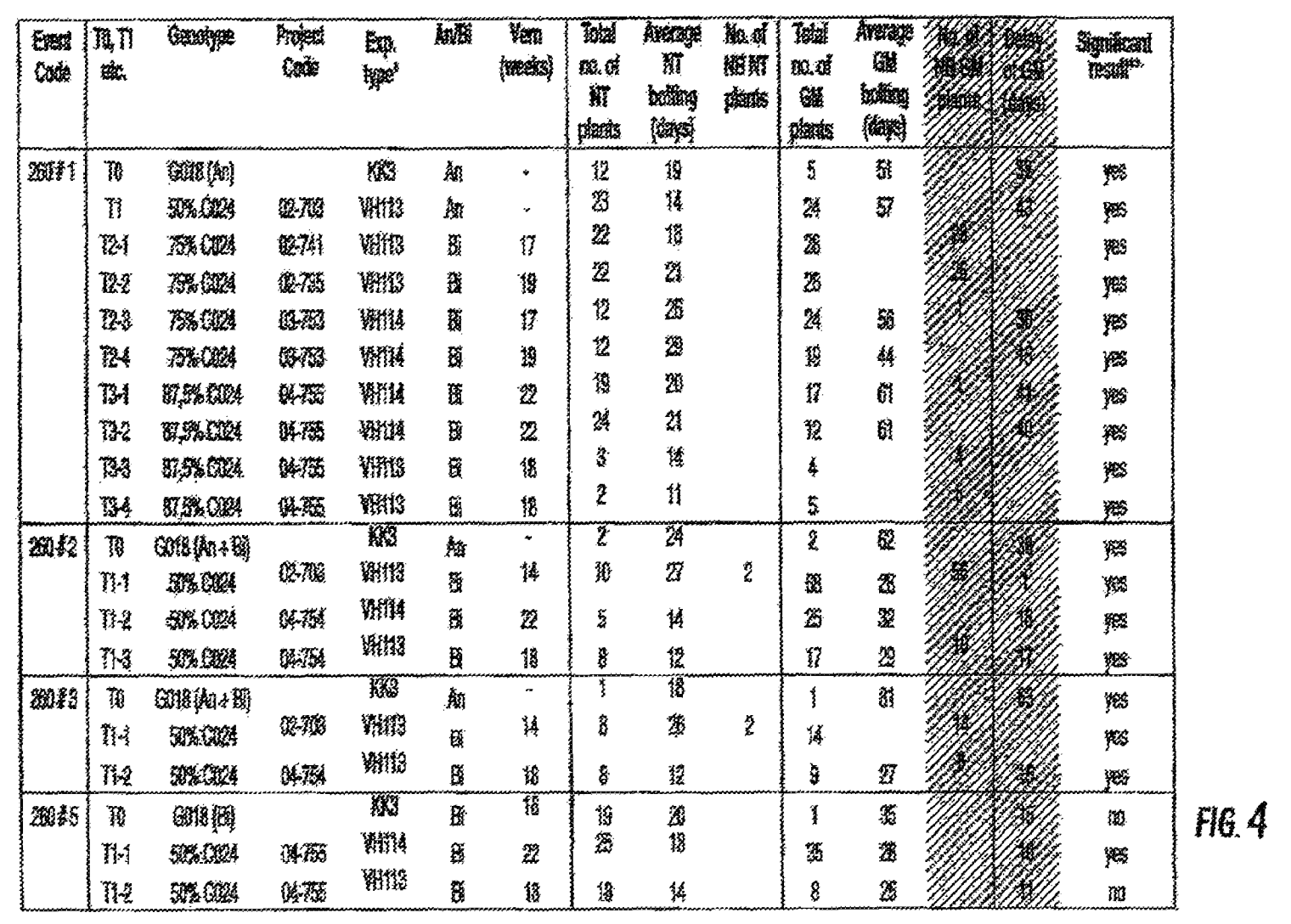

Assembly of the Binary Transformation Vector for RNAi Induced Suppression of the AGL20 Gene in Transgenic Sugar Beet By means of a strategy known as 'recombinant-PCR' (Higuchi, 1990), a 0.28 Kb cDNA fragment consisting of exons 3 to 7 of the AGL20 homologue from sugar beet (SEQ ID NO: 5) was fused to the second intron from the potato ST-LS1 gene (Eckes et al., 1986; Vancanneyt et al., 1990). Care was taken not to include the MADS domain to prevent suppression of other MADS box transcription factors due to the strong sequence conservation of the MADS domain amongst the family of MADS box transcription factors. The BvAGL20 fragment was amplified using primers HiNK792 (5'-CTATGGATCCGCATGCTG ATCTCCTGATC-3', SEQ ID NO: 8) and 793 (5'- GAAGCAGAAACTTACCTAAGA AGT-TAAAAAGTCTCGAAC-3', SEQ ID NO: 9), the first carrying a short linker to add a BamH I restriction site, the latter carrying a tail of 17 nucleotides complementary to the 5' end of the ST-LS1 intron (linkers and tails are underlined hereinafter). The 0.19 Kb fragment comprising the ST-LS1 intron and flanking splicing sites was amplified using primers HiNK529 (5'-ATCCAACCGCGGACCTGCACATCAA CAA-3', SEQ ID NO: 7) and 796 (5'-GACTTT TTAACTTCTTAGGTAAGTTTCTGC TTCTAC-3', SEQ ID NO: 12), HiNK529 carrying a linker including the recognition sequence of Sac II and HiNK796 carrying a tail of 22 nucleotides identical to the 5' extremity of the 0.28 Kb BvAGL20 fragment. As a consequence of the added tails, primers HiNK793 and 796 as well as their cognate amplification products are complementary to each other over a length of 39 nucleotides. By virtue of this overlap both amplification products were fused to each other by means of a second round of PCR using primers HiNK792 and 529 and using a mix of both amplification products as template, yielding a fusion product of 0.47 Kb in length. The 0.28 Kb BvAGL20 fragment was amplified a second time, now using primers HiNK794 (5'-TAAA TCCGCGGAAGAAGTTAAAAAGTCTCGAAC-3', SEQ ID NO: 10) and 795 (5'-CTATTT GTCGACGCATGCTGATCTCCTGATC-3', SEQ ID NO: 11) that differ from HiNK793 respectively HiNK792 with respect to their linkers only; HiNK794 and 795 carry 5' linkers to add a Sac II and a Sal I recognition sequence respectively. Both fragments were fused at the Sac II restriction sites to create an inverted repeat for the BvAGL20 sequence separated by the intron from the potato ST-LS1 gene. The intron was included as spacer fragment to stabilize the inverted repeat, but also to improve the efficiency of the RNAi phenomenon in the future transgenic events (Wang and Waterhouse, 2001; Smith et al., 2000). The thus obtained inverted repeat of approximately 0.75 Kb was subsequently introduced between the Ubi3 promoter from *Arabidopsis* (Norris et al., 1993) and the nos terminator from *Agrobacterium tumefaciens* as a BamH I-Sal I fragment. Subsequently, the gene cassette was transferred as a 2.5 Kb Asc I-Pac I fragment onto the T-DNA of the proprietary binary transformation vector pVictorHiNK, yielding pHiNK382, next to the Super-MAS::PMI::NOS selectable marker gene for mannose selection (FIG. 4). The complete nucleotide sequence of pHiNK382 is disclosed in SEQ. ID NO: 2.

Figure 7:
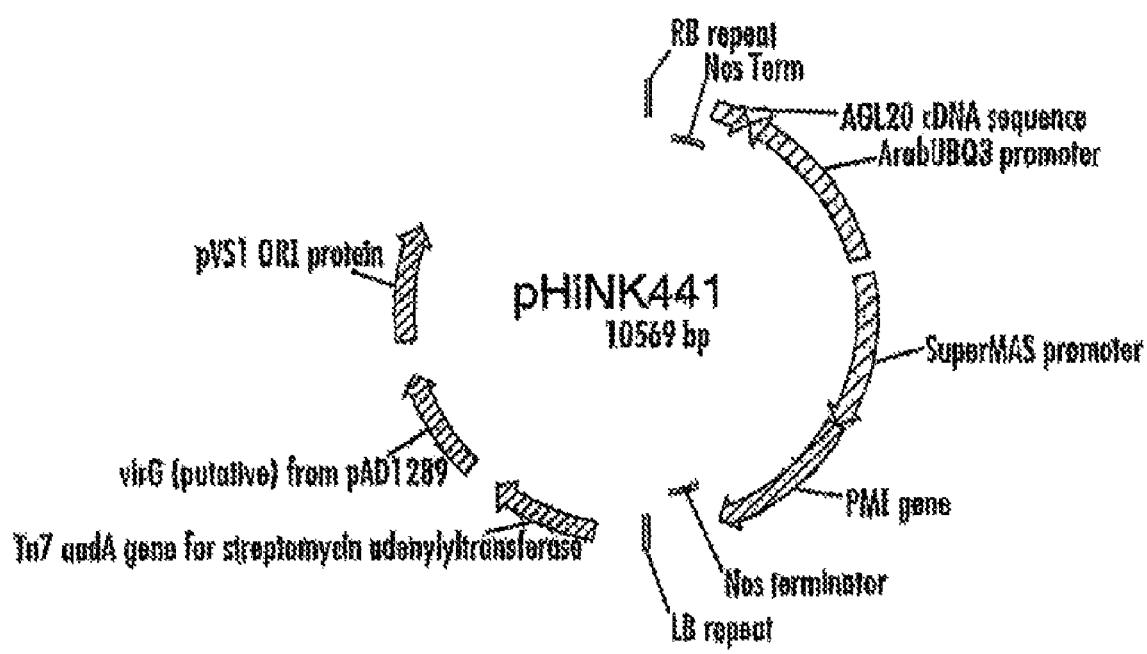
FIG. 7 is a plasmid map of binary vector pHiNK441.

Another embodiment of the invention includes two more binary vectors: pHiNK440 and pHiNK441, that were assembled for the transgenic expression of the BvAGL20 cDNA fragment in sugar beet. Contrary to pHiNK382 that carries an inverted repeat for the BvAGL20 cDNA fragment resulting in the instant formation of a dsRNA or hairpin upon expression of the gene cassette, pHiNK440 and 441 only express the sense or antisense orientation, respectively, of the BvAGL20 cDNA fragment. The dsRNA for BvAGL20 is therefore obtained after crossing events for either vector to each other, resulting in the simultaneous accumulation of the sense and antisense orientation of the cDNA fragment, and in the subsequent formation of a dsRNA. The gene cassettes for the sense (pHiNK440) and antisense (pHiNK441) expression were obtained by amplifying the same 0.28 Kb BvAGL20 fragment (SEQ ID NO: 5) using primers HiNK2617 (5'-TAAATGGATCCAAGAAGTTAAAAAGTCTCGAAC-3', SEQ ID NO: 17) and HiNK795, respectively primers HiNK2618 (5'-GAAGCAGAAACTTACCT-GTCGACAAGAAGTTAAAAAGTCT CGAAC-3', SEQ ID NO: 18) and HiNK792, and the subsequent cloning of the amplification products as BamHI-SalI fragment between the Ubi3 promoter and the nos terminator. As in the case of pHiNK382, the gene cassettes were subsequently transferred as Asc I-Pac I fragments onto the T-DNA of the proprietary binary transformation vector pVictorHiNK that already carried the SuperMAS::PMI::NOS selectable marker for mannose selection, yielding pHiNK440 and 441 (FIGS. 7 and 8). The complete nucleotide sequences of binary vectors pHiNK440 and 441 are disclosed in SEQ. 19 and SEQ. 20 respectively. Upon completion all binary vectors were transformed into *Agrobacterium tumefaciens* strain EHA101 by means of the heatshock protocol described in Holsters et al., 1978.

Therefore, the present invention further includes providing an expression cassette comprising a BvAGL20 cDNA fragment oriented in the sense direction and a second expression cassette comprising the BvAGL20 cDNA fragment oriented in the antisense direction. In one embodiment, the expression cassette including a BvAGL20 cDNA fragment oriented in the sense direction is pHiNK440, wherein an expression cassette including the BvAGL20 cDNA fragment oriented in the antisense direction is pHiNK441.

The present invention further includes a method for the conditional RNAi suppression of endogenous sugar beet expression of AGL20, wherein the method includes: (a) transforming a male or a female sugar beet parental inbred line with a BvAGL20 cDNA fragment oriented in the sense direction and transforming a female or a male parental inbred line with the BvAGL20 cDNA fragment oriented in the antisense direction; (b) crossing the female and male parental lines of (a) to produce a hybrid sugar beet plant, wherein the sense and antisense cDNA fragments form dsRNA in the hybrid sugar beet plant resulting in bolting control of said hybrid plant.

The present invention recognizes that parental lines comprising only a sense or antisense BvAGL20 cDNA fragment will not undergo RNAi of AGL20 expression and therefore will develop to produce flowers and seed for generation of progeny. Only when the sense and antisense fragments are combined in the hybrid plant do the RNAi mechanisms cause suppression of bolting, thereby allowing sugar beet to be sown in autumn in northern latitudes without the risk of bolting and flowering in the following season. This shifts the sugar beet from a traditional spring crop into a winter crop, which permits growers to drill their crop in autumn and to harvest the next summer. It has been shown that winter cultivars typically produce higher yields compared to spring cultivars.

Example 4

Transformation

Intact sugar beet seeds were surface sterilized, germinated and pretreated in vitro. Explants were then transformed via *Agrobacterium tumefaciens* mediated gene transfer, using the multiple shoot protocol disclosed in WO 02/14523 A2.

4.1 Seed Sterilization and Germination

Seeds of sugarbeet (*Beta vulgaris* L.) are surface sterilized and plated onto seed germination medium (GM) under aseptic culture. The GM comprised may contain Murashige and Skoog (MS) salts with about 30 g/L sucrose, myo-inositol (100 mg/L), pantothenic acid (1 mg/L) and appropriate gelling agent were also included in the GM, as were plant growth regulators with cytokinin-like function. Cytokinin levels are generally within a typical range of 0.5 mg/L to 5 mg/L, and usually between 1.0 and 2.0 mg/L. The auxin inhibitor TIBA is also added.

4.2 Excision and Initiation of Shoot Meristematic Cultures

Shoot tips of 10-20 day old seedlings are excised and plated onto shoot multiplication medium (SMM). In this case, the SMM comprised Murashige and Skoog salts with 30 g/L sucrose and appropriate gelling agent. In addition, the SMM contained at least one cytokinin growth regulator such as BA, kinetin, 2-ip or zeatin, generally within a concentration range of about 1 to 10 mg/L and usually within a concentration range of 1-5 mg/L. The shoot tips consisted of both apical and axillary shoot meristematic regions, leaf primordia, 5 mm of hypocotyl and the cotyledonary leaves which are cut off to reduce further elongation. Every 7-10 days following plating, target explants were subcultured to fresh SMM after removing any new elongated leaf material. Multiple shoot target explants are typically cultured under low light intensity (10-30 µEinsteins) for 16 hour day-lengths at ca 21-22° C. After 4 to 7 weeks the multiple shoot cultures resemble compact rosettes and are ready for transformation.

4.3 Inoculation and Incubation of Multiple Shoot Culture

*Agrobacterium tumefaciens* mediated transformation is utilized for the transformation of the multiple shoot culture. The *A. tumefaciens* strain EHA101 containing the binary vectors according to the invention (e.g. pHiNK260; pHiNK382; pHiNK440 and 441) is grown on solid culture medium consisting of 1 g/L yeast extract, 5 g/L peptone and appropriate gelling agent for 2-3 days at 28° C. One day prior to transformation the multiple shoot culture is prepared for inoculation by removing any remaining elongated leaf material.

To begin inoculation, single colonies of *A. tumefaciens* are collected together on the original YEB culture plate using a sterile loop. For the actual inoculation of each target explant, a sterile scapel blade is dipped into the collected *A. tumefaciens* colonies and used to make cuts in the apical and axillary meristem regions of each target. Immediately following this inoculation step, about 7 µl of MSMG Induction Medium (MS salts, 2 g/L Glucose, MES, and 200 µM acetosyringone) is applied to the wounded surface of each target in some experiments. An effort is made to cut through the center of as many meristematic zones as possible in order to direct gene delivery to shoot meristem producing cells. Ten to twenty target cultures are typically treated in sequence and then allowed to air dry under sterile conditions in a laminar flow hood for 10 minutes. Following the air drying treatment, treated target explants are moved to MSCC co-cultivation medium (MS salts, B5 vitamins, 2 mg/L BA, 30 g/L sucrose, 200 µM acetosyringone with appropriate gelling agent). The treated explants are then incubated on MSCC medium for 2-4 days at 21-22° C. with continuous dark culture.

4.4 Target Culture and Selection

Following inoculation and co-cultivation, the multiple shoot explants are transferred to fresh SMM medium with 2 mg/L BA and appropriate antibiotics and gelling agent for a minimum of four days before applying mannose selection pressure. Transformed tissues are selected on gradually increasing amounts of mannose (2.5 g/L-15 g/L) and decreasing amounts of sucrose (20 g/L-3 g/L) following transformation. Mannose selection levels are increased in a stepwise manner, from 2.5 g/L mannose+20 g/L sucrose to 4 g/L mannose+20 g/L sucrose, followed by 5 g/L mannose+20 g/L sucrose, followed by 6 g/L mannose+18 g/L sucrose and 8 g/L mannose+15 g/L sucrose. The multiple shoot cultures continue to grow in size and are carefully divided at each subculturing to promote adequate selection pressure. During this period, the BA level is reduced to 0.25 mg/L and then eliminated to promote shoot elongation. Areas of surviving transformed tissue are continually removed from dying untransformed sections of the original target explant and surviving sections are again carefully divided to promote stringent selection. Selection and shoot regeneration typically progress over a time period of from 10 to about 30 weeks. As young shoots emerge they are separated and isolated under selection for the most efficient selection of transformed shoots.

4.5 Elongation of Transformed Shoots

Once the young shoots reach approximately 0.5-1.5 cm, they are transferred to containers with shoot elongation medium (elongation of developing shoots is enhanced by reduction of cytokinin levels) with mannose selection as described above. The shoot elongation medium containing MS salts, appropriate gelling agent and low levels of cytokinin are incorporated in the elongation medium, within a typical range of 0.1 to 1.0 mg/l. The optimal cytokinin application for sugar beet is 0.2 mg/L kinetin.

4.6 Regeneration of Transformed Plants

Selection of transgenic sugar beet shoots was performed on a standard regeneration medium supplemented with mannose-6-phosphate as selective agent (WO 94/20627).

Transformed shoots are cloned on MS-based cloning medium plus mannose at 5-15 g/L. Multiple shoots from one original transgenic shoot are sometimes desirable, and for this reason a combination of cytokinin and auxin in the basal MS medium was used to induce cloning. Low levels of both growth regulators typically range from 0.1 mg/L to 0.5 mg/L. For sugar beet, MS salts, 30 g/L sucrose and appropriate gelling agent with 0.2 mg/L kinetin, and 0.1 mg/L NAA is used, Some months after inoculation, transgenic shoots were confirmed by means of the PMI-assay or PCR analysis. Clonal propagation and rooting of transgenic shoots were performed on standard propagation and rooting medium, under maintained mannose selection to eliminate chimeric plants that escaped the selection procedure. Finally plants were sent to greenhouse for phenotype testing.

Single shoots or clones are successfully rooted when transferred to a rooting medium containing MS basal medium supplemented with an auxin such as IBA at 0.5 mg/L to 5 mg/L. In one example, the rooting medium contains 5 mg/L IBA and about 12-15 g/L mannose.

It is understood that transformation of plant species is now routine for an impressive number of plant species, including both the Dicotyledoneae as well as the Monocotyledoneae. In principle any transformation method may be used to introduce chimeric DNA according to the invention into a suitable ancestor cell, as long as the cells are capable of being regenerated into whole plants. Methods may suitably be selected from the calcium/polyethylene glycol method for protoplasts (Krens, F. A. et al., 1982; Negrutiu I. et al, 1987), electroporation of protoplasts (Shillito R. D. et al., 1985), microinjection into plant material (Crossway A. et al., 1986), DNA or RNA-coated particle bombardment of various plant material (Klein T. M. et al., 1987), infection with (non-integrative) viruses and the like). One method according to the invention comprises *Agrobacterium*-mediated DNA transfer. Another method according to the invention is the use of the so-called binary vector technology as disclosed in EP A 120 516 and U.S. Pat. No. 4,940,838.

Example 5

Growth Conditions for T0 Generation Plants

Plasmid pHiNK260 was transformed in both annual and biennial sugar beet acceptor genotypes, while pHiNK382 was transformed in biennial material only. The first generation of transformed plants is called T0. Later generations are called T1, T2 etc. Seed was used for experiments using T1, T2 etc generations.

In order to create non-transgenic (NT) control plants, in vitro regenerated sugar beet shoots were produced. Besides of the actual transformation and selection procedure, these NT shoots were treated and rooted similar to the transformed shoots. Every delivery of transgenic plants to the greenhouse was accompanied with at least one NT control plant of the same genotype.

After transfer to the greenhouse, the T0 transformed and NT control shoots were submitted to a rooting phase. The small plants were planted in small pots with soil and grown under enhanced $CO_2$ conditions for two weeks. After these two weeks, the rooted plants were transferred to 12 cm (0.7 liter) pots.

After the rooting phase, annual sugar beet plants were transferred to Biochamber KK3 (17 hours artificial light; 18° C. day+night temperature). The arrival day in KK3 was 'Day 0' and considered the start of the phenotypic analysis experiment.

After the rooting phase, biennial sugar beet plants were transferred to greenhouse VH113 (17 hours light, temperature 18-25° C. day and 15° C. night) for 2 weeks prior to vernalization. Vernalization occurred in cold room KK6 at a constant temperature of 6° C. and 12 hours under low artificial light for several weeks. Generally, sugar beet plants with the genetic background G018 were vernalized for 14 weeks, while G024 material was vernalized for 16 weeks. The day that the plants were taken out of the vernalization room was 'Day 0' and considered the start of the phenotypic analysis experiment. Plants were first slowly acclimatized for two weeks in Biochamber KK5, stepwise increasing the temperature from 10 to 18° C., and subsequently repotted in larger, 16 cm (2 liter) pots and transferred to biochamber KK3.

The phenotypic analysis of the T0 generation events were started on a continuous basis and generally lasted for 3 months (90 days) or until all plants had started bolting. Plants which still had not started bolting after 3 months, were called Non-Bolting (NB) and were re-vernalized in an attempt to induce bolting and flowering for production of the next generation.

Example 6

Growth Conditions of T1, T2, T3 Generations

Summary of Growth Conditions: Phenotypic analysis experiments started from seed. Seed was germinated in 96-format plug-pot trays. In order to establish a uniform germination and root formation, the trays were grown at 17 hours light and temperatures of 18-25° C. day and 16° C. night. After two weeks, the plants were sampled for PCR analysis.

PCR analysis was carried out in order to identify the NT and transgenic plants in the progeny populations. This was achieved by means of a PCR reaction for either the transgene cassette or the selectable marker PMI. Populations segregating in annual and biennial plants were also tested with markers for the B-gene controlling the annual habit.

Using the PCR results, both transgene and NT plants were selected. NT plants functioned as internal control plants and accompanied the transgenic plants throughout the experiment. Only vigorous plants were selected and potted up for the phenotypic analysis of annual plants (Day 0). The biennial plants were kept in the plug-pots and artificially vernalized before entering the experiment. In the second semi-field trial described, biennial plants were planted out before vernalization.

Following the selection of the plants, the phenotypic analysis experiments employed different growth conditions as detailed hereinbelow:

Experiment 02-703 was carried out in greenhouse VH113 in 2002. The annual plants entered the phenotypic analysis directly upon PCR analysis, while the biennial plants were first vernalized in KK6 for 14 weeks. The procedure for vernalization and acclimatization in KK5 was identical as for the T0 generation.

Experiment 02-741 and 735 were combined and carried out in greenhouse VH113. Only biennial plants were selected and these were vernalized in KK6 for 17 and 19 weeks. After the 2 week acclimatization in KK5, vigorous plants were re-potted and transferred to the greenhouse VH113 in the first week of May, 2003.

Experiment 03-753 was carried out in greenhouse VH114. Vernalization occurred artificially in KK6 for 17 and 19 weeks and acclimatization for 2 weeks in KK5. Plants were transplanted in VH114 at the end of April and early May 2004. In this greenhouse, biennial plants were grown in the soil instead of pots. The experiment was therefore called a semi-field trial.

Experiment 04-754 and 755 were combined and carried out as a semi-field trial in greenhouse VH114 from September 2004 to May 2005. Vernalization occurred naturally in the unheated but frost-free greenhouse VH114. The plants were exposed to 13 weeks of mild vernalization (7-12° C.) and 15 weeks of strong vernalization (3-7° C.). Vigorous left-over plants were vernalized artificially for 18 weeks at 6° C. in KK6 and after two weeks of acclimatization in KK5 transferred to VH113 during the middle of March 2005.

Experiment 04-766 and 767 were combined and carried out in the climate chamber KK11 (16 hours light, temperature 18° C. day and 12° C. night). Vigorous biennial plants were vernalized in KK6 for 15 weeks at 6° C. and acclimatized in KK5 for 2 weeks before re-potting and transfer to KK11 (16 hours light, temperature 18° C. day and 12° C. night.

Bolting was scored up to three times per week during the phenotypic analysis experiments. The day of bolting was defined as the first day that stretching of the internodes of the meristem was first visible.

The above experiments are described now in more detail.

Semi Field Trail VH114 September 2004-May 2005 Experiment 04-754 and 755

Seeds were germinated in a greenhouse with both natural and artificial light and heat, in order to obtain uniform germination. After two weeks, the plants in 96-format plug trays were transferred to more natural autumn conditions.

After six weeks, on 20 and 21 Oct. 2004, selected plants were planted out in VH114, in the soil with a conventional field trial layout. Temperature measurements were taken at canopy height (air) and at 10 cm soil depth (soil).

| Drilling Greenhouse VH113; week 37-39 (Mid September 2004) | |
|---|---|
| Temperature: | 18-25° C. day and 16° C. night |
| Light: | 17 H artificial + 12 H natural light; Metal halide lamp OSRAM Power Star HQI-BT 400 W/D; >150-200 μmol/m² |
| Watering: | On daily basis |
| $CO_2$: | ambient |
| Pot size: | Plug pot trays (96-format tray, wells 4 × 4 cm) |

During daytime, light intensity could increase >800 μmol/m² due to sunlight. The lights were switched off when light intensity was >35 klux (600 μmol/m²)

| Pre-vernalization Greenhouse VH111; week 40-43 (End September-Mid October 2004) | |
|---|---|
| Temperature: | 10-15° C. |
| Light: | 12-10 H natural light |
| Watering: | On daily basis |
| $CO_2$: | Ambient |
| Pot size: | Plug pot trays (96-format trays, wells 4 × 4 cm) |

Night vernalization. Plants are transplanted before vernalization.

| Vernalization 'Natural', 22 weeks Greenhouse VH114; week 43-12 (Mid October 2004-End March 2005) | |
|---|---|
| Temperature air: | 0 < X < 12° C. until the end of March (week 13) at canopy height |
| Temperature soil: | 5 < X < 10° C. November-end March (week 13) at 10 cm below surface |
| Light: | Natural light and day length (10 H October - 6 H December - 12 H March) and minimized diffuse light from neighboring greenhouses. Below 200 total radiation PAR until first week February (week 5), increasing PAR up to 1200 PAR in Mid April (week 6-15) |
| Watering: | Seldom - only a few times in total, but like a heavy rain poor. |
| $CO_2$: | Ambient |
| Pot size: | Plants planted in soil as on field (18 cm in rows and 48 cm between rows) |
| Comments: | Temperature: one peak below 0° C. (4 Mar. 2005 at 05:18): −0.49° C. |

Acclimatization

No special temperature acclimatization

| Post-vernalization |
|---|
| Greenhouse VH114; week 12-19 (April-Mid May 2005) |

| | |
|---|---|
| Temperature air: | Most day temp 15-25° C.; most night temp. 5-10° C. at canopy height |
| Temperature soil: | Most day temp 12-15° C.; most night temp. 7-10° C. 10 cm from surface |
| Light: | Natural light and day length 13-16 H >800 total radiation PAR on most days from early April |
| Watering: | Seldom - only a few times, but like a heavy rain shower. |
| $CO_2$: | Ambient |
| Pot size: | Plants planted in soil as on field (18 cm in rows and 48 cm between rows) |

Greenhouse VH113 September 2004-May 2005 Experiment 04-754 and 755

Seeds were germinated in a greenhouse with extra light and heat, in order to obtain uniform germination (same batch as for VH114 experiment). After two weeks, the plants in 96-format plug trays were transferred to more natural autumn conditions.

After six weeks, the left over plants from the semi field trial experiment were artificially vernalized for 18 weeks at 6° C. After artificial acclimatization in steps to 18° C., the plants were re-potted and transferred to a greenhouse with additional and natural light and heat. Air temperature measurements were taken 50 cm above the tables of the climate chamber and greenhouse.

| Drilling |
|---|
| Greenhouse VH113; week 37-39 (Mid September 2004) |

| | |
|---|---|
| Temperature: | 18-25° C. day and 16° C. night |
| Light: | 17 H artificial + 12 H natural light; Metal halide lamp OSRAM Power Star HQI-BT 400 W/D; 150-200 1 μmol/m² |
| Watering: | On daily basis |
| $CO_2$: | ambient |
| Pot size: | Plug pot trays (96-format tray, wells 4 × 4 cm) |

During daytime, light intensity could increase >800 μmol/m² due to sunlight. The lights were switched off when light intensity was >35 klux (600 μmol/m²)

| Pre-vernalization |
|---|
| Greenhouse VH111; week 40-43 (End September-Mid October 2004) |

| | |
|---|---|
| Temperature: | 10-15° C. |
| Light: | 12-10 H natural light |
| Watering: | On daily basis |
| $CO_2$: | Ambient |
| Pot size: | Plug pot trays (96-format trays, wells 4 × 4 cm) |
| Comments: | Night vernalization |

| Vernalization |
|---|
| Artificial, 18 weeks |
| Climate chamber KK6; week 43-8 (Mid October 2004-End February 2005) |

| | |
|---|---|
| Temperature: | Set at 6° C., temperatures 4-8° C. |
| Light: | 12 H artificial light, 8 H incandescent lamp, and 4 H metalhalide lamp |
| Watering: | Weekly basis |
| $CO_2$: | Ambient |
| Pot size: | Plug pot trays (96-format trays, wells 4 × 4 cm) |

During nights with sincere frost, temperatures could have been <6° C., but >0

| Acclimatization |
|---|
| Climate chamber KK5; Week 8-10 (Early March) |

| | |
|---|---|
| Temperature: | [Day 10 + Night 8° C.] to [Day 18 + Night 12° C.] gradually during 14 days |
| Light: | 12 H artificial light; metal halide lamp 100 ± 30 μmol/m² |
| Watering: | Weekly basis |
| $CO_2$: | Ambient |
| Pot size: | Plug pot trays (96-format trays, wells 4 × 4 cm) |

Plants are transplanted at this stage after vernalization

| Post-vernalization |
|---|
| Greenhouse VH113; week 10-19 (Mid March-Mid May 2005) |

| | |
|---|---|
| Temperature: | 18-25° C. day and 15° C. night |
| Light: | 17 H artificial and 10-16 H natural light; metalhalide lamp OSRAM Power Star HQI-BT 400 W/D >150-200 μmol/m² |
| Watering: | On daily basis |
| $CO_2$: | Ambient |
| Pot size: | 2 liter pots |

During daytime, light intensity could increase >800 μmol/m² due to sunlight. The lights were switched off when light intensity was >35 klux (600 μmol/m²)

Climate chamber KK11 (November 2004-June 2005) Experiment 04-766 and 767

Seeds were germinated in a greenhouse with extra light and heat, in order to obtain uniform germination. After three weeks, the plants in 96-format plug trays were artificially vernalized for 16 weeks at 6° C. After artificial acclimatization in steps to 18° C., the plants were re-potted and transferred to a climate chamber with artificial post-vernalization conditions and with close to ambient $CO_2$ levels at 400 ppm. Due to lack of space, the plants were potted up in 12 cm (0.7 litre) pots; smaller than in the VH113 experiment. Air temperature measurements were taken 130 cm above the tables and canopy height of the climate chamber.

| Drilling |
|---|
| Greenhouse VH113; week 48 (End November 2004) |

| | |
|---|---|
| Temperature: | 18-25° C. day and 16° C. night |
| Light: | 17 H artificial + 8 H natural light; Metal halide lamp OSRAM Power Star HQI-BT 400 W/D; >150-200 μmol/m² |

-continued

Drilling
Greenhouse VH113; week 48 (End November 2004)

| | |
|---|---|
| Watering: | On daily basis |
| $CO_2$: | Ambient |
| Pot size: | Plug pot trays (96-format trays, wells 4 × 4 cm) |

During daytime, light intensity could increase >800 µmol/m² due to sunlight. The lights were switched off when light intensity was >35 klux (600 µmol/m²)

Pre-vernalization
Greenhouse VH113; week 49-51, 2004)

| | |
|---|---|
| Temperature: | 18-25° C. day and 16° C. night |
| Light: | 17 H artificial + 8-6 H natural light; Metal halide lamp OSRAM Power Star HQI-BT 400 W/D; 150-200 µmol/m² |
| Watering: | On daily basis |
| $CO_2$: | Ambient |
| Pot size: | Plug pot trays (96-format trays, wells 4 × 4 cm) |

Vernalization
Artificial, 16 weeks
Climate chamber KK12; week 51-14
(End December 2004-Early April 2005)

| | |
|---|---|
| Temperature: | 5-7° C. |
| Light: | Artificial metalhalide lamp, 150 µmol/m2 day length 12 H?? |
| Watering: | On daily basis |
| $CO_2$: | Ambient |
| Pot size: | Plug pot trays (96-format trays, wells 4 × 4 cm) |
| Comments: | Nice vegetative growth, better than KK6; lighter than in KK6 |

Acclimatization
Climate chamber KK5; Week 14-16 (Mid April 2005)

| | |
|---|---|
| Temperature: | [Day 10 + Night 8° C.] to [Day 18 + night 12° C.] gradually during 14 days |
| Light: | 12 H artificial light; metal halide lamp 100 ± 30 µmol/m² |
| Watering: | On daily basis |
| $CO_2$: | Ambient |
| Pot size: | Plug pot trays (96-format trays, wells 4 × 4 cm) |

Plants are transplanted at this stage after vernalization.

Post-vernalization
Climate Chamber OK125:11; week 16-24 (End April-Mid June 2005)

| | |
|---|---|
| Temperature: | 18° C. day and 12° C. night |
| Light: | 16 H artificial; Metal halide lamp, 200 µmol/m2 |
| Watering: | On daily basis |
| $CO_2$: | 400 ppm |
| Pot size: | 12 cm pots |
| Comments: | 15 plants/tray. Dense growth week 16-19 9 plants/tray week 19-24. |

Example 7

Bolting Behavior of AGL20 (pHiNK382) and FLC (pHiNK260) Events

Out of 155 pHiNK260 events overexpressing the FLC gene 34 showed a delay in bolting either in an annual or a biennial background; out of 148 pHiNK382 events suppressing the endogenous AGL20 gene 22 showed a delay in bolting following following a typical vernalization treatment. The strongest events were forced to set seed and the progeny populations of 13 pHiNK260 and 21 pHiNK382 events were tested again for bolting resistance to confirm the results obtained for the T0 generation. The results of the four best pHiNK260 and pHiNK382 events are displayed in FIGS. 5 and 6, respectively, summarizing the results obtained in various generations and phenotypic experiments.

Figure 5:
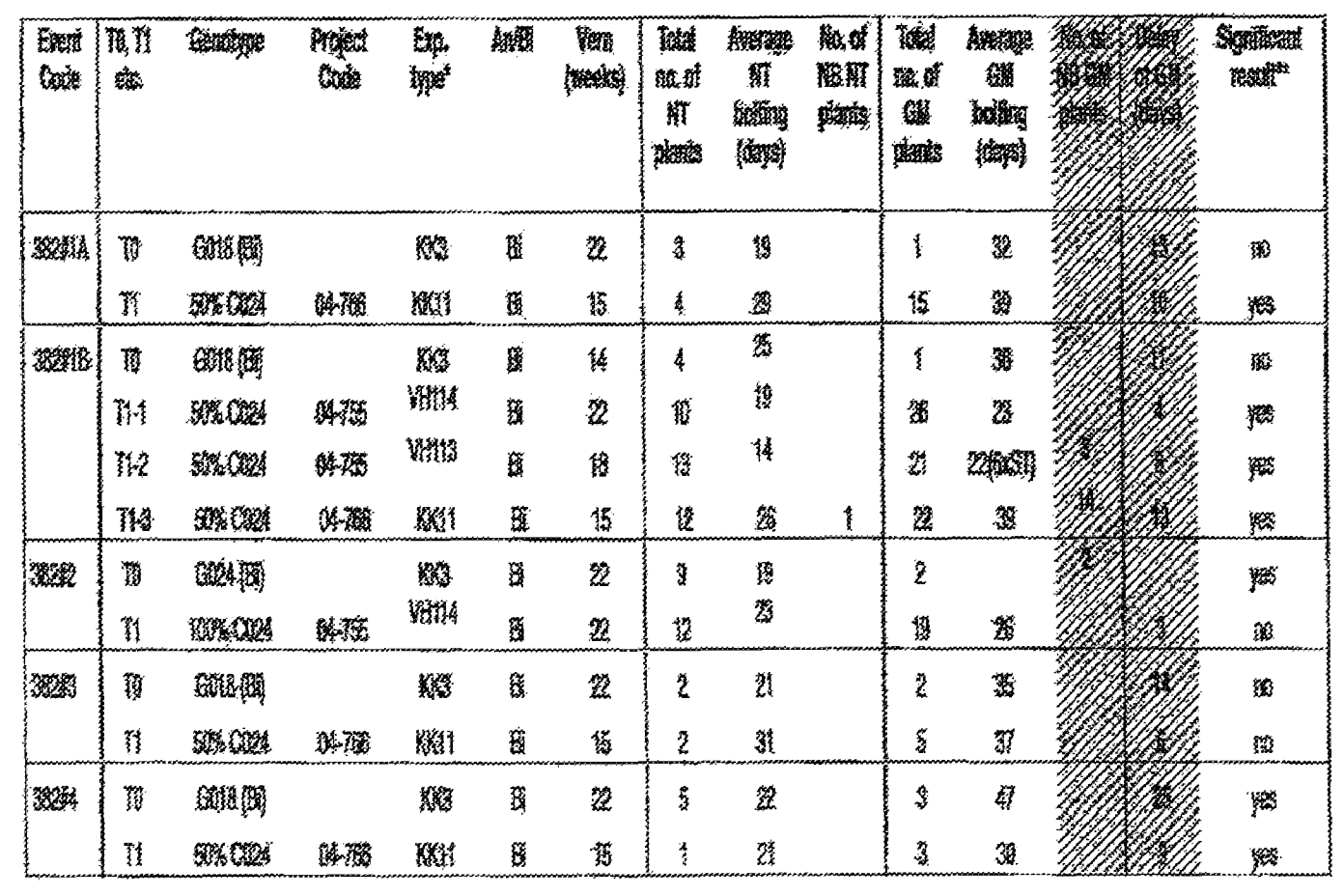

The average bolting day of the transgenic plants was always compared to the average bolting day of the NT control plants. The delay in bolting was calculated as the difference between these two averages (FIG. 5). For instance in experiment T3-2 04-755, the 24 NT plants of event 260#1 started bolting after 21 days on average. The 12 transgene 260#1 plants started bolting after 61 days on average. The delay of bolting for this event in this experiment was therefore 61-21=40 days. In addition, Duncan grouping was carried out in order to test if the differences of NT and transgene bolting times were significant, which is indicated in the final column of FIGS. 5 and 6.

When the plants had still not started bolting at the end of the experiment, the result was recorded as NB (Non-Bolting). In some occasions, some plants did and others did not start bolting during the experiment. For instance in experiment T3-1 04-755, the 19 NT plants of event 260#1 started bolting after 20 days on average. Sixteen of the 17 transgene 260#1 plants started bolting after 61 days on average. One transgene plant, however, did not start bolting. The result of this event was therefore recorded as 17 plants; 61 & 1×NB. The delay of bolting for this event in this experiment was therefore 61-20=41 days & 1×NB.

Not surprisingly, different results were obtained when testing the events under different conditions in the different biochambers and greenhouses. For this reason, the bolting data of the transgenic plants were always compared to the bolting data of the NT control plants.

Figure 6:
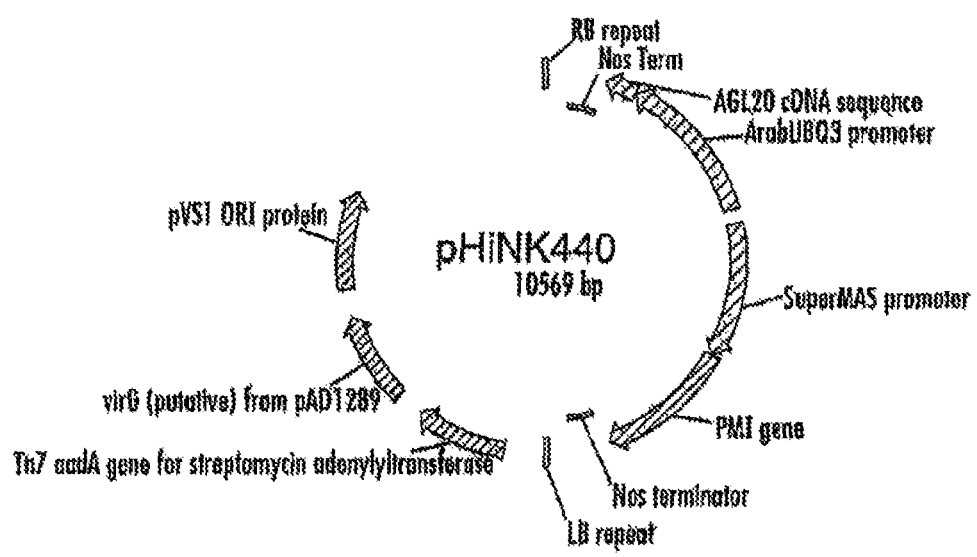
FIG. 6 is a plasmid map of binary vector pHiNK440.

The climate chamber KK11 was the least bolting inductive. Extra delays in bolting were observed, also of NT plants. The low light intensity of 200 µmol/m2 was probably the limiting factor for rapid bolting induction in this climate chamber. Nevertheless, three out of 4 pHiNK382 events tested in KK11 displayed significant delays in bolting (FIG. 6).

The experiments conducted in greenhouse VH113 most frequently showed non bolting plants, notably for the pHiNK260 events #1, #2 and #3 (FIG. 5). For example out of 54 plants analyzed for the T2 generation of event pHiNK260 #1, none of the plants bolted (FIG. 5, experiment T2-1 02-741 and T2-2 02-735). Also pHiNK382 event #1B showed non-bolting plants in the T1 generation (FIG. 6, experiment T1-2 04-755, 3 out of 21).

The conditions of the semi-field trials in VH114 were the most bolting inductive. The soil was cold much longer compared to conditions in pots on tables in a greenhouse following artificial vernalization in cold rooms. Especially the semi-field trial over winter 2004-2005 was extremely bolting inductive. Plants in this semi-field trial perceived 22 weeks (5 months) of vernalizing temperatures, with a high number of accumulating cold degrees (average 5.2° C.). Despite the extreme long vernalization period, plants comprising a FLC or AGL20 event showed significant bolting delay.

Example 8

Bolting Control Under Highly Bolting Inductive Conditions

The following experiment which is described was carried out during the putative winter beet growing season of 2005-2006. Bolting control was further monitored in pHiNK260 and pHiNK382 events under highly bolting inductive conditions.

8.1 Plant Material

Entries consisted of T2 to T4 generations, which were created by crossing individual hemizygous transgenic plants of the selected events with non-transgenic plants. Therefore, each generation segregated in transgenic and non-transgene (NT) plants. The phenotypic screens always consisted of both classes of plants, which were handled and grown identically. In such way, the bolting behaviour of the transgenic plants could be studied and compared to NT plants in the same genetic background. Identification of the transgenic and NT plants in segregating progenies was carried out using PCR analysis as described before. Besides the pollinators used for research purposes, the best two AtFLC events #1 and #2B were also crossed with a potential commercial pollinator.

8.2 Growth conditions

Geographic Information System (GIS) temperature curves were used in order to come even closer to field conditions than in previous semi-field trials. Average weekly maximum, minimum and mean temperatures obtained over the last 12 years (1994-2005) were taken into consideration.

Vernalization in sugar beet occurs between 3 and 12° C. and the GIS data selected in Northern/Mid France are the one with the longest period with vernalizing temperatures on average in Europe. In such way, a bolting experiment was created under extreme stringent bolting conditions.

8.3 Summary of the Growth Conditions

Seeds were drilled and germinated in trays in 96-format plug-pot trays in biochamber KK14. In order to establish a uniform germination and root formation, the trays were grown at 18 hours light and temperatures of 18-21° C. After 2 weeks, the plants were sampled for identification of the transgenic and NT plants by PCR. Stepwise, the temperatures of the biochamber were lowered before the 4 week old plants entered the vernalization period. Plants were transplanted directly into the soil of the greenhouse VH114. The temperature settings of this semi-field trial mimicked the average winter climate for Northern/Mid France: 4 weeks with average weekly temperatures between 0-3° C. and 25 weeks between 3-12° C. The trial was kept frost-free. In total the plants experienced 29 weeks of average weekly temperatures below 12° C. which is considered extremely bolting inductive. During spring the temperature increased slowly, so no special acclimatization period was introduced.

8.3.1 Detailed Growth Conditions

| Drilling |
| --- |
| Growth chamber KK14; week 39-41 (End September-Mid October 2005) |

| | |
| --- | --- |
| Temperature: | 20-21° C. day and night (First 5 days) 18° C. day and night (after 5 days) |
| Light: | 18 H artificial (Metal halide lamp OSRAM Power Star HQI-BT 400 W/D; >150-200 µmol/m2) |

| Drilling |
| --- |
| Growth chamber KK14; week 39-41 (End September-Mid October 2005) |

| | |
| --- | --- |
| Watering: | On daily basis |
| CO2: | 800 ppm |
| Pot size: | Plug pot trays (96-format tray, wells 4 × 4 cm) |

| Pre-vernalization |
| --- |
| Growth chamber KK14; week 42-44 (Mid October-Early November 2005) |

| | |
| --- | --- |
| Temperature: | 16° C. day and 8° C. night (gradual daily increase and decrease of temperature with night vernalization) |
| Light: | 12 H artificial (Metal halide lamp OSRAM Power Star HQI-BT 400 W/D; >150-200 µmol/m2) |
| Watering: | On daily basis |
| CO2: | Ambient 400 to 800 ppm, depending of plant development |
| Pot size: | Plug pot trays (96-format trays, wells 4 × 4 cm) |

| Vernalization |
| --- |
| Greenhouse VH114; week 44-16 (Early November 2005-Mid April 2006) |

| | |
| --- | --- |
| Temperature air: | French GIS data to follow. November day 10° C./night 6° C. December day and night 2-7° C. January. day and night 2-7° C. February. day 10° C./night 4° C. March/April day 12° C./night 4° C. |
| Light: | Natural light and day length (10 H October - 6 H December - 14 H April) Minimized diffuse light from neighboring greenhouses Below 200 total radiation PAR until first week February (week 5), increasing PAR up to 1200 PAR in End April (week 6-16) |
| Watering: | Seldom - only a few times in total, but like a heavy rain poor. |
| CO2: | Ambient |
| Pot size: | No pots: Plants planted directly in soil (20 cm in rows and 50 cm between rows). |

| Post-vernalization |
| --- |
| Greenhouse VH114; week 16-24 (April-Mid June 2006) |

| | |
| --- | --- |
| Temperature air: | Min. day temp 15° C.; Min. night temp. 8° C. at canopy height |
| Light: | Natural light and day length 14-18 H >800 total radiation PAR on most days from early April |
| Watering: | On weekly basis |
| CO2: | Ambient |
| Pot size: | No pots: Plants planted directly in soil (20 cm in rows and 50 cm between rows) |

8.4 Results and Discussion

TABLE 1

Phenotypic results of the selected pHiNK260 (FLC) and pHiNK382 (AGL20) events in the semi-field trial 2005-2006

| | Event Code | Total no. of NT plants | Average NT bolting (days) | No. of bolting GM plants | Average GM bolting (days) | Delay of GM (days) | Delay GM Significant (Duncan) |
|---|---|---|---|---|---|---|---|
| Semi-field | FLC#1 | 12 | 15 | 24 | 46 | 31 | Yes |
| trial | FLC#1 | 11 | 6 | 24 | 34 | 28 | Yes |
| 'French' | hybrid | | | | | | |
| winter | FLC#2B | 12 | 16 | 24 | 38 | 22 | Yes |
| Followed by | FLC#2B | 12 | 5 | 24 | 31 | 26 | Yes |
| 'French' | hybrid | | | | | | |
| spring | FLC#2AB | 48* | 12* | 24 | 24 | 12 | Yes |
| | FLC#4 | 12 | 12 | 24 | 33 | 21 | Yes |
| | FLC#5 | 12 | 11 | 24 | 20 | 9 | Yes |
| | AGL20 382#1 | 12 | 14 | 24 | 20 | 6 | Yes |
| | AGL20 382#2 | 12 | 18 | 24 | 18 | 0 | No |
| | AGL20 382#3 | 12 | 15 | 24 | 21 | 6 | Yes |
| | AGL20 382#4 | 12 | 12 | 24 | 17 | 5 | Yes |

Bolting was scored and defined as the first visible elongation of the apical meristem. Day 1 was 30 Mar. 2006, the first day that bolting in the NT controls was detected. Scoring for bolting was stopped after 12 weeks on day 84. The significance of the gene effect was assessed by applying the statistical Duncan's Multiple Range Test.
*Data from reference NT plants of other entries with the same genetic background.
NT Non-transgenic control plants
GM Transgenic plants, transformed with either FLC plasmid pHiNK260 or AGL20 plasmid pHiNK382

All plants survived the winter conditions of the semi-field trial and were very vigorous in March. Sunny weather in March made the conditions for bolting favourable, and the first bolting non-transgene (NT) plant was detected on March 30. This day was the first day of counting bolting time. The fact that the conditions of the semi-field trial have been highly bolting inductive is demonstrated by the observation that not one single plant remained non-bolting throughout the experiment (84 days of counting). Even plants of the best pHiNK260 events which were non-bolting in previous experiments, eventually bolted.

All FLC entries were significantly delayed compared to the internal NT controls. The least delayed event was FLC 260 #5 that showed a delay of 9 days; the best events were FLC 260 #1 and #2B showing delays of 31 respectively 22 days. These two FLC events were also crossed with a commercial pollinator in order to study the bolting behaviour in a hybrid background. The hybrids were more vigorous than the research genotypes, and bolting was induced earlier in the NT hybrid controls. Nevertheless, the transgenic hybrids still showed a similar delay in bolting of 28 and 26 days respectively.

Also 3 out of 4 AGL20 events (pHiNK382) were significantly delayed in bolting under these extreme stringent bolting conditions, albeit not to the same extend as the FLC events (6 days maximum).

Example 9

RNAi Hybrid Concept 9.1 Plant Material

The vectors pHiNK440 and 441 express only one strand of the BvAGL20 dsRNA fragment, sense and antisense orientation respectively, as is described in Example 3. The dsRNA for BvAGL20 is therefore obtained in the hybrid only, after crossing events for either vector to each other.

In order to test this RNAi hybrid concept, pHiNK440 was transformed into a female (male sterile) sugar beet line, while pHiNK441 was transformed into a sugar beet pollinator line. T0 events obtained were tested for the expression of the transgenes by RT-PCR and pHiNK440×pHiNK441 combined by crossing. The T1 populations segregated in 4 classes: 1) NT, 2) pHiNK440 only, 3) pHiNK441 only, and 4) the hybrid, pHiNK440×441. All 4 classes were identified by PCR and the expression of the transgenes studied by RT-PCR.

9.2 Materials and Methods

DNA was isolated using the GenElute Plant Genomic DNA Miniprep kit from Sigma. RNA was isolated using the RNAqueous-4PCR kit from Ambion. RNA was treated with Dnase I, and the Dnase then removed prior to cDNA production. RNA concentration was measured using the spectrofotometer.

cDNA was produced using the Omniscript Reverse Transcriptase kit and HotStart Taq-polymerase from Qiagen. 1 µg total RNA was used for each reaction and the oligo-dT primer at a total volume 20 µl. After the reverse transcription, the cDNA samples were diluted to 40 µl and used for the RT-PCR reaction at three different concentrations (0.5, 1.0 and 2.0 µl).

The (RT-)PCR set up was carried out in such a way that DNA or cDNA aliquots of all plants were identical for each PCR reaction. PCR reaction bulks were created, so that all plants would be tested with identical PCR mix.

Plasmid pHiNK 440 was identified using the primer pair AGL20 A (5' GTC TCG AAC TTT CTA AAC GGA) and nos termination primer HiNK023 (5' CGC AAG ACC GGC AAC AGG ATT C). Plasmid pHiNK 441 was identified using the primer pair AGL20 B (5' GAT CAT CTG CTC GTT GTT GG) and primer HiNK023.

As RNA household and internal positive control gene, the gene GAPC, Cytosolic glyceraldehyde-3-phosphate dehydrogenase, was used (Reeves et al, 2006) with the primer pair gapCex5/6F (5' GCTGCTGCTCACTTGAAGGGTGG) and gapCex8R (5' CTTCCACCTCTCCAGTCCTT).

Above three PCR reaction were carried out using a PCR programme with a hot start of 15 min at 95° C., followed by 35 cycles of denaturing of 30 sec at 940; annealing of 30 sec at 55° C. and a extension step for 30 sec (+2 sec/cycle) at 72° C. The PCR was finished with a 5 min step at 72° C.

The endogenous BvAGL20 gene was amplified with BvAGL20 specific primers HiNK 729 (5' AAG GTA GCA GAT CTG GTG AAG AAT TGA G) and HiNK 819 (5' TCT GCG TGG AGT GAA AAG TAA AGT G) which cover the gene from putative exon 3 to 8. The PCR programme for BvAGL20 consisted of a hot start of 15 min at 95° C., followed by 30 cycles of denaturing of 30 sec at 920; annealing of 30 sec at 57° C. and a extension step for 2 min at 72° C. The PCR was finished with a 5 min step at 72° C.

The PCR fragments were run on an electrophoresis gel with a composition of different samples of one plant per lane: 1) Water: Negative, no amplification control in order to test if the PCR mix was contaminated. 2) DNA (50 ng/reaction): Positive control of plant DNA in order to confirm that the plant is transgene 3) RNA (200 ng/reaction): Negative, no RT-PCR control in order to check if DNA was successfully removed, and 4) cDNA (0.5, 1.0 and 2.0 µl): Test samples which represents the RNA and should give expression levels.

9.3 Results

This example describes the hybrid of a cross between a parental pHiNK440 line and a pHiNK441 line with high expression for the transgenes. The RT-PCR results of 4 plants of the progeny, one of each class, are shown in Figure x. The results show that the endogenous BvAGL20 gene was down regulated in the hybrid only, but not in the NT, nor plants with a single dsRNA component.

Example 10

Stacked Hybrids of FLC (pHiNK260) and AGL20 (pHiNK382) Events 10.1 Plant Material In addition to monitoring the bolting behaviour of FLC and AGL20 events individually, a limited number of stacked hybrids between both types of events were produced. Crosses between individual plants of FLC and AGL20 events resulted in a segregating population segregating in four different classes: 1) FLC alone, 2) AGL20 alone, 3) Stacked hybrid FLC & AGL20 or 4) NT. All young plants were screened by PCR for their identity, and all four classes entered the phenotypic screen.

10.2 Growth Conditions

Plants of these segregating stacked hybrid populations were artificially vernalized in a biochamber for 16 weeks. Mid April, the plants entered the semi-field trial experiment described in Example 8. Plants of all four classes were transplanted directly into the soil of greenhouse VH1 14.

10.3 Detailed Growth Conditions of the Stacked Hybrids

Drilling
Growth chamber BK6; week 50-52
(Mid December 2005-early January 2006)

| | |
|---|---|
| Temperature: | 20-21° C. day and night (First 5 days) 18° C. day and night (after 5 days) |
| Light: | 18 H artificial (Metal halide lamp OSRAM Power Star HQI-BT 400 W/D; >150-200 µmol/m2) |
| Watering: | On daily basis |
| CO2: | 800 ppm |
| Pot size: | Plug pot trays (96-format tray, wells 4 × 4 cm) |

Pre-vernalization
Growth chamber BK6; week 1-3 (Early January 2006)

| | |
|---|---|
| Temperature: | 16° C. day and 8° C. night (gradual daily increase and decrease of temperature with night vernalization) |
| Light: | 12 H artificial (Metal halide lamp OSRAM Power Star HQI-BT 400 W/D; >150-200 µmol/m2) |
| Watering: | On daily basis |
| CO2: | Ambient 400 to 800 ppm, depending of plant development |
| Pot size: | Plug pot trays (96-format trays, wells 4 × 4 cm) |

Vernalisation
Growth Chamber KK12; week 1-16 (Early January-Mid April 2006)

| | |
|---|---|
| Temperature air: | 5-7° C. |
| Light: | Artificial light 12 H (Metal halide lamp OSRAM Power Star HQI-BT 400 W/D; >150-200 µmol/m2) |
| Watering: | On daily basis |
| CO2: | Ambient |
| Pot size: | Plug pot trays (96-format trays, wells 4 × 4 cm) |

Post-Vernalization

Greenhouse VH114; week 16-24 (April-Mid June 2006)

The plants entered the experiment described in example 8. The first day of counting bolting time was the day that the plants left the vernalization biochamber.

10.4 Results and Discussion

TABLE 2

Phenotypic results of stacked hybrids after artificial vernalization.

| Parental components | | Segregating population of cross AGL20 × FLC | | | | | | | |
|---|---|---|---|---|---|---|---|---|---|
| | | NT | | AGL20 | | | FLC | | |
| | | | | | | Delay in | | | Delay in |
| | | Average | | Average | | bolting | | Average | bolting |
| AGL20 event | FLC events | No. of plants | Bolting (days) | No. of plants | Bolting (days) | vs NT (days) | No. of plants | Bolting (days) | vs NT (days) |
| 382#1 | 260#2A | 4 | 16 | 14 | 23 | 7 | 2 | 26 | 10 |
| 382#1 | 260#2B | 8 | 15 | 4 | 45 | 30 | 2 | 40 | 25 |
| | | | | | | | 1 | — | NB |
| 382#1 | 260#4 | 30* | 17* | 8* | 16* | −1 | 24 | 36 | 19 |
| 382#1 | 260#6 | 5 | 14 | 3 | 19 | 5 | 9 | 29 | 15 |

| Parental components | | Segregating population of cross AGL20 × FLC Stacked hybrid | | | Significant Delay Stack | Additive/ Synergistic |
|---|---|---|---|---|---|---|
| | | | | Delay in bolting | vs single AGL20 or | gene effects in |
| AGL20 event | FLC events | No. of plants | Bolting (days) | vs. NT (days) | FLC plants (Duncan) | stacked hybrid |
| 382#1 | 260#2A | 10 | 40 | 24 | Yes | Yes |
| | | 6 | — | NB | | |
| 382#1 | 260#2B | 2 | — | NB | Yes | Yes |
| 382#1 | 260#4 | 9 | 47 | 30 | Yes | Yes |
| | | 15 | — | NB | | |
| 382#1 | 260#6 | 4 | — | NB | Yes | Yes |

Bolting was scored and defined as the first visible elongation of the apical meristem. Day 1 was the day that the plants left the artificial vernalization and entered the semi-field trial of Example 8. Scoring for bolting was stopped after 98 days. The significance of the gene effect was assessed by applying the statistical Duncan's Multiple Range Test.
*Data from reference NT plants of other entries with the same genetic background in the same experiment.
NT Non-transgene plants
NB Non-bolting plants: Plants which did not show any signal of bolting throughout the whole experiment of 98 days Stacked hybrids of AGL20 event pHiNK382#1 and 4 different FLC events showed a synergistic interaction of the FLC and AGL20 effects on bolting control (Table 2). For example, the effects of the individual events for the first combination was 7 days delay for AGL20 event 382#1 and 10 days for FLC event 260#1, which theoretically adds up to a delay of 17 days for the hybrid. The stacked hybrid, however, showed an additional delay in bolting: 24 days instead of 17 days. Moreover, 6 hybrid plants stayed non-bolting (NB) throughout the experiment for 98 days whereas non-bolting plants were not observed for neither of the individual events. Similar synergistic effects were also obtained for the other 3 hybrid combinations. Notably, while only one single plant of all FLC events analyzed stayed non-bolting, the majority of the stacked hybrids did not start bolting after 3 months, thus illustrating that combining events for the two bolting control genes created a highly significant and synergistic delay in bolting.

Example 11

Industrial Applications

The present invention further includes a method of deriving ethanol and/or sugar from the sugar beet plant of the present invention, wherein the root of the sugar beet plant is the predominant source of ethanol and/or sugar. The sugar and the ethanol derivable from the sugar beet plant and root of the sugar beet plant of the invention also fall within the scope of the present invention. Methods of extracted sugar and ethanol from sources such as sugar beet are very well known in the industry.

In summary, ethanol production includes first washing and then slicing the sugar beets followed by an extraction step. The extraction step produces two products: extracted sugar juice and the beet slices. The beet pulp is typically tried and pelletized and sold as animal feed. Thus, beet pulp and animal feed derived from the sugar beet plant and root of the invention are within the scope of the present invention. The sucrose fraction is typically washed, sterilized or otherwise treated to prevent microbial contamination. The sucrose fraction is then fermented. There are numerous fermentation methodologies known to those skilled in the art. In one embodiment and by way of example only, *Saccharomyces cerevisiae* is the organism that is used in the fermentation step. During the fermentation a large amount of $CO_2$ is produced. The $CO_2$ is used to manufacture beverages, fire extinguishers and in food processing. The product of fermentation, with an alcohol content of 8-15% by volume, is passed on to the distillation unit, where it is concentrated to 95%. A final dehydration step is required to remove the remaining water from the ethanol. Ethanol production is well known in the industry and various different methodologies can be used to produce the final ethanol fuel. Ethanol can also be produced by fermentation of sugar beet molasses, sugar juice, dry sugar beet powder and sugar.

Biogas can also be produced from sugar beet using method commonly known in the industry. Biogas consists of methane, carbon dioxide and a small amount of $H_2S$ and ammonia and is produced during anaerobic fermentation of organic material. The fermentation process takes approximately 1 month. In most cases, the biogas is used for combined heat and power generation. The gas is burnt directly and produces heat that can be used for heating houses or generating power. It also can be used as fuel for vehicles.

Biodiesel can also be generated from sugar beet. Using Fischer-Tropsch synthesis, biogas can be converted to liquid fuel, FT-diesel. At present, the production from biomass is only at the pilot stage, and large-scale Fisher-Tropsch conversion installations using fossil fuels exclusively, most commonly natural gas. The advantage of FT-diesel is that its composition can be optimized for the combustion behavior of the motor. The fuel is free from sulfur and aromatic compounds and compared to ordinary diesel, the emissions contain 8% less nitrogen oxides, 30% less particulate matters, 30% less hybrocarbons (HC), 75% less carbon monoxide and 90% less polluting compounds.

REFERENCES

Levy, Y. Y. and Dean, C. 1998. The Transition to Flowering. Plant Cell, 10:1973-1990

Koornneef, M., Blankestijn-de Vries, H., Hanhart, C., Soppe, W. and Peeters, T. 1994. The phenotype of some late-flowering mutants is enhanced by a locus on chromosome 5 that is not effective in the Landsberg erecta wild-type. The Plant Journal 6: 911-919.

Lee, I., Michaels, S. D., Masshardt, A. S. and Amasino, R. M. (1994) The late-flowering phenotype of FRIGIDA and mutations in LUMINIDEPENDENS is suppressed in the Landsberg erecta strain of *Arabidopsis*. Plant J. 6, 903-909.

Eckes P, Rosahl S, Schell J and Willmitzer L, 1986. Isolation and characterization of a light-inducible, organ-specific gene from potato and analysis of its expression after tagging and transfer into tobacco and potato shoots. Mol. Gen. Genet. 205, 14-22

Nilsson, O., Lee, I., Blázquez, M. A. and Weigel, D. (1998) Flowering-time genes modulate the response to LEAFY activity. Genetics, 150, 403-410.

Kobayashi, Y., Kaya, H., Goto, K., Iwabuchi, M. and Araki, T. (1999) A pair of related genes with antagonistic roles in mediating flowering signals. *Science*, 286, 1960-1962.

Lee, H., Suh, S.-S., Park, E., Cho, E., Ahn, J. H., Kim, S.-G., Lee, J. S., Kwon, Y. M. and Lee, I. (2000) The AGAMOUS-LIKE 20 MADS domain protein integrates floral inductive pathways in *Arabidopsis*. *Genes Dev*. 14, 2366-2376.

Samach, A., Onouchi, H., Gold, S. E., Ditta, G. S., Schwarz-Sommer, Z., Yanofsky, M. F. and Coupland, G. (2000) Distinct roles of CONSTANS target genes in reproductive development of *Arabidopsis*. Science, 288, 1613-1618.

Borner, R., Kampmann, G., Chandler, J., Gleissner, R., Wisman, E., Apel, A. and Melzer, S. (2000) A MADS domain gene involved in the transition to flowering in *Arabidopsis*. Plant J. 24, 591-599.

Elbashier et al. 2001, RNA interference is mediated by 21 and 22 nucleotide RNAs, Genes Dev. 15, 188).

Altschul et al., 1990, Basic local alignment search tool, J. Mol. Biol. 215: 403-410.

Joersbo M, Donaldson I, Kreiberg J, Petersen S G, Brunstedt J and Okkels F T, 1998. Analysis of mannose selection used for transformation of sugar beet. Mol. Breeding 4: 111-117.

Micheals, S D and R M Amasino, 1999. FLOWERING LOCUS C encodes a novel MADS domain protein that acts as a repressor of flowering. The Plant Cell 11: 949-956.

Hood E E, G L Helmer, R T Fraley and M-D Chilton, 1986. The hypervirulence of *Agrobacterium tumefaciens* A281 is encoded in a region of pTiBo542 outside of T-DNA. J Bacteriology 168: 1291-1301.

Higuchi, R, 1990. Recombinant PCR. In: PCR protocols, A guide to methods and application. Innis M A, Gelfand D H, Sninsky J J and White T J (Eds.), Academic Press Inc., San Diego. pp. 177-183.

Vancanneyt G, Schmidt R, O'Connor-Sanchez A, Willmitzer L and Rocha-Sosa M, 1990. Construction of an intron-containing marker gene: Splicing of the intron in transgenic plants and its use in monitoring early events in *Agrobacterium*-mediated plant transformation. Mol. Gen. Genet. 220: 245-250.

Wang M B and Waterhouse P M, 2001. Application of gene silencing in plants. Curr. Opin. Plant Biol. 5:124-150.

Norris S R, SE Meyer and J Callis, 1993. The intron of *Arabidopsis thaliana* polyubiquitin genes is conserved in location and is a quantitative determinant of chimeric gene expression. Plant Mol Biol 21: 895-906.

Holsters M, D de Waele, A Depicker, E Messens, M van Montagu and J Schell, 1978. Transfection and transformation of *Agrobacterium tumefaciens*. Mol Gen Genetics 163: 181-187.

Krens, F. A. et al., 1982, In vitro transformation of plant protoplasts with Ti-plasmid DNA, Nature 296, 72-74.

Negrutiu I. et al, 1987, Hybrid genes in the analysis of transformation conditions, Plant Mol. Biol. 8, 363-373.

Shillito R. D. et al., 1985, High efficiency direct gene transfer to plants, Bio/Technol. 3, 1099-1102.

Crossway A. et al., 1986, Integration of foreign DNA following microinjection of tobacco mesophyll protoplasts, Mol. Gen. Genet. 202, 179-185.

Klein T. M. et al., 1987, High-velocity microprojectiles for delivering nucleic acids into living cells, Nature 327, 70.

Smith N A, Singh S P, Wang M B, Stoutjesdijk P A Green A G and Waterhouse P M, 2000. Total silencing by intron-spliced hairpin RNAs. Nature 407: 319-320

Jaggard, K. W., Wickens, R., Webb, D. J. and Scott, R. K. 1983. Effects of sowing date on plant establishment and bolting and the influence of these factors on yields of sugar beet. Journal of Agricultural Science, Cambridge, 101, 147-161.

Needleman & Wunsch, 1970, A general method applicable to the search for similarities in the amino acid sequence of two proteins, J. Mol. Biol. 48: 443.

Pearson & Lipman, Proc. Nat'l. Acad. Sci. USA 85: 2444 (1988)

Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, N.Y.

Pařenicová L et al., 2003. Molecular and phylogenetic analyses of the complete MADS-box transcription factor family in *Arabidopsis*: New openings to the MADS world. Plant Cell 15: 1538-1551.

Reeves, Patrick A., He, Yuehui, Schmitz, Robert J., Amasino, Richard M., Panella, Lee W. and Richards, Christopher M. 2006 Evolutionary conservation of the FLC-mediated vernalization response: evidence from the sugar beet (*Beta vulgaris*) Genetics: Published Articles Ahead of Print, published on Dec. 18, 2006 as 10.1534/genetics. 106.069336

What is claimed is:

1. A transgenic sugar beet cell or plant comprising in its genome
   i. a first-heterologous gene construct comprising the FLC coding region consisting of SEQ ID NO:3 operably linked to a promoter, and
   ii. a second heterologous gene construct comprising a heterologous DNA, which when transcribed forms a double stranded RNA molecule that inhibits sugar beet AGL20 gene expression, wherein said heterologous DNA is inserted between a promoter and terminator.

2. The transgenic sugar beet cell or plant according to claim 1, wherein said second gene construct is comprised in an expression cassette.

3. The transgenic sugar beet plant according to claim 1, wherein co-expression of the first and second heterologous gene construct leads to a synergistic delay of the vernalization response in said sugar beet plant.

4. The transgenic sugar beet plant according to claim 1, wherein co-expression of the first and second heterologous gene construct leads to a complete suppression of the vernalization response in said sugar beet plant resulting in a non-bolting (NB) phenotype.

* * * * *

SEQUENCE LISTING

<160> NUMBER OF SEQ ID NOS: 37

<210> SEQ ID NO 1
<211> LENGTH: 9810
<212> TYPE: DNA
<213> ORGANISM: Artificial
<220> FEATURE:
<223> OTHER INFORMATION: Artificial Sequence
<220> FEATURE:
<221> NAME/KEY: pHiNK260
<222> LOCATION: (1)..(9810)
<223> OTHER INFORMATION: pVictorHiNK + 35S-FLCcDNA-mas + SMAS-PMI-nos
<220> FEATURE:
<221> NAME/KEY: misc_feature
<222> LOCATION: (553)..(587)
<223> OTHER INFORMATION: Right T-DNA border
<220> FEATURE:
<221> NAME/KEY: terminator
<222> LOCATION: (786)..(1518)
<223> OTHER INFORMATION: Mas
<220> FEATURE:
<221> NAME/KEY: gene
<222> LOCATION: (1519)..(2378)
<223> OTHER INFORMATION: flc cDNA
<220> FEATURE:
<221> NAME/KEY: promoter
<222> LOCATION: (2398)..(2817)
<223> OTHER INFORMATION: CaMV 35S
<220> FEATURE:
<221> NAME/KEY: promoter
<222> LOCATION: (3260)..(4446)
<223> OTHER INFORMATION: SuperMAS promoter
<220> FEATURE:
<221> NAME/KEY: gene
<222> LOCATION: (4459)..(5634)
<223> OTHER INFORMATION: PMI
<220> FEATURE:
<221> NAME/KEY: terminator
<222> LOCATION: (5702)..(5959)
<223> OTHER INFORMATION: nos
<220> FEATURE:
<221> NAME/KEY: misc_feature
<222> LOCATION: (6056)..(6089)
<223> OTHER INFORMATION: Left T-DNA border
<220> FEATURE:
<221> NAME/KEY: gene
<222> LOCATION: (6433)..(7221)
<223> OTHER INFORMATION: spectinomycin resistance

<400> SEQUENCE: 1

```
gcacgaaccc cccgttcagc ccgaccgctg cgccttatcc ggtaactatc gtcttgagtc      60
caacccggta agacacgact tatcgccact ggcagcagcc actggtaaca ggattagcag     120
agcgaggtat gtaggcggtg ctacagagtt cttgaagtgg tggcctaact acggctacac     180
tagaagaaca gtatttggta tctgcgctct gctgaagcca gttaccttcg gaaaaagagt     240
tggtagctct tgatccggca aacaaaccac cgctggtagc ggtggttttt tgtttgcaa     300 gcagcagatt acgcgcagaa aaaaaggatc tcaagaagat cctttgatct tttctacggg     360
gtctgacgct cagtggaacg aaaactcacg ttaagggatt ttggtcatga gattatcaaa     420
aaggatcttc acctagatcc ttttgatccg gaattaattc ctgtggttgg catgcacata     480
caaatggacg aacggataaa ccttttcacg ccctttaaaa tatccgatta ttctaataaa     540
cgctcttttc tcttaggttt acccgccaat atatcctgtc aaacactgat agtttaaact     600
gaaggcggga aacgacaatc tgatcatgag cggagaatta agggagtcac gttatgaccc     660
ccgccgatga cgcgggacaa gccgttttac gtttggaact gacagaaccg caacgctgca     720
ggaattggcc gcagcggcca tttaaatcaa ttgggcgcgc cgaattcgag ctcggtaccg     780
```

```
ggcccccccct cgaggccgac caaccgcaag cgttgtcagt gttgcaaagc gctctgtgtg    840
ggcctacttt aattgcttcc agtgttaaat tggcgaaagg caataatatc gcaaaatatt    900
gtgttgtaaa atgtaattat gttttaattt catggaaatg tttgagcata attttatta    960 atgtactaaa ttactgtttt gttaaatgca attttgcttt ctcgggattt taatatcaaa   1020
atctatttag aaatacacaa tattttgttg caggcttgct ggagaatcga tctgctatca   1080
taaaaattac aaaaaaattt tatttgcctc aattatttta ggattggtat taaggacgct   1140
taaattattt gtcgggtcac tacgcatcat tgtgattgag aagatcagcg atacgaaata   1200
ttcgtagtac tatcgataat ttatttgaaa attcataaga aaagcaaacg ttacatgaat   1260
tgatgaaaca atacaaagac agataaagcc acgcacattt aggatattgg ccgagattac   1320
tgaatattga gtaagatcac ggaatttctg acaggagcat gtcttcaatt cagcccaaat   1380
ggcagttgaa atactcaaac cgccccatat gcaggagcgg atcattcatt gtttgtttgg   1440
ttgcctttgc caacatggga gtccaaggtt tcagggaagc tggaattcac tagtgattgt   1500
aaaacgacgg ccagtgcctt tttttttttt tttttttac actcaagatc tcgatgcaat   1560
tctcacacga ataaggtaca aagttcatca acctttttgtc ttaaaacaga tagtattgac   1620
ttagttccgt ctacttaagt atcacacaca aagtctcttg gccaaagaga gagtattaag   1680
atatacatac gctcgccctt atcagcggaa taattacata tcttattttt ttttcttcat   1740
aattatatat gttttggatt ttgatttcaa ccgccgattt aaggtggtta attaagtagt   1800
gggagagtca ccggaagatt gtcggagatt tgtccagcag gtgacatctc catctcagct   1860
tctgctccca catgatgatt attctccatc tggctagcca aaacctggtt ctcttctttc   1920 agcatttttct cctttttcttt aagattcaca acaagcttca acatgagttc ggtcttcttg   1980
gctctagtca cggagagggc agtctcaagg tgttcctcca gttgaacaag agcatcgata   2040
ctcacatttt tgacatttga tcccacaagc ttgctatcca caagttcaag tagctcatag   2100
tgtgaaccat agttcagagc ttttgactga tgatccaagg ctttaagatc atcagcatgc   2160
tgtttcccat atcgatcaag gatcttgacc aggttatcgc cggaggagaa gctgtagagc   2220
ttgccggagg cggagacgac gagaagagcg acggatgcgt cacagagaac agaaagctga   2280
cgagctttct cgatgagacc gttgcgacgt ttggagaagg tgacttgtcg gctacttttg   2340
ttctcaattc gcttgatttc taattttcttt cttcccatgg tcaagagtcc cccgtgttct   2400
ctccaaatga aatgaacttc cttatataga ggaagggtct tgcgaaggat agtgggattg   2460
tgcgtcatcc cttacgtcag tggagatatc acatcaatcc acttgctttg aagacgtggt   2520
tggaacgtct tctttttcca cgatgctcct cgtgggtggg ggtccatctt tgggaccact   2580
gtcggcagag gcatcttcaa cgatggcctt tcctttatcg caatgatggc atttgtagga   2640
gccaccttcc ttttccacta tcttcacaat aaagtgacag atagctgggc aatggaatcc   2700
gaggaggttt ccggatatta ccctttgttg aaaagtctca attgcccttt ggtcttctga   2760
gactgtatct ttgatatttt tggagtagac aagtgtgtcg tgctccacca tgttgacgaa   2820
gattttcttc ttgtcattga gtcgtaagag actctgtatg aactgttcgc cagtcttttac   2880 ggcgagttct gttaggtcct ctatttgaat ctttgactcc atgaagctaa actgaaggcg   2940
ggaaacgaca atctgatcca agctcaagct gctctagcat tcgccattca ggctgcgcaa   3000
ctgttgggaa gggcgatcgg tgcgggcctc ttcgctatta cgccagctgg cgaaaggggg   3060
atgtgctgca aggcgattaa gttgggtaac gccagggttt tcccagtcac gacgttgtaa   3120
aacgacggcc agtgccaagc ttgcatgcct gcaggcatgc aagcttcgta cgttaattaa   3180
```

```
ttcgaatccg gagcggccgc acgcgtgggc ccgtttaaac ctcgagagat ctgctagcat    3240
cgatggtacc gagctcgaga ctagctacag gccaaattcg ctcttagccg tacaatatta    3300
ctcaccggtg cgatgccccc catcgtaggt gaaggtggaa attaatgatc catcttgaga    3360
ccacaggccc acaacagcta ccagtttcct caagggtcca ccaaaaacgt aagcgcttac    3420
gtacatggtc gataagaaaa ggcaatttgt agatgttaac atccaacgtc gctttcaggg    3480
atcccgaatt ccaagcttgg aattcgggat cctacaggcc aaattcgctc ttagccgtac    3540
aatattactc accggtgcga tgcccccat cgtaggtgaa ggtggaaatt aatgatccat    3600
cttgagacca caggcccaca acagctacca gtttcctcaa gggtccacca aaaacgtaag    3660
cgcttacgta catggtcgat aagaaaaggc aatttgtaga tgttaacatc caacgtcgct    3720
ttcagggatc cgaattcca gcttggaat tcgggatcct acaggccaaa ttcgctctta    3780
gccgtacaat attactcacc ggtgcgatcc cccatcgta ggtgaaggtg gaaattaatg    3840
atccatcttg agaccacagg cccacaacag ctaccagttt cctcaagggt ccaccaaaaa    3900
cgtaagcgct tacgtacatg gtcgataaga aaggcaatt tgtagatgtt aacatccaac    3960
gtcgctttca gggatcccga attccaagct gggctgcag tcaatccca ttgcttttga    4020 agcagctcaa cattgatctc tttctcgagg agattttc aaatcagtgc gcaagacgtg    4080
acgtaagtat ccgagtcagt ttttatttt ctactaattt ggtcgtttat tcggcgtgt    4140 aggacatggc aaccgggcct gaatttcgcg ggtattctgt ttctattcca acttttctt    4200 gatccgcagc cattaacgac ttttgaatag atacgctgac acgccaagcc tcgctagtca    4260
aaagtgtacc aaacaacgct ttacagcaag aacggaatgc gcgtgacgct cgcggtgacg    4320
ccatttcgcc ttttcagaaa tggataaata gccttgcttc ctattatatc ttcccaaatt    4380
accaatacat tacactagca tctgaatttc ataaccaatc tcgatacacc aaatcgagat    4440
ctgcagggat ccccgatcat gcaaaaactc attaactcag tgcaaaacta tgcctggggc    4500
agcaaaacgg cgttgactga actttatggt atggaaaatc cgtccagcca gccgatggcc    4560
gagctgtgga tgggcgcaca tccgaaaagc agttcacgag tgcagaatgc cgccggagat    4620 atcgttttcac tgcgtgatgt gattgagagt gataaatcga ctctgctcgg agaggccgtt    4680
gccaaacgct ttggcgaact gccttttctg ttcaaagtat tatgcgcagc acagccactc    4740
tccattcagg ttcatccaaa caaacacaat tctgaaatcg gttttgccaa agaaaatgcc    4800
gcaggtatcc cgatggatgc cgccgagcgt aactataaag atcctaacca caagccggag    4860
ctggtttttg cgctgacgcc tttccttgcg atgaacgcgt tcgtgaatt tccgagatt    4920 gtctccctac tccagccggt cgcaggtgca catccggcga ttgctcactt tttacaacag    4980
cctgatgccg aacgtttaag cgaactgttc gccagcctgt tgaatatgca gggtgaagaa    5040
aaatcccgcg cgctggcgat tttaaaatcg cccctcgata gccagcaggg tgaaccgtgg    5100
caaacgattc gtttaatttc tgaattttac ccggaagaca gcggtctgtt ctccccgcta    5160
ttgctgaatg tggtgaaatt gaaccctggc gaagcgatgt tcctgttcgc tgaaacaccg    5220
cacgcttacc tgcaaggcgt ggcgctggaa gtgatggcaa actccgataa cgtgctgcgt    5280
gcgggtctga cgcctaaata cattgatatt ccggaactgg ttgccaatgt gaaattcgaa    5340
gccaaaccgg ctaaccagtt gttgacccag ccggtgaaac aaggtgcaga actggacttc    5400
ccgattccag tggatgattt tgccttctcg ctgcatgacc ttagtgataa agaaaccacc    5460
attagccagc agagtgccgc cattttgttc tgcgtcgaag gcgatgcaac gttgtggaaa    5520
ggttctcagc agttacagct taaaccgggt gaatcagcgt ttattgccgc caacgaatca    5580
```

```
ccggtgactg tcaaaggcca cggccgttta gcgcgtgttt acaacaagct gtaagagctt    5640
actgaaaaaa ttaacatctc ttgctaagct gggagctcgt cgacggatcg aattcctgca    5700
gatcgttcaa acatttggca ataaagtttc ttaagattga atcctgttgc cggtcttgcg    5760
atgattatca tataatttct gttgaattac gttaagcatg taataattaa catgtaatgc    5820
atgacgttat ttatgagatg ggttttatg attagagtcc cgcaattata catttaatac    5880
gcgatagaaa acaaaatata gcgcgcaacc taggataaat tatcgcgcgc ggtgtcatct    5940
atgttactag atctctagaa ctagtggatc tgctagccct gcaggaaatt taccggtgcc    6000
cgggcggcca gcatggccgt atccgcaatg tgttattaag ttgtctaagc gtcaatttgt    6060
ttacaccaca atatatcctg ccaccagcca gccaacagct ccccgaccgg cagctcggca    6120
caaaatcacc actcgataca ggcagcccat cagaattaat tctcatgttt gacagcttat    6180
catcgactgc acggtgcacc aatgcttctg gcgtcaggca gccatcggaa gctgtggtat    6240
ggctgtgcag gtcgtaaatc actgcataat tcgtgtcgct caaggcgcac tcccgttctg    6300
gataatgttt tttgcgccga catcataacg gttctggcaa atattctgaa atgagctgtt    6360
gacaattaat catccggctc gtataatgtg tggaattgtg agcggataac aatttcacac    6420
aggaaacaga ccatgaggga agcgttgatc gccgaagtat cgactcaact atcagaggta    6480
gttggcgtca tcgagcgcca tctcgaaccg acgttgctgg ccgtacattt gtacggctcc    6540
gcagtggatg gcggcctgaa gccacacagt gatattgatt tgctggttac ggtgaccgta    6600
aggcttgatg aaacaacgcg gcgagctttg atcaacgacc ttttggaaac ttcggcttcc    6660
cctggagaga gcgagattct ccgcgctgta gaagtcacca ttgttgtgca cgacgacatc    6720
attccgtggc gttatccagc taagcgcgaa ctgcaatttg gagaatggca gcgcaatgac    6780
attcttgcag gtatcttcga gccagccacg atcgacatta tctggctat cttgctgaca    6840 aaagcaagag aacatagcgt tgccttggta ggtccagcgg cggaggaact ctttgatccg    6900
gttcctgaac aggatctatt tgaggcgcta aatgaaacct taacgctatg gaactcgccg    6960
cccgactggg ctggcgatga gcgaaatgta gtgcttacgt tgtcccgcat ttggtacagc    7020
gcagtaaccg gcaaaatcgc gccgaaggat gtcgctgccg actgggcaat ggagcgcctg    7080
ccggcccagt atcagcccgt catacttgaa gctaggcagg cttatcttgg acaagaagat    7140
cgcttggcct cgcgcgcaga tcagttggaa gaatttgttc actacgtgaa aggcgagatc    7200
accaaagtag tcggcaaata aagctctagt ggatccccga ggaatcggcg tgagcggtcg    7260
caaaccatcc ggcccggtac aaatcggcgc ggcgctgggt gatgacctgg tgagaagtt    7320 gaaggccgcg caggccgccc agcggcaacg catcgaggca gaagcacgcc ccggtgaatc    7380
gtggcaagcg gccgctgatc gaatccgcaa agaatcccgg caaccgccgg cagccggtgc    7440
gccgtcgatt aggaagccgc ccaagggcga cgagcaacca gattttttcg ttccgatgct    7500
ctatgacgtg ggcacccgcg atagtcgcag catcatggac gtggccgttt tccgtctgtc    7560
gaagcgtgac cgacgagctg gcgaggtgat ccgctacgag cttccagacg ggcacgtaga    7620
ggtttccgca gggccggccg gcatggccag tgtgtgggat tacgacctgg tactgatggc    7680
ggtttcccat ctaaccgaat ccatgaaccg ataccgggaa gggaagggag acaagcccgg    7740
ccgcgtgttc cgtccacacg ttgcggacgt actcaagttc tgccggcgag ccgatggcgg    7800
aaagcagaaa gacgacctgg tagaaacctg cattcggtta aacaccacgc acgttgccat    7860
gcagcgtacg aagaaggcca agaacggccc cctggtgacg gtatccgagg gtgaagcctt    7920
gattagccgc tacaagatcg taagagcga aaccgggcgg ccggagtaca tcgagatcga    7980
```

```
gctagctgat tggatgtacc gcgagatcac agaaggcaag aacccggacg tgctgacggt    8040
tcaccccgat tactttttga tcgatcccgg catcggccgt tttctctacc gcctggcacg    8100
ccgcgccgca ggcaaggcag aagccagatg gttgttcaag acgatctacg aacgcagtgg    8160
cagcgccgga gagttcaaga agttctgttt caccgtgcgc aagctgatcg ggtcaaatga    8220
cctgccggag tacgatttga aggaggaggc ggggcaggct ggcccgatcc tagtcatgcg    8280
ctaccgcaac ctgatcgagg gcgaagcatc cgccggttcc taatgtacgg agcagatgct    8340
agggcaaatt gccctagcag gggaaaaagg tcgaaaaggt ctctttcctg tggatagcac    8400
gtacattggg aacccaaagc cgtacattgg gaaccggaac ccgtacattg ggaacccaaa    8460
gccgtacatt gggaaccggt cacacatgta agtgactgat ataaaagaga aaaaaggcga    8520
tttttccgcc taaaactctt taaaacttat taaaactctt aaaacccgcc tggcctgtgc    8580
ataactgtct ggccagcgca cagccgaaga gctgcaaaaa gcgcctaccc ttcggtcgct    8640
gcgctcccta cgccccgccg cttcgcgtcg gcctatcgcg gccgctggcc gctcaaaaat    8700
ggctggccta cggccaggca atctaccagg gcgcggacaa gccgcgccgt cgccactcga    8760
ccgccggcgc tgaggtctgc ctcgtgaaga aggtgttgct gactcatacc aggcctgaat    8820
cgccccatca tccagccaga aagtgaggga gccacggttg atgagagctt tgttgtaggt    8880
ggaccagttg gtgattttga acttttgctt gccacggaa cggtctgcgt tgtcgggaag    8940
atgcgtgatc tgatccttca actcagcaaa agttcgattt attcaacaaa gccgccgtcc    9000
cgtcaagtca gcgtaatgct ctgccagtgt acaaccaat taaccaattc tgattagaaa    9060
aactcatcga gcatcaaatg aaactgcaat ttattcatat caggattatc aataccatat    9120
ttttgaaaaa gccgtttctg taatgaagga gaaaactcac cgaggcagtt ccataggatg    9180
gcaagatcct ggtatcggtc tgcgattccg actcgtccaa catcaataca acctattaat    9240
ttcccctcgt caaaaataag gttatcaagt gagaaatcac catgagtgac gactgaatcc    9300
ggtgagaatg gcaaaagctc tgcattaatg aatcggccaa cgcgcgggga gaggcggttt    9360
gcgtattggg cgctcttccg cttcctcgct cactgactcg ctgcgctcgg tcgttcggct    9420
gcggcgagcg gtatcagctc actcaaaggc ggtaatacgg ttatccacag aatcagggga    9480
taacgcagga aagaacatgt gagcaaaagg ccagcaaaag gccaggaacc gtaaaaaggc    9540
cgcgttgctg gcgtttttcc ataggctccg ccccccctgac gagcatcaca aaaatcgacg    9600
ctcaagtcag aggtggcgaa acccgacagg actataaaga taccaggcgt ttccccctgg    9660
aagctccctc gtgcgctctc ctgttccgac cctgccgctt accggatacc tgtccgcctt    9720
tctcccttcg ggaagcgtgg cgctttctca tagctcacgc tgtaggtatc tcagttcggt    9780
gtaggtcgtt cgctccaagc tgggctgtgt                                     9810
```

<210> SEQ ID NO 2  
<211> LENGTH: 11051  
<212> TYPE: DNA  
<213> ORGANISM: Artificial  
<220> FEATURE:  
<223> OTHER INFORMATION: Artificial  
<220> FEATURE:  
<221> NAME/KEY: pHiNK382  
<222> LOCATION: (1)..(11051)  
<223> OTHER INFORMATION: pVictorHiNK + Ubi3::BvAGL20_dsRNA::Nos + SuperMas::PMI::Nos  
<220> FEATURE:  
<221> NAME/KEY: misc_feature  
<222> LOCATION: (1)..(25)  
<223> OTHER INFORMATION: Right T-DNA border  
<220> FEATURE:  
<221> NAME/KEY: repeat_region

```
<222> LOCATION: (233)..(1292)
<223> OTHER INFORMATION: BvAGL20 inverted repeat
<220> FEATURE:
<221> NAME/KEY: terminator
<222> LOCATION: (233)..(527)
<223> OTHER INFORMATION: Nos terminator
<220> FEATURE:
<221> NAME/KEY: primer
<222> LOCATION: (522)..(546)
<223> OTHER INFORMATION: HiNK795
<220> FEATURE:
<221> NAME/KEY: stem_loop
<222> LOCATION: (528)..(810)
<223> OTHER INFORMATION: AGL20 fragment (second strand)
<220> FEATURE:
<221> NAME/KEY: primer
<222> LOCATION: (789)..(816)
<223> OTHER INFORMATION: HiNK794
<220> FEATURE:
<221> NAME/KEY: primer
<222> LOCATION: (811)..(832)
<223> OTHER INFORMATION: HiNK529
<220> FEATURE:
<221> NAME/KEY: Intron
<222> LOCATION: (817)..(1009)
<223> OTHER INFORMATION: second intron from the potato ST.LS1 gene
<220> FEATURE:
<221> NAME/KEY: primer
<222> LOCATION: (990)..(1031)
<223> OTHER INFORMATION: HiNK796
<220> FEATURE:
<221> NAME/KEY: primer
<222> LOCATION: (993)..(1031)
<223> OTHER INFORMATION: HiNK793
<220> FEATURE:
<221> NAME/KEY: stem_loop
<222> LOCATION: (1010)..(1292)
<223> OTHER INFORMATION: AGL20 fragment (first strand)
<220> FEATURE:
<221> NAME/KEY: primer
<222> LOCATION: (1274)..(1298)
<223> OTHER INFORMATION: HiNK792
<220> FEATURE:
<221> NAME/KEY: promoter
<222> LOCATION: (1295)..(2657)
<223> OTHER INFORMATION: Arabidopsis UBi3
<220> FEATURE:
<221> NAME/KEY: promoter
<222> LOCATION: (2783)..(3972)
<223> OTHER INFORMATION: SuperMAS
<220> FEATURE:
<221> NAME/KEY: gene
<222> LOCATION: (3985)..(5160)
<223> OTHER INFORMATION: PMI
<220> FEATURE:
<221> NAME/KEY: terminator
<222> LOCATION: (5228)..(5487)
<223> OTHER INFORMATION: Nos
<220> FEATURE:
<221> NAME/KEY: misc_feature
<222> LOCATION: (5715)..(5739)
<223> OTHER INFORMATION: Left T-DNA border

<400> SEQUENCE: 2
gtttacccgc caatatatcc tgtcaaacac tgatagttta aactgaaggc gggaaacgac    60
aatctgatca tgagcggaga attaagggag tcacgttatg accccgccg atgacgcggg    120 acaagccgtt ttacgtttgg aactgacaga accgcaacgc tgcaggaatt ggccgcagcg    180
gccatttaaa tcaattgggc gcgccgaatt cgagctcggt acccggggat cctctagatc    240
atgtttgaca gcttatcatc ggatctagta acatagatga caccgcgcgc gataatttat    300
cctagtttgc gcgctatatt ttgttttcta tcgcgtatta aatgtataat tgcgggactc    360
taatcataaa aacccatctc ataaataacg tcatgcatta catgttaatt attacatgct    420
taacgtaatt caacagaaat tagatgataa tcatcgcaag accggcaaca ggattcaatc    480
```

```
ttaagaaact ttattgccaa atgtttgaac gatctctgca ggtcgacgca tgctgatctc    540
ctgatcatct gctcgttgtt ggcgacgtag cagatctggt gaagaattga gaaccttatc    600
tttcaaccgg acattttctt tgattaagtg cttctcctct tcatacaact tattaatctg    660 ctcttttgtac aatgcattct ttcttgctcg gatactggaa agactttat ctaattgttt    720 ttctaattct tgaagctcat caatggaaca tgcctctaga ccatctccaa gtaatttccg    780
tttagaaagt tcgagacttt ttaacttctt ccgcggacct gcacatcaac aaattttggt    840
catatattag aaaagttata aattaaaata tacacactta taaactacag aaaagcaatt    900
gctatatact acattctttt attttgaaaa aaatatttga aatattatat tactactaat    960
taatgataat tattatatat atatcaaagg tagaagcaga aacttaccta agaagttaaa   1020
aagtctcgaa ctttctaaac ggaaaattact tggagatggt ctagaggcat gttccattga   1080
tgagcttcaa gaattagaaa aacaattaga taaaagtctt tccagtatcc gagcaagaaa   1140
gaatgcattg tacaaagagc agattaataa gttgtatgaa gaggagaagc acttaatcaa   1200
agaaaatgtc cggttgaaag ataaggttct caattcttca ccagatctgc tacgtcgcca   1260
acaacgagca gatgatcagg agatcagcat gcggatccaa agagagagtc gcgagagatt   1320
tgcagagatc gctttaggct ttgggagaga ttgaagagtc agaaaaagac gaaaggatga   1380
attattatct tccacacgaa ggtcttcttt atatcgcaaa ccaaaagccc aaaaccgtct   1440
tttctattaa tgagaataaa atatctttag ccaaaacaaa aaaggaaga tatcagttga   1500 ggattattat cacgaaacta aaggaaggaa tcatatgata cgtgtcatat tttccaccgt   1560 gcgttttttaa aagaccgact caagtagaga catcctatgg tggtggttgg attaggtcat   1620
ccattacatc tgcttcactg acattttctc attttttcttt ttgtatatac ttttcctcaa   1680
ataatttctt tcttttctat agaagaattt aatcaataag gaaaaagttc aaaaaagatt   1740
ctttccatta agactatgtc ttggttaacc caacccatta agaataagca atcataatat   1800
atatagagaa tactaatact atatatgaga ttttttctttt aatttcatgt tgattatgat   1860
agtttatctt cttgatttaa tttatcaata cttggcataa aagattctaa tctactctaa   1920
taaagaaaag aaaaaaaagt atctaccatt gactaattaa aataaggaaa cttatctacc   1980
aaatttgagt atttttttaga acaatctttt tggtttaatt ccaaaactct aaacctaatt   2040
gttgggaaaa aggacctaat ttttaagaaa agttaataat tagaagatct gtatgttttt   2100
tttttgatcc aagtttttat ttcttttctc ttttttttcat gataaaatct atgttttttt   2160
agtctacaat taaagtaatt gttattattt tcttttatctt ttttttgttgt tgttgttaat   2220 tccctttttt ttttttttaac agcaacttct taaaaaaaaa aacagttggg ccttgaattt   2280
atttcaggcc tgcgttatta agcccagata taaactcaaa acaaaaaaaa tgttgaaccg   2340
gaataaaccc gcgagattaa atgccggttt tcaggtaaca tagaagaaga atatatgagg   2400
attgaagaag tattcaagag gcggaacaat tcacaagtcc aagagcttaa atttctcctc   2460
actcttctgc tacagactcg gaactctttc tctttgctaa aataagatgt tcaggatttt   2520
tgttgcccga caattcatgt atctcacact ctctctcttc tctgttctta ctactctgtt   2580
acattaccac caactcaaga cttttcttcca caatggcgtt tatgagactt ggctccaaat   2640
ccggacggat ctctagagtc gaccatggtg atcactgcag gcatgcaagc ttcgtacgtt   2700
aattaattcg aatccggagc ggccgcacgc gtgggcccgt ttaaacctcg agagatctgc   2760
tagcatcgat ggtaccgagc tcgagactag ctacaggcca aattcgctct tagccgtaca   2820
atattactca ccggtgcgat gcccccccatc gtaggtgaag gtggaaatta atgatccatc   2880
```

```
ttgagaccac aggcccacaa cagctaccag tttcctcaag ggtccaccaa aaacgtaagc   2940
gcttacgtac atggtcgata agaaaaggca atttgtagat gttaacatcc aacgtcgctt   3000
tcagggatcc cgaattccaa gcttggaatt cgggatccta caggccaaat tcgctcttag   3060
ccgtacaata ttactcaccg gtgcgatgcc ccccatcgta ggtgaaggtg gaaattaatg   3120
atccatcttg agaccacagg cccacaacag ctaccagttt cctcaagggt ccaccaaaaa   3180
cgtaagcgct tacgtacatg gtcgataaga aaggcaatt tgtagatgtt aacatccaac    3240
gtcgctttca gggatcccga attccaagct tggaattcgg gatcctacag gccaaattcg   3300
ctcttagccg tacaatatta ctcaccggtg cgatccccc atcgtaggtg aaggtggaaa    3360
ttaatgatcc atcttgagac cacaggccca acagctac cagtttcctc aagggtccac     3420
caaaaacgta agcgcttacg tacatggtcg ataagaaaag gcaatttgta gatgttaaca   3480
tccaacgtcg ctttcaggga tcccgaattc aagcttggg ctgcaggtca atcccattgc    3540
ttttgaagca gctcaacatt gatctctttc tcgagggaga ttttcaaat cagtgcgcaa    3600 gacgtgacgt aagtatccga gtcagttttt attttctac taatttggtc gtttatttcg    3660
gcgtgtagga catggcaacc gggcctgaat tcgcgggta ttctgtttct attccaactt    3720
tttcttgatc cgcagccatt aacgactttt gaatagatac gctgacacgc caagcctcgc   3780
tagtcaaaag tgtaccaaac aacgctttac agcaagaacg gaatgcgcgt gacgctcgcg   3840
gtgacgccat ttcgcctttt cagaaatgga taaatagcct tgcttcctat tatatcttcc   3900
caaattacca atacattaca ctagcatctg aatttcataa ccaatctcga tacaccaaat   3960
cgagatctgc agggatcccc gatcatgcaa aaactcatta actcagtgca aaactatgcc   4020
tggggcagca aaacggcgtt gactgaactt tatggtatgg aaaatccgtc cagccagccg   4080
atggccgagc tgtggatggg cgcacatccg aaaagcagtt cacgagtgca gaatgccgcc   4140
ggagatatcg tttcactgcg tgatgtgatt gagagtgata atcgactct gctcggagag    4200 gccgttgcca aacgctttgg cgaactgcct ttcctgttca agtattatg cgcagcacag    4260 ccactctcca ttcaggttca tccaaacaaa cacaattctg aaatcggttt tgccaaagaa   4320
aatgccgcag gtatcccgat ggatgccgcc gagcgtaact ataaagatcc taaccacaag   4380
ccggagctgg ttttgcgct gacgccttc cttgcgatga acgcgtttcg tgaattttcc      4440
gagattgtct ccctactcca gccggtcgca ggtgcacatc cggcgattgc tcactttta    4500 caacagcctg atgccgaacg tttaagcgaa ctgttcgcca gcctgttgaa tatgcagggt   4560
gaagaaaaat cccgcgcgct ggcgatttta aaatcggccc tcgatagcca gcagggtgaa   4620
ccgtggcaaa cgattcgttt aatttctgaa ttttacccgg aagacagcgg tctgttctcc   4680
ccgctattgc tgaatgtggt gaaattgaac cctggcgaag cgatgttcct gttcgctgaa   4740
acaccgcacg cttacctgca aggcgtggcg ctggaagtga tggcaaactc cgataacgtg   4800
ctgcgtgcgg gtctgacgcc taaatacatt gatattccgg aactggttgc caatgtgaaa   4860
ttcgaagcca aaccggctaa ccagttgttg acccagccgg tgaaacaagg tgcagaactg   4920
gacttcccga ttccagtgga tgattttgcc ttctcgctgc atgaccttag tgataaagaa   4980
accaccatta gccagcagag tgccgccatt ttgttctgcg tcgaaggcga tgcaacgttg   5040
tggaaaggtt ctcagcagtt acagcttaaa ccgggtgaat cagcgtttat tgccgccaac   5100
gaatcaccgg tgactgtcaa aggccacggc cgtttagcgc gtgtttacaa caagctgtaa   5160
gagcttactg aaaaaattaa catctcttgc taagctggga gctcgtcgac ggatcgaatt   5220
cctgcagatc gttcaaacat ttggcaataa agtttcttaa gattgaatcc tgttgccggt   5280
```

```
cttgcgatga ttatcatata atttctgttg aattacgtta agcatgtaat aattaacatg   5340
taatgcatga cgttatttat gagatgggtt tttatgatta gagtcccgca attatacatt   5400
taatacgcga tagaaaacaa atatagcgc gcaaactagg ataaattatc gcgcgcggtg    5460
tcatctatgt tactagatcg ggaattgggt accgaattca ctggccgtcg ttttacaacg   5520
tcgtgactgg gaaaaccctg gcgttaccca acttaatcgc cttgcagcac atcccccttt   5580
cgccagctgg cgtaatagcg aagaggcccg caccgatcgc ccttcccaac agttgcgcag   5640
cctgaatggc gaatggcggg cggccagcat ggccgtatcc gcaatgtgtt attaagttgt   5700
ctaagcgtca atttgtttac accacaatat atcctgccac cagccagcca acagctcccc   5760
gaccggcagc tcggcacaaa atcaccactc gatacaggca gcccatcaga attaattctc   5820
atgtttgaca gcttatcatc gactgcacgg tgcaccaatg cttctggcgt caggcagcca   5880
tcggaagctg tggtatggct gtgcaggtcg taaatcactg cataattcgt gtcgctcaag   5940
gcgcactccc gttctggata atgttttttg cgccgacatc ataacggttc tggcaaatat   6000
tctgaaatga gctgttgaca attaatcatc cggctcgtat aatgtgtgga attgtgagcg   6060
gataacaatt tcacacagga aacagaccat gagggaagcg ttgatcgccg aagtatcgac   6120
tcaactatca gaggtagttg gcgtcatcga gcgccatctc gaaccgacgt tgctggccgt   6180
acatttgtac ggctccgcag tggatggcgg cctgaagcca cacagtgata ttgatttgct   6240
ggttacggtg accgtaaggc ttgatgaaac aacgcggcga gctttgatca cgacctttt    6300 ggaaacttcg gcttcccctg gagagagcga gattctccgc gctgtagaag tcaccattgt   6360
tgtgcacgac gacatcattc cgtggcgtta ccagctaag cgcgaactgc aatttggaga    6420
atggcagcgc aatgacattc ttgcaggtat cttcgagcca gccacgatcg acattgatct   6480
ggctatcttg ctgacaaaag caagagaaca tagcgttgcc ttggtaggtc cagcggcgga   6540
ggaactcttt gatccggttc ctgaacagga tctatttgag gcgctaaatg aaaccttaac   6600
gctatggaac tcgccgcccg actgggctgg cgatgagcga aatgtagtgc ttacgttgtc   6660
ccgcatttgg tacagcgcag taaccggcaa aatcgcgccg aaggatgtcg ctgccgactg   6720
ggcaatggag cgcctgccgg cccagtatca gcccgtcata cttgaagcta ggcaggctta   6780
tcttggacaa gaagatcgct tggcctcgcg cgcagatcag ttggaagaat tgttcacta   6840 cgtgaaaggc gagatcacca agtagtcgg caaataaagc tctagtggat ctccgtaccc    6900 ccggggatc tggctcgcgg cggacgcacg acgccgggc gagaccatag gcgatctcct     6960
aaatcaatag tagctgtaac ctcgaagcgt ttcacttgta caacgattg agaatttttg    7020 tcataaaatt gaaatacttg gttcgcattt ttgtcatccg cggtcagccg caattctgac   7080
gaactgccca tttagctgga gatgattgta catccttcac gtgaaaattt ctcaagcgct   7140
gtgaacaagg gttcagattt tagattgaaa ggtgagccgt tgaaacacgt tcttcttgtc   7200
gatgacgacg tcgctatgcg gcatcttatt attgaatacc ttacgatcca cgccttcaaa   7260
gtgaccgcgg tagccgacag cacccagttc acaagagtac tctcttccgc gacggtcgat   7320
gtcgtggttg ttgatctaaa tttaggtcgt gaagatgggc tcgagatcgt tcgtaatctg   7380
gcggcaaagt ctgatattcc aatcataatt atcagtggcg accgccttga ggagacggat   7440
aaagttgttg cactcgagct aggagcaagt gattttatcg ctaagccgtt cagtatcaga   7500
gagtttctag cacgcattcg ggttgccttg cgcgtgcgcc ccaacgttgt ccgctccaaa   7560
gaccgacggt cttttgtttt tactgactgg acacttaatc tcaggcaacg tcgcttgatg   7620
tccgaagctg gcggtgaggt gaaacttacg gcaggtgagt tcaatcttct cctcgcgttt   7680
```

```
ttagagaaac cccgcgacgt tctatcgcgc gagcaacttc tcattgccag tcgagtacgc   7740
gacgaggagg tttatgacag gagtatagat gttctcattt tgaggctgcg ccgcaaactt   7800
gaggcagatc cgtcaagccc tcaactgata aaaacagcaa gaggtgccgg ttatttcttt   7860
gacgcggacg tgcaggtttc gcacgggggg acgatggcag cctgagccaa ttcccagatc   7920
cccgaggaat cggcgtgagc ggtcgcaaac catccggccc ggtacaaatc ggcgcggcgc   7980
tgggtgatga cctggtggag aagttgaagg ccgcgcaggc cgcccagcgg caacgcatcg   8040
aggcagaagc acgccccggt gaatcgtggc aagcggccgc tgatcgaatc cgcaaagaat   8100
cccggcaacc gccggcagcc ggtgcgccgt cgattaggaa gccgcccaag ggcgacgagc   8160
aaccagattt tttcgttccg atgctctatg acgtgggcac ccgcgatagt cgcagcatca   8220
tggacgtggc cgttttccgt ctgtcgaagc gtgaccgacg agctggcgag gtgatccgct   8280
acgagcttcc agacgggcac gtagaggttt ccgcagggcc ggccggcatg ccagtgtgt   8340 gggattacga cctggtactg atggcggttt cccatctaac cgaatccatg aaccgatacc   8400
gggaagggaa gggagacaag cccggccgcg tgttccgtcc acacgttgcg gacgtactca   8460
agttctgccg gcgagccgat ggcggaaagc agaaagacga cctggtagaa acctgcattc   8520
ggttaaacac cacgcacgtt gccatgcagc gtacgaagaa ggccaagaac ggccgcctgg   8580
tgacggtatc cgagggtgaa gccttgatta gccgctacaa gatcgtaaag agcgaaaccg   8640
ggcggccgga gtacatcgag atcgagctag ctgattggat gtaccgcgag atcacagaag   8700
gcaagaaccc ggacgtgctg acggttcacc ccgattactt tttgatcgat cccggcatcg   8760
gccgttttct ctaccgcctg gcacgccgcg ccgcaggcaa ggcagaagcc agatggttgt   8820
tcaagacgat ctacgaacgc agtggcagcg ccggagagtt caagaagttc tgtttcaccg   8880
tgcgcaagct gatcgggtca aatgacctgc cggagtacga tttgaaggag gaggcggggc   8940
aggctggccc gatcctagtc atgcgctacc gcaacctgat cgaggcgaa gcatccgccg   9000 gttcctaatg tacggagcag atgctagggc aaattgccct agcagggaa aaaggtcgaa   9060 aaggtctctt tcctgtggat agcacgtaca ttgggaaccc aaagccgtac attgggaacc   9120
ggaacccgta cattgggaac ccaaagccgt acattgggaa ccggtcacac atgtaagtga   9180
ctgatataaa agagaaaaaa ggcgattttt ccgcctaaaa ctctttaaaa cttattaaaa   9240
ctcttaaaac ccgcctggcc tgtgcataac tgtctggcca gcgcacagcc gaagagctgc   9300
aaaaagcgcc tacccttcgg tcgctgcgct ccctacgccc cgccgcttcg cgtcggccta   9360
tcgcggccgc tggccgctca aaaatggctg gcctacggcc aggcaatcta ccagggcgcg   9420
gacaagccgc gccgtcgcca ctcgaccgcc ggcgctgagg tctgcctcgt gaagaaggtg   9480
ttgctgactc ataccaggcc tgaatcgccc catcatccag ccagaaagtg agggagccac   9540
ggttgatgag agctttgttg taggtggacc agttggtgat tttgaacttt tgctttgcca   9600
cggaacggtc tgcgttgtcg ggaagatgcg tgatctgatc cttcaactca gcaaaagttc   9660
gatttattca acaaagccgc cgtcccgtca agtcagcgta atgctctgcc agtgttacaa   9720
ccaattaacc aattctgatt agaaaaactc atcgagcatc aaatgaaact gcaatttatt   9780
catatcagga ttatcaatac catattttg aaaaagccgt ttctgtaatg aaggagaaaa   9840
ctcaccgagg cagttccata ggatggcaag atcctggtat cggtctgcga ttccgactcg   9900
tccaacatca atacaaccta ttaatttccc ctcgtcaaaa ataaggttat caagtgagaa   9960
atcaccatga gtgacgactg aatccggtga gaatggcaaa agctctgcat taatgaatcg  10020
gccaacgcgc ggggagaggc ggtttgcgta ttgggcgctc ttccgcttcc tcgctcactg  10080
```

```
actcgctgcg ctcggtcgtt cggctgcggc gagcggtatc agctcactca aaggcggtaa    10140
tacggttatc cacagaatca ggggataacg caggaaagaa catgtgagca aaaggccagc    10200
aaaaggccag gaaccgtaaa aaggccgcgt tgctggcgtt tttccatagg ctccgccccc    10260
ctgacgagca tcacaaaaat cgacgctcaa gtcagaggtg gcgaaacccg acaggactat    10320
aaagatacca ggcgtttccc cctggaagct ccctcgtgcg ctctcctgtt ccgaccctgc    10380
cgcttaccgg atacctgtcc gcctttctcc cttcgggaag cgtggcgctt tctcatagct    10440
cacgctgtag gtatctcagt tcggtgtagg tcgttcgctc caagctgggc tgtgtgcacg    10500
aaccccccgt tcagcccgac cgctgcgcct tatccggtaa ctatcgtctt gagtccaacc    10560
cggtaagaca cgacttatcg ccactggcag cagccactgg taacaggatt agcagagcga    10620
ggtatgtagg cggtgctaca gagttcttga agtggtggcc taactacggc tacactaaa    10680 gaacagtatt tggtatctgc gctctgctga agccagttac cttcggaaaa agagttggta    10740
gctcttgatc cggcaaacaa accaccgctg gtagcggtgg ttttttttgtt tgcaagcagc    10800 agattacgcg cagaaaaaaa ggatctcaag aagatccttt gatcttttct acggggtctg    10860
acgctcagtg gaacgaaaac tcacgttaag ggattttggt catgagatta tcaaaaagga    10920
tcttcaccta gatccttttg atccggaatt aattcctgtg gttggcatgc acatacaaat    10980
ggacgaacgg ataaaccttt tcacgccctt taaatatccc gattattcta ataaacgctc    11040
ttttctctta g                                                         11051

<210> SEQ ID NO 3
<211> LENGTH: 859
<212> TYPE: DNA
<213> ORGANISM: Arabidopsis
<220> FEATURE:
<221> NAME/KEY: misc_feature
<222> LOCATION: (1)..(859)
<223> OTHER INFORMATION: FLC cDNA fragment

<400> SEQUENCE: 3
atgggaagaa agaaattaga aatcaagcga attgagaaca aaagtagccg acaagtcacc      60
ttctccaaac gtcgcaacgg tctcatcgag aaagctcgtc agctttctgt tctctgtgac     120
gcatccgtcg ctcttctcgt cgtctccgcc tccggcaagc tctacagctt ctcctccggc     180
gataacctgg tcaagatcct tgatcgatat gggaaacagc atgctgatga tcttaaagcc     240
ttggatcatc agtcaaaagc tctgaactat ggttcacact atgagctact tgaacttgtg     300
gatagcaagc ttgtgggatc aaatgtcaaa aatgtgagta tcgatgctct tgttcaactg     360
gaggaacacc ttgagactgc cctctccgtg actagagcca agaagaccga actcatgttg     420
aagcttgttg tgaatcttaa agaaaaggag aaaatgctga agaagagaa ccaggttttg     480 gctagccaga tggagaataa tcatcatgtg ggagcagaag ctgagatgga gatgtcacct     540
gctggacaaa tctccgacaa tcttccggtg actctcccac tacttaatta accaccttaa     600
atcggcggtt gaaatcaaaa tccaaaacat atataattat gaagaaaaaa aaataagata     660
tgtaattatt ccgctgataa gggcgagcgt atgtatatct taatactctc tctttggcca     720
agagactttg tgtgtgatac ttaagtagac ggaactaagt caatactatc tgttttaaga     780
caaaaggttg atgaactttg taccttattc gtgtgagaat tgcatcgaga tcttgagtgt     840
aaaaaaaaaa aaaaaaaaa                                                   859

<210> SEQ ID NO 4
<211> LENGTH: 4818
```

```
<212> TYPE: DNA
<213> ORGANISM: sugar beet
<220> FEATURE:
<221> NAME/KEY: misc_feature
<222> LOCATION: (1)..(4818)
<223> OTHER INFORMATION: AGL20 partial gene
<220> FEATURE:
<221> NAME/KEY: misc_feature
<222> LOCATION: (1)..(84)
<223> OTHER INFORMATION: Exon2
<220> FEATURE:
<221> NAME/KEY: misc_feature
<222> LOCATION: (2518)..(2578)
<223> OTHER INFORMATION: Exon3
<220> FEATURE:
<221> NAME/KEY: misc_feature
<222> LOCATION: (2671)..(2770)
<223> OTHER INFORMATION: Exon4
<220> FEATURE:
<221> NAME/KEY: misc_feature
<222> LOCATION: (2951)..(2992)
<223> OTHER INFORMATION: Exon5
<220> FEATURE:
<221> NAME/KEY: misc_feature
<222> LOCATION: (3183)..(3224)
<223> OTHER INFORMATION: Exon6
<220> FEATURE:
<221> NAME/KEY: misc_feature
<222> LOCATION: (4789)..(4818)
<223> OTHER INFORMATION: Exon7

<400> SEQUENCE: 4
actaagacaa ttgatcggta ccaaaagcat atgaaggatc tgcgtggagt gaaaagtaaa      60
gtgttggatc aaaaaaattt gctggtaaat ttctattcat tgtttatata aaaaggtaga     120
atataattat attatatact tttcgattca taagcaagtc tgaattatat tcttcatata     180
tttcactgga atttaaattc ttttttttat gaataagcag accaacatgt caatcctttt     240
caagataatt aattaggtaa ttaggtgtcg atgtcatcta acttagtttg ttaaacctcg     300
aggtagtttt taagacttca atggaaaaaa gagaccgtaa cttagtttga aacaagatat     360
gtcatctaac ttggttgcta acattggata gtttttatga cttaaaaagg aaaaaagaga     420
atgtaagtag tagcgtgcaa attgaaggta cagtaagcat aagcattgtt atgcatataa     480
actaatcgta tataaatcta attggtacca gatttggtct taatattgta ttaatgaagt     540
gcaagaaaag caacaatctc atgttgttta tgttgaatat tgttgttgtc tcatgttgct     600
cctgctagct taggaagact cagatgcacc ttttctttat tttcttactt tgtaaataac     660
acttgcaatt ttaagcatgg taaattggga ctagggtttt aaagtattga tcatgagtcg     720
ggttggacca tatatcatcg gtcaagttag gttatgtaag cgacatacca ataaaatagc     780
ttgaccattt caaaataggt tgtaagtttc atcaatcggg tccatatctt ctgtgatatt     840
acttactatc tcaatataat tactattcac tataatttta caaatcatcg aaaaaataaa     900
tgttattatg taaaataaaa ttggattcgt gctagtttat attgaaatta tcaactttgc     960
gtagttattg taaatagatc gtaaaaatat taatagtcaa aatgaaacaa cgacgaacat    1020
gatatgaggg agtgctagat actagatgca ggggcggatt caggattctg gaccaggagt    1080
agcgcaactt tacattacta gaaactcaaa aaaaaaagtt cgtaattact aaattcaaat    1140
gttacaaaat cctaaatgtt acaaatcaat catatatcac taccaaattt ccacaaattc    1200
aacccaatta acaatcatac ttcacaacaa tcaatcaaat ttccacaaat tcaacccaat    1260
taacaatcat acattcatac ttcacaacaa tcaatcaaat ttctacaaat tcaacccaat    1320
taacaatcat acattcatac ttcacaacaa tcaatcaaat ttccacaaat tcagcccaac    1380
taacaatgaa aaaaacgaca acaaccaatc aaaatttaac ctcaatcaaa atttcaaccc    1440
```

```
aatacccaat aacaaataac aatcatactt cagtatttca caacaatgaa caatcaaatt    1500
ccacagacca caaattcagc ctaactctta acaaacaata aaaaatctgc caactagtaa    1560
ttccacataa cacatacaca tttaactctt aactaacaat gaaaaatctg ccaaataaca    1620
atcttagagg aaagcaaaag aaagttacct gaacggaagt acggaagacg gaatgtctgt    1680
agccctgaac gccggaactc gaaaggccga accgccgctg tgtcgccact tgctgtctcg    1740
ccgaccaatt tacacgaaaa ctgcgtctgc cattagagtc tagagagccg agaagaaaga    1800
aaaataaggt taagagaaga ctcaaattta gggctagatc tagattacaa ttcgcggaaa    1860
agtaaactta ccattttctc ggacctcggt ttctccgacg cgaagacgat cgaaactgaa    1920
gagttgagaa aaaacactcc ggcgagactc gattttccga cgacttgaga gtttgagact    1980
tgagagagag agagagagag aggggacttg agacttgaga gagcgaaatt cccaaatgaa    2040
acacgctgct gaattttttt gcgatttttg gcgattttt gaatttttt ttttttttaa     2100 aagcaggggt agcacgtgct accccttgtt accacgtggc tccgccatga gtatctcaag    2160
cagttaaaga aagtattata ctacaggtga gaacttttgg aagagtggaa aggccaatca    2220
actgcaagtg aatctgtatg gtgtatccaa gaccttgata tatatattca gaactccaca    2280
acaaaatata cttcctccgt tttgttttta atgcaataaa gaggtattat tgtgagata     2340 taaaatattc atttgttgca tttaaaacga aaccgaggaa gtatgaattt ataagaattt    2400
cccggaatca ttgagtggag tttctatatg tccctgaata tctcaatctg tgtaactgca    2460
tgcattagca ctttagcagc atttgtcaac ttacagaatc cgtattttc atgcagcaat     2520 tcaaggatga tactattgag cttgagaaga agttaaaaag tctcgaactt tctaaacggt    2580
taggcaattc aatcaactaa ttgaatcatg catgttctag ctagctagct aactcttcta    2640
caacttatgc atgtttttat gggtttctag gaaattactt ggagatggtc tagaggcatg    2700
ttccattgat gagcttcaag aattagaaaa acaattagat aaaagtcttt ccagtatccg    2760
agcaagaaag gtacataatc ttatctgaat ttattggcgc ttatctaaat taaaataaac    2820
ttgtttagaa cttacctgtt gttatttatg cgaacttatt tgtcttaaag cttattttt    2880 aaggtgaaca gaataaatgc tacatgcata tctgatctgg tttaaccaat ttactactgt    2940
tttctcccag aatgcattgt acaaagagca gattaataag ttgtatgaag aggtaagata    3000
aattcacaag ttttactgca caagttgatt gttttttaggt tattgaacga gctcagatta   3060 atgcatacg tcatttacct tcttttatag ttgcatgttt tcaaagactt catttgttgt    3120
agtacttatt ttaaatatta gacgtttgct tatttttcc gttatatatt ttggatccgt     3180
aggagaagca cttaatcaaa gaaaatgtcc ggttgaaaga taaggtaagt agtttcatat    3240
catacgttgc ctaattgttt ttttttcttat aggctccgtt tcgtagggcg taaaacgttt    3300
tcccggaaaa ctgttttcct ctattttcag ttttacattg tttggttagc aaaagagtgt    3360
aaaaccattt tcccttgggt taaatttact ctcccaatga tggaaaacca ttttcctttc    3420
aaaatgaagg gaaaactatt ttccttatct ctcttgtaca ctcttctcac tacctcctta    3480
ctttcccttt catttttcctt tgacttcatc attttttatta catcgaacca aacaacggaa   3540
aactaatttt ggaattgtgt tttccattgt aaattatttt ccatgaaaat cattttacac    3600
tgaaaatgtt ttacgcccta ccaaacggag tcatagtgta agtattcctg gattgttgca    3660
tgtcctacat ttggcgagta acggacaacc gttatgatca ttttattcgc aatattgatt    3720
tgatgcggaa gtatgctttt gatagaagac aaaacatgtg attttgtgtt gaattggagt    3780
acatggcaac tactttagtt ggtaaaatct tatgagatga agtccataag gcttgaaatt    3840
```

```
gaatctcgtt catattttg tggttatata cgcactcaaa agaagtgaat ctatatatta    3900
aactaaatga tggtagatga gaatgccttt taataataat aggttatatg taattagagg    3960
tcattctata taattgattt ataataaata tgagtatctt tcgatatttc tgcttctatt    4020
tccccatgcc acaagtagta gtctttatca gaaaatttcg taaaaattat atgaggaagc    4080
atataccaag tagtacttga tatagtgaaa gaaataatct aacaatctta agattgtgag    4140
ataaagccct agtaatggta ctaggaattc cccttacttt accccctact tttatttaa      4200 aggggccttg cctgataagc tgaattgggt cgacctatga aaggttttgg tttcctaggg    4260
attagggcac ttcttttac catatatata aataaaaaa aagagggagc gtaagtggac        4320
tagtacatta ggatgatcaa gtttagtata aatcatacct aaagatagta tagaaattaa    4380
ggttttgttc acttatgtta aacacacgtt ttttcatgag ctattgtagt attgtatcaa    4440
tgtatctcat gatgttgccc tataattaca acatgtactt gattctcttt ccaaaagtat    4500
acaataagat gtggttcatc tcataatata ggggaatata atgatgatgc tcttttattc    4560
gatcaacttt gatatgtatt tgttagtttc gatttctata atgtatgatt ttgtattata    4620 atttaattt atttaaaatg ttgcgcattt aacttagaaa aaaacttgtg ttgtaaataa      4680
agtatccatc ataacacata tctggataca tactctgtgc atgaatgttt tataccctac    4740
aaataatagc gaaattctaa tgggtgattg ctaaatccaa cttctcaggt tctcaattct    4800
tcaccagatc tgctacct                                                   4818

<210> SEQ ID NO 5
<211> LENGTH: 283
<212> TYPE: DNA
<213> ORGANISM: Sugar beet
<220> FEATURE:
<221> NAME/KEY: misc_feature
<222> LOCATION: (1)..(283)
<223> OTHER INFORMATION: BvAGL20 repeat fragment, first and/or second
      strand

<400> SEQUENCE: 5
aagaagttaa aaagtctcga actttctaaa cggaaattac ttggagatgg tctagaggca      60
tgttccattg atgagcttca agaattagaa aaacaattag ataaaagtct ttccagtatc    120
cgagcaagaa agaatgcatt gtacaaagag cagattaata agttgtatga agaggagaag    180
cacttaatca agaaaaatgt ccggttgaaa gataaggttc tcaattcttc accagatctg    240
ctacgtcgcc aacaacgagc agatgatcag gagatcagca tgc                      283

<210> SEQ ID NO 6
<211> LENGTH: 611
<212> TYPE: DNA
<213> ORGANISM: Sugar beet
<220> FEATURE:
<221> NAME/KEY: misc_feature
<222> LOCATION: (1)..(611)
<223> OTHER INFORMATION: BvAGL20 cDNA fragment
<220> FEATURE:
<221> NAME/KEY: primer
<222> LOCATION: (1)..(25)
<223> OTHER INFORMATION: HiNK624
<220> FEATURE:
<221> NAME/KEY: primer
<222> LOCATION: (585)..(611)
<223> OTHER INFORMATION: HiNK619

<400> SEQUENCE: 6
atggtkmgrg gnaaracnca gatgaagaga attgaaaatg attcaagcag acaagtgact      60
```

```
tcctcaaaaa gaagaaatgg gttgttgaag aaagcttttg agctttcagt tctttgtgat    120
gctgaagttg cacttatcat tttttctcct tctggaaaac tctatgaatt cgcaagctca    180
agtacgacta agacaattga tcggtaccaa aagcatatga aggatctgcg tggagtgaaa    240
agtaaagtgt tggatcaaaa aaatttgctg caattcaagg atgatactat tgagcttgag    300
aagaagttaa aaagtctcga actttctaaa cggaaattac ttggagatgg tctagaggca    360
tgttccattg atgagcttca agaattagaa aaacaattcg ataaaggtct ttccagtctc    420
cgagcaagaa agaatgcatt gtacaaagag cagattaata agttgtatga agaggacaag    480
cacttaatca agaaaatgt ccggttgaaa gataaggttc tcaattcttc accagatctg    540
ctacctcgcc aacaacgagc agatgatcag gagatcagca tgcaagawgt ngagacnsaa    600
ytgttcatyg g                                                         611

<210> SEQ ID NO 7
<211> LENGTH: 22
<212> TYPE: DNA
<213> ORGANISM: Artificial
<220> FEATURE:
<223> OTHER INFORMATION: HiNK529 primer

<400> SEQUENCE: 7
ccgcggacct gcacatcaac aa                                              22

<210> SEQ ID NO 8
<211> LENGTH: 25
<212> TYPE: DNA
<213> ORGANISM: Artificial
<220> FEATURE:
<223> OTHER INFORMATION: HiNK792 primer

<400> SEQUENCE: 8
gatcaggaga tcagcatgcg gatcc                                           25

<210> SEQ ID NO 9
<211> LENGTH: 39
<212> TYPE: DNA
<213> ORGANISM: Artificial
<220> FEATURE:
<223> OTHER INFORMATION: HiNK793 primer

<400> SEQUENCE: 9
gaagcagaaa cttacctaag aagttaaaaa gtctcgaac                            39

<210> SEQ ID NO 10
<211> LENGTH: 28
<212> TYPE: DNA
<213> ORGANISM: Artificial
<220> FEATURE:
<223> OTHER INFORMATION: HiNK794 primer

<400> SEQUENCE: 10
gttcgagact ttttaacttc ttccgcgg                                        28

<210> SEQ ID NO 11
<211> LENGTH: 25
<212> TYPE: DNA
<213> ORGANISM: Artificial
<220> FEATURE:
<223> OTHER INFORMATION: HiNK795 primer

<400> SEQUENCE: 11
gtcgacgcat gctgatctcc tgatc                                           25
```

```
<210> SEQ ID NO 12
<211> LENGTH: 42
<212> TYPE: DNA
<213> ORGANISM: Artificial
<220> FEATURE:
<223> OTHER INFORMATION: HiNK796 primer

<400> SEQUENCE: 12
gtagaagcag aaacttacct aagaagttaa aaagtctcga ac                              42

<210> SEQ ID NO 13
<211> LENGTH: 25
<212> TYPE: DNA
<213> ORGANISM: Artificial
<220> FEATURE:
<223> OTHER INFORMATION: HiNK624 primer
<220> FEATURE:
<221> NAME/KEY: misc_feature
<222> LOCATION: (6)..(6)
<223> OTHER INFORMATION: k= G or T
<220> FEATURE:
<221> NAME/KEY: misc_feature
<222> LOCATION: (7)..(7)
<223> OTHER INFORMATION: m = A or C
<220> FEATURE:
<221> NAME/KEY: misc_feature
<222> LOCATION: (9)..(9)
<223> OTHER INFORMATION: r = A or G
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: r = A or G
<220> FEATURE:
<221> NAME/KEY: misc_feature
<222> LOCATION: (18)..(18)
<223> OTHER INFORMATION: n is a, c, g, or t

<400> SEQUENCE: 13
atggtkmgrg gnaaracnca gatga                                                 25

<210> SEQ ID NO 14
<211> LENGTH: 26
<212> TYPE: DNA
<213> ORGANISM: Artificial
<220> FEATURE:
<223> OTHER INFORMATION: HiNK619 primer
<220> FEATURE:
<221> NAME/KEY: misc_feature
<222> LOCATION: (3)..(3)
<223> OTHER INFORMATION: r = A or G
<220> FEATURE:
<221> NAME/KEY: misc_feature
<222> LOCATION: (11)..(11)
<223> OTHER INFORMATION: r = A or G
<220> FEATURE:
<221> NAME/KEY: misc_feature
<222> LOCATION: (14)..(14)
<223> OTHER INFORMATION: s = C or G
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: w = A or T
```

```
<400> SEQUENCE: 14
ccratgaaca rttsngtctc nacwtc                                          26

<210> SEQ ID NO 15
<211> LENGTH: 28
<212> TYPE: DNA
<213> ORGANISM: Artificial
<220> FEATURE:
<223> OTHER INFORMATION: HiNK725 primer

<400> SEQUENCE: 15
actaagacaa ttgatcggta ccaaaagc                                        28

<210> SEQ ID NO 16
<211> LENGTH: 28
<212> TYPE: DNA
<213> ORGANISM: Artificial
<220> FEATURE:
<223> OTHER INFORMATION: HiNK729 primer

<400> SEQUENCE: 16
aaggtagcag atctggtgaa gaattgag                                        28

<210> SEQ ID NO 17
<211> LENGTH: 33
<212> TYPE: DNA
<213> ORGANISM: Artificial
<220> FEATURE:
<223> OTHER INFORMATION: HiNK2617 Primer

<400> SEQUENCE: 17
taaatggatc caagaagtta aaaagtctcg aac                                  33

<210> SEQ ID NO 18
<211> LENGTH: 45
<212> TYPE: DNA
<213> ORGANISM: Artificial
<220> FEATURE:
<223> OTHER INFORMATION: HiNK2618 primer

<400> SEQUENCE: 18
gaagcagaaa cttacctgtc gacaagaagt taaaaagtct cgaac                     45

<210> SEQ ID NO 19
<211> LENGTH: 10569
<212> TYPE: DNA
<213> ORGANISM: Artificial
<220> FEATURE:
<223> OTHER INFORMATION: pHiNK440
<220> FEATURE:
<221> NAME/KEY: pHiNK440
<222> LOCATION: (1)..(10569)
<220> FEATURE:
<221> NAME/KEY: terminator
<222> LOCATION: (233)..(527)
<223> OTHER INFORMATION: Nos
<220> FEATURE:
<221> NAME/KEY: primer
<222> LOCATION: (522)..(546)
<223> OTHER INFORMATION: HiNK795
<220> FEATURE:
<221> NAME/KEY: repeat_unit
<222> LOCATION: (528)..(810)
<223> OTHER INFORMATION: AGL20 cDNA fragment in sense orientation
<220> FEATURE:
<221> NAME/KEY: primer
<222> LOCATION: (789)..(816)
<223> OTHER INFORMATION: HiNK2617
<220> FEATURE:
<221> NAME/KEY: promoter
```

<222> LOCATION: (817)..(2169)
<223> OTHER INFORMATION: Arabidopsis Ubi3

<400> SEQUENCE: 19

```
gtttacccgc caatatatcc tgtcaaacac tgatagttta aactgaaggc gggaaacgac      60
aatctgatca tgagcggaga attaagggag tcacgttatg accccgccg atgacgcggg     120
acaagccgtt ttacgtttgg aactgacaga accgcaacgc tgcaggaatt ggccgcagcg    180
gccatttaaa tcaattgggc gcgccgaatt cgagctcggt acccggggat cctctagatc    240
atgtttgaca gcttatcatc ggatctagta acatagatga caccgcgcgc gataatttat    300
cctagtttgc gcgctatatt ttgttttcta tcgcgtatta aatgtataat tgcgggactc    360
taatcataaa aacccatctc ataaataacg tcatgcatta catgttaatt attacatgct    420
taacgtaatt caacagaaat tagatgataa tcatcgcaag accggcaaca ggattcaatc    480
ttaagaaact ttattgccaa atgtttgaac gatctctgca ggtcgacgca tgctgatctc    540
ctgatcatct gctcgttgtt ggcgacgtag cagatctggt gaagaattga gaaccttatc    600
tttcaaccgg acattttctt tgattaagtg cttctcctct tcatacaact tattaatctg    660
ctctttgtac aatgcattct ttcttgctcg gatactggaa agactttttat ctaattgttt    720
ttctaattct tgaagctcat caatggaaca tgcctctaga ccatctccaa gtaatttccg    780
tttagaaagt tcgagacttt taacttcctt ggatccaaag agagtcgc gagagatttg      840
cagagatcgc tttaggcttt gggagagatt gaagagtcag aaaagacga aggatgaat      900
tattatcttc cacacgaagg tcttctttat atcgcaaacc aaaagcccaa aaccgtcttt    960
tctattaatg agaataaaat atctttagcc aaaacaaaaa aaggaagata tcagttgagg   1020
attattatca cgaaactaaa ggaaggaatc atatgatacg tgtcatattt tccaccgtgc   1080
gtttttaaaa gaccgactca agtagagaca tcctatggtg gtggttggat taggtcatcc   1140
attacatctg cttcactgac attttttctat tttcttttt gtatatactt ttcctcaaat   1200
aatttctttc ttttctatag aagaatttaa tcaataagga aaaagttcaa aaagattct    1260
ttccattaag actatgtctt ggttaaccca acccattaag aataagcaat cataatatat   1320
atagagaata ctaatactat atatgagatt ttttctttaa tttcatgttg attatgatag   1380
tttatcttct tgatttaatt tatcaatact tggcataaaa gattctaatc tactctaata   1440
aagaaaagaa aaaaagtat ctaccattga ctaattaaaa taaggaaact tatctaccaa    1500
atttgagtat tttttagaac aatcttttttg gtttaattcc aaaactctaa acctaattgt  1560
tgggaaaaag gacctaattt ttaagaaaag ttaataatta gaagatctgt atgtttttt    1620
tttgatccaa gttttatttt cttttctctt tttttcatga taaaatctat gttttttag    1680
tctacaatta aagtaattgt tattattttc tttatcttt tttgttgttg ttgttaattc    1740
ccttttttttt tttttaacag caacttctta aaaaaaaaa cagttgggcc ttgaatttat   1800
tcaggcctg cgttattaag cccagataat aactcaaaac aaaaaaatg ttgaaccgga     1860
ataaacccgc gagattaaat gccggttttc aggtaacata gaagaagaat atatgaggat   1920
tgaagaagta ttcaagaggc ggaacaattc acaagtccaa gagcttaaat ttctcctcac   1980
tcttctgcta cagactcgga actctttctc tttgctaaaa taagatgttc aggattttg    2040
ttgcccgaca attcatgtat ctcacactct ctctcttctc tgttcttact actctgttac   2100
attaccacca actcaagact ttcttccaca atggcgttta tgagacttgg ctccaaatcc   2160
ggacggatct ctagagtcga ccatggtgat cactgcaggc atgcaagctt cgtacgttaa   2220
ttaattcgaa tccggagcgg ccgcacgcgt gggcccgttt aaacctcgag agatctgcta   2280
```

```
gcatcgatgg taccgagctc gagactagct acaggccaaa ttcgctctta gccgtacaat    2340
attactcacc ggtgcgatgc cccccatcgt aggtgaaggt ggaaattaat gatccatctt    2400
gagaccacag gcccacaaca gctaccagtt tcctcaaggg tccaccaaaa acgtaagcgc    2460
ttacgtacat ggtcgataag aaaaggcaat tgtagatgt taacatccaa cgtcgctttc     2520
agggatcccg aattccaagc ttggaattcg gatcctaca ggccaaattc gctcttagcc     2580
gtacaatatt actcaccggt gcgatgcccc catcgtagg tgaaggtgga aattaatgat     2640
ccatcttgag accacaggcc cacaacagct accagtttcc tcaagggtcc accaaaaacg    2700
taagcgctta cgtacatggt cgataagaaa aggcaatttg tagatgttaa catccaacgt    2760
cgctttcagg gatcccgaat tccaagcttg aattcggga tcctacaggc caaattcgct     2820
cttagccgta caatattact caccggtgcg atccccccat cgtaggtgaa ggtggaaatt    2880
aatgatccat cttgagacca caggcccaca acagctacca gtttcctcaa gggtccacca    2940
aaaacgtaag cgcttacgta catggtcgat aagaaaaggc aatttgtaga tgttaacatc    3000
caacgtcgct ttcagggatc ccgaattcca agcttgggct gcaggtcaat cccattgctt    3060
ttgaagcagc tcaacattga tctctttctc gagggagatt tttcaaatca gtgcgcaaga    3120
cgtgacgtaa gtatccgagt cagtttttat ttttctacta atttggtcgt ttatttcggc    3180
gtgtaggaca tggcaaccgg gcctgaattt cgcgggtatt ctgtttctat tccaactttt    3240
tcttgatccg cagccattaa cgacttttga atagatacgc tgacacgcca agcctcgcta    3300
gtcaaaagtg taccaaacaa cgcttttacag caagaacgga atgcgcgtga cgctcgcggt    3360
gacgccattt cgccttttca gaaatggata atagccttg cttcctatta tatcttccca     3420
aattaccaat acattacact agcatctgaa tttcataacc aatctcgata caccaaatcg    3480
agatctgcag ggatccccga tcatgcaaaa actcattaac tcagtgcaaa actatgcctg    3540
gggcagcaaa acggcgttga ctgaacttta tggtatggaa atccgtcca gccagccgat     3600 ggccgagctg tggatgggcg cacatccgaa aagcagttca cgagtgcaga atgccgccgg    3660
agatatcgtt tcactgcgtg atgtgattga gagtgataaa tcgactctgc tcggagaggc    3720
cgttgccaaa cgctttggcg aactgccttt cctgttcaaa gtattatgcg cagcacagcc    3780
actctccatt caggttcatc caaacaaaca caattctgaa atcggttttg ccaaagaaaa    3840
tgccgcaggt atcccgatgg atgccgccga gcgtaactat aaagatccta accacaagcc    3900
ggagctggtt tttgcgctga cgcctttcct tgcgatgaac gcgttcgtg aattttccga     3960 gattgtctcc ctactccagc cggtcgcagg tgcacatccg gcgattgctc acttttttaca    4020 acagcctgat gccgaacgtt taagcgaact gttcgccagc ctgttgaata tgcagggtga    4080
agaaaaatcc cgcgcgctgg cgattttaaa atcggccctc gatagccagc agggtgaacc    4140
gtggcaaacg attcgtttaa tttctgaatt ttacccggaa gacagcggtc tgttctcccc    4200
gctattgctg aatgtggtga aattgaaccc tggcgaagcg atgttcctgt tcgctgaaac    4260
accgcacgct tacctgcaag gcgtggcgct ggaagtgatg gcaaactccg ataacgtgct    4320
gcgtgcgggt ctgacgccta atacattga tattccggaa ctggttgcca atgtgaaatt     4380
cgaagccaaa ccggctaacc agttgttgac ccagccggtg aaacaaggtg cagaactgga    4440
cttcccgatt ccagtggatg attttgcctt ctcgctgcat gaccttagtg ataaagaaac    4500
caccattagc cagcagagtg ccgccatttt gttctgcgtc gaaggcgatg caacgttgtg    4560
gaaaggttct cagcagttac agcttaaacc gggtgaatca gcgttattg ccgccaacga     4620 atcaccggtg actgtcaaag gccacggccg tttagcgcgt gtttacaaca gctgtaaga    4680
```

```
gcttactgaa aaaattaaca tctcttgcta agctgggagc tcgtcgacgg atcgaattcc    4740
tgcagatcgt tcaaacattt ggcaataaag tttcttaaga ttgaatcctg ttgccggtct    4800
tgcgatgatt atcatataat ttctgttgaa ttacgttaag catgtaataa ttaacatgta    4860
atgcatgacg ttatttatga gatgggtttt tatgattaga gtcccgcaat tatacattta    4920
atacgcgata gaaaacaaaa tatagcgcgc aaactaggat aaattatcgc gcgcggtgtc    4980
atctatgtta ctagatcggg aattgggtac cgaattcact ggccgtcgtt ttacaacgtc    5040
gtgactggga aaaccctggc gttacccaac ttaatcgcct tgcagcacat ccccctttcg    5100
ccagctggcg taatagcgaa gaggcccgca ccgatcgccc ttcccaacag ttgcgcagcc    5160
tgaatggcga atggcgggcg ccagcatgg ccgtatccgc aatgtgttat taagttgtct    5220
aagcgtcaat ttgtttacac cacaatatat cctgccacca gccagccaac agctccccga    5280
ccggcagctc ggcacaaaat caccactcga tacaggcagc ccatcagaat taattctcat    5340
gtttgacagc ttatcatcga ctgcacggtg caccaatgct tctggcgtca ggcagccatc    5400
ggaagctgtg gtatggctgt gcaggtcgta aatcactgca taattcgtgt cgctcaaggc    5460
gcactcccgt tctggataat gttttttgcg ccgacatcat aacggttctg gcaaatattc    5520
tgaaatgagc tgttgacaat taatcatccg gctcgtataa tgtgtggaat tgtgagcgga    5580
taacaatttc acacaggaaa cagaccatga gggaagcgtt gatcgccgaa gtatcgactc    5640
aactatcaga ggtagttggc gtcatcgagc gccatctcga accgacgttg ctggccgtac    5700
atttgtacgg ctccgcagtg gatggcggcc tgaagccaca cagtgatatt gatttgctgg    5760
ttacggtgac cgtaaggctt gatgaaacaa cgcggcgagc tttgatcaac gaccttttgg    5820
aaacttcggc ttcccctgga gagagcgaga ttctccgcgc tgtagaagtc accattgttg    5880
tgcacgacga catcattccg tggcgttatc cagctaagcg cgaactgcaa tttggagaat    5940
ggcagcgcaa tgacattctt gcaggtatct tcgagccagc cacgatcgac attgatctgg    6000
ctatcttgct gacaaaagca agagaacata gcgttgcctt ggtaggtcca gcggcggagg    6060
aactctttga tccggttcct gaacaggatc tatttgaggc gctaaatgaa accttaacgc    6120
tatggaactc gccgcccgac tgggctggcg atgagcgaaa tgtagtgctt acgttgtccc    6180
gcatttggta cagcgcagta accggcaaaa tcgcgccgaa ggatgtcgct gccgactggg    6240
caatggagcg cctgccggcc cagtatcagc ccgtcatact tgaagctagg caggcttatc    6300
ttggacaaga agatcgcttg gcctcgcgcg cagatcagtt ggaagaattt gttcactacg    6360
tgaaaggcga gatcaccaaa gtagtcggca aataaagctc tagtggatct ccgtaccccc    6420
gggggatctg gctcgcggcg gacgcacgac gccggggcga gaccataggc gatctcctaa    6480
atcaatagta gctgtaacct cgaagcgttt cacttgtaac aacgattgag aattttttgtc    6540
ataaaattga aatacttggt tcgcattttt gtcatccgcg gtcagccgca attctgacga    6600
actgcccatt tagctggaga tgattgtaca tccttcacgt gaaaatttct caagcgctgt    6660
gaacaagggt tcagatttta gattgaaagg tgagccgttg aaacacgttc ttcttgtcga    6720
tgacgacgtc gctatgcggc atcttattat tgaataccct acgatccacg ccttcaaagt    6780
gaccgcggta gccgacagca cccagttcac aagagtactc tcttccgcga cggtcgatgt    6840
cgtggttgtt gatctaaatt taggtcgtga agatgggctc gagatcgttc gtaatctggc    6900
ggcaaagtct gatattccaa tcataattat cagtggcgac cgccttgagg agacggataa    6960
agttgttgca ctcgagctag gagcaagtga ttttatcgct aagccgttca gtatcagaga    7020
gtttctagca cgcattcggg ttgccttgcg cgtgcgcccc aacgttgtcc gctccaaaga    7080
```

```
ccgacggtct ttttgtttta ctgactggac acttaatctc aggcaacgtc gcttgatgtc    7140
cgaagctggc ggtgaggtga aacttacggc aggtgagttc aatcttctcc tcgcgttttt    7200
agagaaaccc cgcgacgttc tatcgcgcga gcaacttctc attgccagtc gagtacgcga    7260
cgaggaggtt tatgacagga gtatagatgt tctcattttg aggctgcgcc gcaaacttga    7320
ggcagatccg tcaagccctc aactgataaa aacagcaaga ggtgccggtt atttctttga    7380
cgcggacgtg caggtttcgc acgggggac gatggcagcc tgagccaatt cccagatccc     7440
cgaggaatcg gcgtgagcgg tcgcaaacca tccggcccgg tacaaatcgg cgcggcgctg    7500
ggtgatgacc tggtggagaa gttgaaggcc gcgcaggccg cccagcggca acgcatcgag    7560
gcagaagcac gccccggtga atcgtggcaa gcggccgctg atcgaatccg caaagaatcc    7620
cggcaaccgc cggcagccgg tgcgccgtcg attaggaagc cgcccaaggg cgacgagcaa    7680
ccagattttt tcgttccgat gctctatgac gtgggcaccc gcgatagtcg cagcatcatg    7740
gacgtggccg ttttccgtct gtcgaagcgt gaccgacgag ctggcgaggt gatccgctac    7800
gagcttccag acgggcacgt agaggtttcc gcagggccgg ccggcatggc cagtgtgtgg    7860
gattacgacc tggtactgat ggcggttttcc catctaaccg aatccatgaa ccgataccgg    7920
gaagggaagg gagacaagcc cggccgcgtg ttccgtccac acgttgcgga cgtactcaag    7980
ttctgccggc gagccgatgg cggaaagcag aaagacgacc tggtagaaac ctgcattcgg    8040
ttaaacacca cgcacgttgc catgcagcgt acgaagaagg ccaagaacgg ccgcctggtg    8100
acggtatccg agggtgaagc cttgattagc cgctacaaga tcgtaaagag cgaaaccggg    8160
cggccggagt acatcgagat cgagctagct gattggatgt accgcgagat cacagaaggc    8220
aagaacccgg acgtgctgac ggttcacccc gattactttt tgatcgatcc cggcatcggc    8280
cgttttctct accgcctggc acgccgcgcc gcaggcaagg cagaagccag atggttgttc    8340
aagacgatct acgaacgcag tggcagcgcc ggagagttca agaagttctg tttcaccgtg    8400
cgcaagctga tcgggtcaaa tgacctgccg gagtacgatt tgaaggagga ggcggggcag    8460
gctggcccga tcctagtcat gcgctaccgc aacctgatcg agggcgaagc atccgccggt    8520
tcctaatgta cggagcagat gctagggcaa attgccctag caggggaaaa aggtcgaaaa    8580
ggtctctttc ctgtggatag cacgtacatt gggaacccaa agccgtacat tgggaaccgg    8640
aacccgtaca ttgggaaccc aaagccgtac attgggaacc ggtcacacat gtaagtgact    8700
gatataaaag agaaaaaagg cgatttttcc gcctaaaact cttaaaact  tattaaaact    8760 cttaaaaccc gcctggcctg tgcataactg tctggccagc gcacagccga agagctgcaa    8820
aaagcgccta cccttcggtc gctgcgctcc ctacgcccg ccgcttcgcg tcggcctatc     8880
gcggccgctg gccgctcaaa atggctggc ctacggccag gcaatctacc agggcgcgga     8940
caagccgcgc cgtcgccact cgaccgccgg cgctgaggtc tgcctcgtga agaaggtgtt    9000
gctgactcat accaggcctg aatcgcccca tcatccagca gaaagtgag  ggagccacgg    9060 ttgatgagag ctttgttgta ggtggaccag ttggtgattt tgaacttttg ctttgccacg    9120
gaacggtctg cgttgtcggg aagatgcgtg atctgatcct tcaactcagc aaaagttcga    9180
tttattcaac aaagccgccg tcccgtcaag tcagcgtaat gctctgccag tgttacaacc    9240
aattaaccaa ttctgattag aaaaactcat cgagcatcaa atgaaactgc aatttattca    9300
tatcaggatt atcaatacca tattttgaa aaagccgttt ctgtaatgaa ggagaaaact     9360
caccgaggca gttccatagg atggcaagat cctggtatcg gtctgcgatt ccgactcgtc    9420
caacatcaat acaacctatt aatttcccct cgtcaaaaat aaggttatca agtgagaaat    9480
```

```
caccatgagt gacgactgaa tccggtgaga atggcaaaag ctctgcatta atgaatcggc   9540
caacgcgcgg ggagaggcgg tttgcgtatt gggcgctctt ccgcttcctc gctcactgac   9600
tcgctgcgct cggtcgttcg gctgcggcga gcggtatcag ctcactcaaa ggcggtaata   9660
cggttatcca cagaatcagg ggataacgca ggaaagaaca tgtgagcaaa aggccagcaa   9720
aaggccagga accgtaaaaa ggccgcgttg ctggcgtttt tccataggct ccgcccccct   9780
gacgagcatc acaaaaatcg acgctcaagt cagaggtggc gaaacccgac aggactataa   9840
agataccagg cgtttccccc tggaagctcc ctcgtgcgct ctcctgttcc gaccctgccg   9900
cttaccggat acctgtccgc ctttctccct tcgggaagcg tggcgctttc tcatagctca   9960
cgctgtaggt atctcagttc ggtgtaggtc gttcgctcca agctgggctg tgtgcacgaa  10020
ccccccgttc agcccgaccg ctgcgcctta tccggtaact atcgtcttga gtccaacccg  10080
gtaagacacg acttatcgcc actggcagca gccactggta acaggattag cagagcgagg  10140
tatgtaggcg gtgctacaga gttcttgaag tggtggccta actacggcta cactagaaga  10200
acagtatttg gtatctgcgc tctgctgaag ccagttacct tcggaaaaag agttggtagc  10260
tcttgatccg gcaaacaaac caccgctggt agcggtggtt tttttgtttg caagcagcag  10320
attacgcgca gaaaaaaagg atctcaagaa gatcctttga tcttttctac ggggtctgac  10380
gctcagtgga acgaaaactc acgttaaggg attttggtca tgagattatc aaaaaggatc  10440
ttcacctaga tccttttgat ccggaattaa ttcctgtggt tggcatgcac atacaaatgg  10500
acgaacggat aaacctttc acgccctttt aaatatccga ttattctaat aaacgctctt   10560
ttctcttag                                                         10569

<210> SEQ ID NO 20
<211> LENGTH: 10569
<212> TYPE: DNA
<213> ORGANISM: Artificial
<220> FEATURE:
<223> OTHER INFORMATION: pHiNK441
<220> FEATURE:
<221> NAME/KEY: pHiNK441
<222> LOCATION: (1)..(10569)
<220> FEATURE:
<221> NAME/KEY: terminator
<222> LOCATION: (233)..(527)
<223> OTHER INFORMATION: Nos
<220> FEATURE:
<221> NAME/KEY: Primer
<222> LOCATION: (522)..(549)
<223> OTHER INFORMATION: HiNK2618
<220> FEATURE:
<221> NAME/KEY: repeat_unit
<222> LOCATION: (528)..(810)
<223> OTHER INFORMATION: AGL20 cDNA in antisense orientation
<220> FEATURE:
<221> NAME/KEY: Primer
<222> LOCATION: (792)..(816)
<223> OTHER INFORMATION: HiNK792
<220> FEATURE:
<221> NAME/KEY: promoter
<222> LOCATION: (817)..(2169)
<223> OTHER INFORMATION: Arabidopsis Ubi3

<400> SEQUENCE: 20 gtttaccccgc caatatatcc tgtcaaacac tgatagttta aactgaaggc gggaaacgac     60
aatctgatca tgagcggaga attaagggag tcacgttatg accccgccg atgacgcggg      120 acaagccgtt ttacgtttgg aactgacaga accgcaacgc tgcaggaatt ggccgcagcg     180
gccatttaaa tcaattgggc gcgccgaatt cgagctcggt acccggggat cctctagatc     240
```

```
atgtttgaca gcttatcatc ggatctagta acatagatga caccgcgcgc gataatttat    300
cctagtttgc gcgctatatt ttgttttcta tcgcgtatta aatgtataat tgcgggactc    360
taatcataaa aacccatctc ataaataacg tcatgcatta catgttaatt attacatgct    420
taacgtaatt caacagaaat tagatgataa tcatcgcaag accggcaaca ggattcaatc    480
ttaagaaact ttattgccaa atgtttgaac gatctctgca ggtcgacaag aagttaaaaa    540
gtctcgaact ttctaaacgg aaattacttg gagatggtct agaggcatgt tccattgatg    600
agcttcaaga attagaaaaa caattagata aaagtctttc cagtatccga gcaagaaaga    660
atgcattgta caaagagcag attaataagt tgtatgaaga ggagaagcac ttaatcaaag    720
aaaatgtccg gttgaaagat aaggttctca attcttcacc agatctgcta cgtcgccaac    780
aacgagcaga tgatcaggag atcagcatgc ggatccaaag agagagtcgc gagagatttg    840
cagagatcgc tttaggcttt gggagagatt gaagagtcag aaaaagacga aaggatgaat    900
tattatcttc cacacgaagg tcttctttat atcgcaaacc aaaagcccaa aaccgtcttt    960
tctattaatg agaataaaat atctttagcc aaaacaaaaa aaggaagata tcagttgagg   1020
attattatca cgaaactaaa ggaaggaatc atatgatacg tgtcatattt tccaccgtgc   1080 gttttttaaaa gaccgactca agtagagaca tcctatggtg gtggttggat taggtcatcc   1140
attacatctg cttcactgac attttttctat ttttctttt gtatatactt ttcctcaaat   1200
aatttctttc ttttctatag aagaatttaa tcaataagga aaaagttcaa aaaagattct   1260
ttccattaag actatgtctt ggttaaccca acccattaag aataagcaat cataatatat   1320
atagagaata ctaatactat atatgagatt tttctttttaa tttcatgttg attatgatag   1380
tttatcttct tgatttaatt tatcaatact tggcataaaa gattctaatc tactctaata   1440
aagaaaagaa aaaaaagtat ctaccattga ctaattaaaa taaggaaact tatctaccaa   1500
atttgagtat tttttagaac aatcttttg gtttaattcc aaaactctaa acctaattgt   1560
tgggaaaaag gacctaattt ttaagaaaag ttaataatta gaagatctgt atgttttttt   1620
tttgatccaa gtttttattt cttttctctt tttttcatga taaaatctat gtttttttag   1680
tctacaatta aagtaattgt tattattttc tttatctttt tttgttgttg ttgttaattc   1740 ccttttttt tttttaacag caacttctta aaaaaaaaaa cagttgggcc ttgaatttat   1800
ttcaggcctg cgttattaag cccagataat aactcaaaac aaaaaaaatg ttgaaccgga   1860
ataaacccgc gagattaaat gccggttttc aggtaacata gaagaagaat atatgaggat   1920
tgaagaagta ttcaagaggc ggaacaattc acaagtccaa gagcttaaat ttctcctcac   1980
tcttctgcta cagactcgga actctttctc tttgctaaaa taagatgttc aggattttg   2040 ttgcccgaca attcatgtat ctcacactct ctctcttctc tgttcttact actctgttac   2100
attaccacca actcaagact ttcttccaca atggcgttta tgagacttgg ctccaaatcc   2160
ggacggatct ctagagtcga ccatggtgat cactgcaggc atgcaagctt cgtacgttaa   2220
ttaattcgaa tccggagcgg ccgcacgcgt gggcccgttt aaacctcgag agatctgcta   2280
gcatcgatgg taccgagctc gagactagct acaggccaaa ttcgctctta gccgtacaat   2340
attactcacc ggtgcgatgc cccccatcgt aggtgaaggt ggaaattaat gatccatctt   2400
gagaccacag gccacaaca gctaccagtt tcctcaaggg tccaccaaaa acgtaagcgc   2460
ttacgtacat ggtcgataag aaaaggcaat ttgtagatgt taacatccaa cgtcgctttc   2520
agggatcccg aattccaagc ttggaattcg ggatcctaca ggccaaattc gctcttagcc   2580
gtacaatatt actcaccggt gcgatgcccc ccatcgtagg tgaaggtgga aattaatgat   2640
```

```
ccatcttgag accacaggcc cacaacagct accagtttcc tcaagggtcc accaaaaacg    2700
taagcgctta cgtacatggt cgataagaaa aggcaatttg tagatgttaa catccaacgt    2760
cgctttcagg gatcccgaat tccaagcttg gaattcggga tcctacaggc caaattcgct    2820
cttagccgta caatattact caccggtgcg atcccccat cgtaggtgaa ggtggaaatt    2880
aatgatccat cttgagacca caggcccaca acagctacca gtttcctcaa gggtccacca    2940
aaaacgtaag cgcttacgta catggtcgat aagaaaaggc aatttgtaga tgttaacatc    3000
caacgtcgct ttcagggatc ccgaattcca agcttgggct gcaggtcaat cccattgctt    3060
ttgaagcagc tcaacattga tctcttctc gaggagatt tttcaaatca gtgcgcaaga    3120
cgtgacgtaa gtatccgagt cagtttttat ttttctacta atttggtcgt ttatttcggc    3180
gtgtaggaca tggcaaccgg gcctgaattt cgcgggtatt ctgtttctat tccaactttt    3240
tcttgatccg cagccattaa cgacttttga atagatacgc tgacacgcca agcctcgcta    3300
gtcaaaagtg taccaaacaa cgcttttacag caagaacgga atgcgcgtga cgctcgcggt    3360
gacgccattt cgccttttca gaaatggata aatagccttg cttcctatta tatcttccca    3420
aattaccaat acattacact agcatctgaa tttcataacc aatctcgata caccaaatcg    3480
agatctgcag ggatccccga tcatgcaaaa actcattaac tcagtgcaaa actatgcctg    3540
gggcagcaaa acggcgttga ctgaaacttta tggtatggaa aatccgtcca gccagccgat    3600
ggccgagctg tggatgggcg cacatccgaa aagcagttca cgagtgcaga atgccgccgg    3660
agatatcgtt tcactgcgtg atgtgattga gagtgataaa tcgactctgc tcggagaggc    3720
cgttgccaaa cgctttggcg aactgccttt cctgttcaaa gtattatgcg cagcacagcc    3780
actctccatt caggttcatc caaacaaaca caattctgaa atcggttttg ccaaagaaaa    3840
tgccgcaggt atcccgatgg atgccgccga gcgtaactat aaagatccta accacaagcc    3900
ggagctggtt tttgcgctga cgcctttcct tgcgatgaac gcgtttcgtg aatttttccga    3960 gattgtctcc ctactccagc cggtcgcagg tgcacatccg gcgattgctc acttttttaca    4020 acagcctgat gccgaacgtt taagcgaact gttcgccagc ctgttgaata tgcagggtga    4080
agaaaaatcc cgcgcgctgg cgattttaaa atcggccctc gatagccagc agggtgaacc    4140
gtggcaaacg attcgtttaa tttctgaatt ttacccggaa gacagcggtc tgttctcccc    4200
gctattgctg aatgtggtga aattgaaccc tggcgaagcg atgttcctgt tcgctgaaac    4260
accgcacgct tacctgcaag gcgtggcgct ggaagtgatg gcaaactccg ataacgtgct    4320
gcgtgcgggt ctgacgccta atacattga tattccggaa ctggttgcca atgtgaaatt    4380
cgaagccaaa ccggctaacc agttgttgac ccagccggtg aaacaaggtg cagaactgga    4440
cttcccgatt ccagtggatg attttgcctt ctcgctgcat gaccttagtg ataaagaaac    4500
caccattagc cagcagagtg ccgccatttt gttctgcgtc gaaggcgatg caacgttgtg    4560
gaaaggttct cagcagttac agcttaaacc gggtgaatca gcgtttattg ccgccaacga    4620
atcaccggtg actgtcaaag gccacggccg tttagcgcgt gtttacaaca agctgtaaga    4680
gcttactgaa aaaattaaca tctcttgcta agctgggagc tcgtcgacgg atcgaattcc    4740
tgcagatcgt tcaaacattt ggcaataaag tttcttaaga ttgaatcctg ttgccggtct    4800
tgcgatgatt atcatataat ttctgttgaa ttacgttaag catgtaataa ttaacatgta    4860
atgcatgacg ttatttatga gatgggtttt tatgattaga gtcccgcaat tatacattta    4920
atacgcgata gaaaacaaaa tatagcgcgc aaactaggat aaattatcgc gcgcggtgtc    4980
atctatgtta ctagatcggg aattgggtac cgaattcact ggccgtcgtt ttacaacgtc    5040
```

```
gtgactggga aaaccctggc gttacccaac ttaatcgcct tgcagcacat ccccctttcg   5100
ccagctggcg taatagcgaa gaggcccgca ccgatcgccc ttcccaacag ttgcgcagcc   5160
tgaatggcga atggcgggcg gccagcatgg ccgtatccgc aatgtgttat aagttgtct    5220
aagcgtcaat ttgtttacac cacaatatat cctgccacca gccagccaac agctccccga   5280
ccggcagctc ggcacaaaat caccactcga tacaggcagc ccatcagaat taattctcat   5340
gtttgacagc ttatcatcga ctgcacggtg caccaatgct tctggcgtca ggcagccatc   5400
ggaagctgtg gtatggctgt gcaggtcgta aatcactgca taattcgtgt cgctcaaggc   5460
gcactcccgt tctggataat gttttttgcg ccgacatcat aacggttctg gcaaatattc   5520
tgaaatgagc tgttgacaat taatcatccg gctcgtataa tgtgtggaat tgtgagcgga   5580
taacaatttc acacaggaaa cagaccatga gggaagcgtt gatcgccgaa gtatcgactc   5640
aactatcaga ggtagttggc gtcatcgagc gccatctcga ccgacgttg ctggccgtac    5700
atttgtacgg ctccgcagtg gatggcggcc tgaagccaca cagtgatatt gatttgctgg   5760
ttacggtgac cgtaaggctt gatgaaacaa cgcggcgagc tttgatcaac gaccttttgg   5820
aaacttcggc ttcccctgga gagagcgaga ttctccgcgc tgtagaagtc accattgttg   5880
tgcacgacga catcattccg tggcgttatc cagctaagcg cgaactgcaa tttggagaat   5940
ggcagcgcaa tgacattctt gcaggtatct tcgagccagc cacgatcgac attgatctgg   6000
ctatcttgct gacaaaagca agagaacata gcgttgcctt ggtaggtcca gcggcggagg   6060
aactctttga tccggttcct gaacaggatc tatttgaggc gctaaatgaa accttaacgc   6120
tatggaactc gccgcccgac tgggctggcg atgagcgaaa tgtagtgctt acgttgtccc   6180
gcatttggta cagcgcagta accggcaaaa tcgcgccgaa ggatgtcgct gccgactggg   6240
caatggagcg cctgccggcc cagtatcagc ccgtcatact tgaagctagg caggcttatc   6300
ttggacaaga agatcgcttg gcctcgcgcg cagatcagtt ggaagaattt gttcactacg   6360
tgaaaggcga gatcaccaaa gtagtcggca aataaagctc tagtggatct ccgtaccccc   6420
gggggatctg gctcgcggcg gacgcacgac gccggggcga gaccataggc gatctcctaa   6480
atcaatagta gctgtaacct cgaagcgttt cacttgtaac aacgattgag aattttttgtc   6540
ataaaattga atacttggt tcgcattttt gtcatccgcg gtcagccgca attctgacga    6600
actgcccatt tagctggaga tgattgtaca tccttcacgt gaaaatttct caagcgctgt   6660
gaacaagggt tcagattta gattgaaagg tgagccgttg aaacacgttc ttcttgtcga    6720
tgacgacgtc gctatgcggc atcttattat tgaatacctt acgatccacg ccttcaaagt   6780
gaccgcggta gccgacagca cccagttcac aagagtactc tcttccgcga cggtcgatgt   6840
cgtggttgtt gatctaaatt taggtcgtga agatgggctc gagatcgttc gtaatctggc   6900
ggcaaagtct gatattccaa tcataattat cagtggcgac cgccttgagg agacggataa   6960
agttgttgca ctcgagctag gagcaagtga ttttatcgct aagccgttca gtatcagaga   7020
gtttctagca cgcattcggg ttgccttgcg cgtgcgcccc aacgttgtcc gctccaaaga   7080
ccgacggtct ttttgtttta ctgactggac acttaatctc aggcaacgtc gcttgatgtc   7140
cgaagctggc ggtgaggtga aacttacggc aggtgagttc aatcttctcc tcgcgttttt   7200
agagaaaccc cgcgacgttc tatcgcgcga gcaacttctc attgccagtc gagtacgcga   7260
cgaggaggtt tatgacagga gtatagatgt tctcattttg aggctgcgcc gcaaacttga   7320
ggcagatccg tcaagccctc aactgataaa aacagcaaga ggtgccggtt atttctttga   7380
cgcggacgtg caggtttcgc acgggggac gatggcagcc tgagccaatt cccagatccc    7440
```

-continued

```
cgaggaatcg gcgtgagcgg tcgcaaacca tccggcccgg tacaaatcgg cgcggcgctg    7500
ggtgatgacc tggtggagaa gttgaaggcc gcgcaggccg cccagcggca acgcatcgag    7560
gcagaagcac gccccggtga atcgtggcaa gcggccgctg atcgaatccg caaagaatcc    7620
cggcaaccgc cggcagccgg tgcgccgtcg attaggaagc cgcccaaggg cgacgagcaa    7680
ccagattttt tcgttccgat gctctatgac gtgggcaccc gcgatagtcg cagcatcatg    7740
gacgtggccg ttttccgtct gtcgaagcgt gaccgacgag ctggcgaggt gatccgctac    7800
gagcttccag acgggcacgt agaggtttcc gcagggccgg ccggcatggc cagtgtgtgg    7860
gattacgacc tggtactgat ggcggttttcc catctaaccg aatccatgaa ccgataccgg    7920
gaagggaagg gagacaagcc cggccgcgtg ttccgtccac acgttgcgga cgtactcaag    7980
ttctgccggc gagccgatgg cggaaagcag aaagacgacc tggtagaaac ctgcattcgg    8040
ttaaacacca cgcacgttgc catgcagcgt acgaagaagg ccaagaacgg ccgcctggtg    8100
acggtatccg agggtgaagc cttgattagc cgctacaaga tcgtaaagag cgaaaccggg    8160
cggccggagt acatcgagat cgagctagct gattggatgt accgcgagat cacagaaggc    8220
aagaacccgg acgtgctgac ggttcacccc gattacttttt tgatcgatcc cggcatcggc    8280
cgttttctct accgcctggc acgccgcgcc gcaggcaagg cagaagccag atggttgttc    8340
aagacgatct acgaacgcag tggcagcgcc ggagagttca agaagttctg tttcaccgtg    8400
cgcaagctga tcgggtcaaa tgacctgccg gagtacgatt tgaaggagga ggcggggcag    8460
gctggcccga tcctagtcat gcgctaccgc aacctgatcg agggcgaagc atccgccggt    8520
tcctaatgta cggagcagat gctagggcaa attgccctag caggggaaaa aggtcgaaaa    8580
ggtctctttc ctgtggatag cacgtacatt gggaacccaa agccgtacat tgggaaccgg    8640
aacccgtaca ttgggaaccc aaagccgtac attgggaacc ggtcacacat gtaagtgact    8700
gatataaaag agaaaaaagg cgattttttcc gcctaaaact cttttaaaact tattaaaact    8760 cttaaaaccc gcctggcctg tgcataactg tctggccagc gcacagccga agagctgcaa    8820
aaagcgccta cccttcggtc gctgcgctcc ctacgccccg ccgcttcgcg tcggcctatc    8880
gcggccgctg gccgctcaaa aatggctggc ctacggccag gcaatctacc agggcgcgga    8940
caagccgcgc cgtcgccact cgaccgccgg cgctgaggtc tgcctcgtga agaaggtgtt    9000
gctgactcat accaggcctg aatcgcccca tcatccagcc agaaagtgag ggagccacgg    9060
ttgatgagag ctttgttgta ggtggaccag ttggtgattt tgaacttttg ctttgccacg    9120
gaacggtctg cgttgtcggg aagatgcgtg atctgatcct tcaactcagc aaaagttcga    9180
tttattcaac aaagccgccg tcccgtcaag tcagcgtaat gctctgccag tgttacaacc    9240
aattaaccaa ttctgattag aaaaactcat cgagcatcaa atgaaactgc aatttattca    9300
tatcaggatt atcaatacca tattttttgaa aaagccgttt ctgtaatgaa ggagaaaact    9360
caccgaggca gttccatagg atggcaagat cctggtatcg gtctgcgatt ccgactcgtc    9420
caacatcaat acaacctatt aatttcccct cgtcaaaaat aaggttatca agtgagaaat    9480
caccatgagt gacgactgaa tccggtgaga atggcaaaag ctctgcatta atgaatcggc    9540
caacgcgcgg ggagaggcgg tttgcgtatt gggcgctctt ccgcttcctc gctcactgac    9600
tcgctgcgct cggtcgttcg gctgcggcga gcggtatcag ctcactcaaa ggcggtaata    9660
cggttatcca cagaatcagg ggataacgca ggaaagaaca tgtgagcaaa aggccagcaa    9720
aaggccagga accgtaaaaa ggccgcgttg ctggcgtttt tccataggct ccgcccccct    9780
gacgagcatc acaaaaatcg acgctcaagt cagaggtggc gaaacccgac aggactataa    9840
```

```
agataccagg cgtttccccc tggaagctcc ctcgtgcgct ctcctgttcc gaccctgccg   9900
cttaccggat acctgtccgc ctttctccct tcgggaagcg tggcgctttc tcatagctca   9960
cgctgtaggt atctcagttc ggtgtaggtc gttcgctcca agctgggctg tgtgcacgaa  10020
ccccccgttc agcccgaccg ctgcgcctta tccgtaact  atcgtcttga gtccaacccg  10080
gtaagacacg acttatcgcc actggcagca gccactggta acaggattag cagagcgagg  10140
tatgtaggcg gtgctacaga gttcttgaag tggtggccta actacggcta cactagaaga  10200
acagtatttg gtatctgcgc tctgctgaag ccagttacct tcggaaaaag agttggtagc  10260
tcttgatccg gcaaacaaac caccgctggt agcggtggtt tttttgtttg caagcagcag  10320
attacgcgca gaaaaaaagg atctcaagaa gatcctttga tcttttctac ggggtctgac  10380
gctcagtgga acgaaaactc acgttaaggg attttggtca tgagattatc aaaaaggatc  10440
ttcacctaga tccttttgat ccggaattaa ttcctgtggt tggcatgcac atacaaatgg  10500
acgaacggat aaacctttc  acgcccttt  aaatatccga ttattctaat aaacgctctt  10560
ttctcttag                                                          10569
```

```
<210> SEQ ID NO 21
<211> LENGTH: 702
<212> TYPE: DNA
<213> ORGANISM: Beta vulgaris
<220> FEATURE:
<221> NAME/KEY: CDS
<222> LOCATION: (63)..(662)

<400> SEQUENCE: 21
aaaggacaga gagagtgaga gaaattgcag cgacgaagaa agagaaaggt atttggataa     60 gg atg gga aga agg aag ata gag atg aaa aga att gaa gat aaa agt      107
   Met Gly Arg Arg Lys Ile Glu Met Lys Arg Ile Glu Asp Lys Ser
   1               5                  10                  15 agt cgt caa gtt aca ttt tca aag cgg cgt tct ggt ctt atc aaa aaa    155
Ser Arg Gln Val Thr Phe Ser Lys Arg Arg Ser Gly Leu Ile Lys Lys
                20                  25                  30 gct cgc gaa ctc tct atc ctt tgt gat gtc gat gtt gct gtt ctt gtt    203
Ala Arg Glu Leu Ser Ile Leu Cys Asp Val Asp Val Ala Val Leu Val
            35                  40                  45 ttc tct aat cgt ggt cgt ctt tac gaa ttc gtc aat agt tct tct tct    251
Phe Ser Asn Arg Gly Arg Leu Tyr Glu Phe Val Asn Ser Ser Ser Ser
        50                  55                  60 tcc agt ttg tct cag att ctt aag cgc tat caa gat tcc act gca gca    299
Ser Ser Leu Ser Gln Ile Leu Lys Arg Tyr Gln Asp Ser Thr Ala Ala
65                  70                  75 gac ggg aaa gct tca ata gct gct gtt gaa aca gag agt tca cct tct    347
Asp Gly Lys Ala Ser Ile Ala Ala Val Glu Thr Glu Ser Ser Pro Ser
80                  85                  90                  95 agt tgt gca gaa gtc caa aca tgt ggt gag cta gta aaa tca gtt gaa    395
Ser Cys Ala Glu Val Gln Thr Cys Gly Glu Leu Val Lys Ser Val Glu
                100                 105                 110 agg tac cta gaa gga cca gag ctt gaa aat ctt agg ctt gag gac ttc    443
Arg Tyr Leu Glu Gly Pro Glu Leu Glu Asn Leu Arg Leu Glu Asp Phe
            115                 120                 125 atg agg ctg gag agg caa cta gct gat gcc ctt gta cag acc aga acc    491
Met Arg Leu Glu Arg Gln Leu Ala Asp Ala Leu Val Gln Thr Arg Thr
        130                 135                 140 cga aag gag aag ctg ttg aaa caa gag aat gaa cag ttg aag gat gag    539
Arg Lys Glu Lys Leu Leu Lys Gln Glu Asn Glu Gln Leu Lys Asp Glu
    145                 150                 155 gta gca aat ctg ata ggc att ccc aag agc cga aac cat aag gat tta    587
```

```
                Val Ala Asn Leu Ile Gly Ile Pro Lys Ser Arg Asn His Lys Asp Leu
                160                 165                 170                 175 ggg gtt aac aac ttg atg gag gtg gat gct gat aga caa tac tct cag            635
Gly Val Asn Asn Leu Met Glu Val Asp Ala Asp Arg Gln Tyr Ser Gln
                180                 185                 190 cca ctc aga aca ctt cca ctg ctg agg taactgctgt aagagtcggc                  682
Pro Leu Arg Thr Leu Pro Leu Leu Arg
            195                 200 attgagcagc attttgsmct                                                      702
```

<210> SEQ ID NO 22
<211> LENGTH: 200
<212> TYPE: PRT
<213> ORGANISM: Beta vulgaris

<400> SEQUENCE: 22

```
Met Gly Arg Arg Lys Ile Glu Met Lys Arg Ile Glu Asp Lys Ser Ser
1               5                   10                  15

Arg Gln Val Thr Phe Ser Lys Arg Ser Gly Leu Ile Lys Lys Ala
            20                  25                  30

Arg Glu Leu Ser Ile Leu Cys Asp Val Asp Val Ala Val Leu Val Phe
        35                  40                  45

Ser Asn Arg Gly Arg Leu Tyr Glu Phe Val Asn Ser Ser Ser Ser Ser
    50                  55                  60

Ser Leu Ser Gln Ile Leu Lys Arg Tyr Gln Asp Ser Thr Ala Ala Asp
65                  70                  75                  80

Gly Lys Ala Ser Ile Ala Ala Val Glu Thr Glu Ser Ser Pro Ser Ser
                85                  90                  95

Cys Ala Glu Val Gln Thr Cys Gly Glu Leu Val Lys Ser Val Glu Arg
            100                 105                 110

Tyr Leu Glu Gly Pro Glu Leu Glu Asn Leu Arg Leu Glu Asp Phe Met
        115                 120                 125

Arg Leu Glu Arg Gln Leu Ala Asp Ala Leu Val Gln Thr Arg Thr Arg
    130                 135                 140

Lys Glu Lys Leu Leu Lys Gln Glu Asn Glu Gln Leu Lys Asp Glu Val
145                 150                 155                 160

Ala Asn Leu Ile Gly Ile Pro Lys Ser Arg Asn His Lys Asp Leu Gly
                165                 170                 175

Val Asn Asn Leu Met Glu Val Asp Ala Asp Arg Gln Tyr Ser Gln Pro
            180                 185                 190

Leu Arg Thr Leu Pro Leu Leu Arg
        195                 200
```

<210> SEQ ID NO 23
<211> LENGTH: 747
<212> TYPE: DNA
<213> ORGANISM: Beta vulgaris
<220> FEATURE:
<221> NAME/KEY: CDS
<222> LOCATION: (63)..(707)

<400> SEQUENCE: 23

```
aaaggacaga gagagtgaga gaaattgcag cgacgaagaa agagaaaggt atttggataa          60 gg atg gga aga agg aag ata gag atg aaa aga att gaa gat aaa agt            107
   Met Gly Arg Arg Lys Ile Glu Met Lys Arg Ile Glu Asp Lys Ser
   1               5                   10                  15 agt cgt caa gtt aca ttt tca aag cgg cgt tct ggt ctt atc aaa aaa            155
Ser Arg Gln Val Thr Phe Ser Lys Arg Arg Ser Gly Leu Ile Lys Lys
                20                  25                  30
```

```
gct cgc gaa ctc tct atc ctt tgt gat gtc gat gtt gct gtt ctt gtt        203
Ala Arg Glu Leu Ser Ile Leu Cys Asp Val Asp Val Ala Val Leu Val
            35                  40                  45 ttc tct aat cgt ggt cgt ctt tac gaa ttc gtc aat agt tct tct tct        251
Phe Ser Asn Arg Gly Arg Leu Tyr Glu Phe Val Asn Ser Ser Ser Ser
    50                  55                  60 tcc agt ttg tct cag att ctt aag cgc tat caa gat tcc act gca gca        299
Ser Ser Leu Ser Gln Ile Leu Lys Arg Tyr Gln Asp Ser Thr Ala Ala
65                  70                  75 gac ggg aaa gct tca ata gct gct gtt gaa aca gag cag agt tca cct        347
Asp Gly Lys Ala Ser Ile Ala Ala Val Glu Thr Glu Gln Ser Ser Pro
80                  85                  90                  95 tct agt tgt gca gaa gtc caa aca tgt ggt gag cta gta aaa tca gtt        395
Ser Ser Cys Ala Glu Val Gln Thr Cys Gly Glu Leu Val Lys Ser Val
                100                 105                 110 gaa agg tac cta gaa gga cca gag ctt gaa aat ctt agg ctt gag gac        443
Glu Arg Tyr Leu Glu Gly Pro Glu Leu Glu Asn Leu Arg Leu Glu Asp
            115                 120                 125 ttc atg agg ctg gag agg caa cta gct gat gcc ctt gta cag acc aga        491
Phe Met Arg Leu Glu Arg Gln Leu Ala Asp Ala Leu Val Gln Thr Arg
        130                 135                 140 acc cga aag act caa ctt atg cta gaa tct atc gga aca cta agt gaa        539
Thr Arg Lys Thr Gln Leu Met Leu Glu Ser Ile Gly Thr Leu Ser Glu
145                 150                 155 cag gag aag ctg ttg aaa caa gag aat gaa cag ttg aag gat gag gta        587
Gln Glu Lys Leu Leu Lys Gln Glu Asn Glu Gln Leu Lys Asp Glu Val
160                 165                 170                 175 gca aat ctg ata ggc att ccc aag agc cga aac cat aag gat tta ggg        635
Ala Asn Leu Ile Gly Ile Pro Lys Ser Arg Asn His Lys Asp Leu Gly
                180                 185                 190 gtt aac aac ttg atg gag gtg gat gct gat aga caa tac tct cag cca        683
Val Asn Asn Leu Met Glu Val Asp Ala Asp Arg Gln Tyr Ser Gln Pro
            195                 200                 205 ctc aga aca ctt cca ctg ctg agg taactgctgt aagagtcggc attgagcagc      737
Leu Arg Thr Leu Pro Leu Leu Arg
        210                 215 attttgsmct                                                             747

<210> SEQ ID NO 24
<211> LENGTH: 215
<212> TYPE: PRT
<213> ORGANISM: Beta vulgaris

<400> SEQUENCE: 24

Met Gly Arg Arg Lys Ile Glu Met Lys Arg Ile Glu Asp Lys Ser Ser
1               5                   10                  15

Arg Gln Val Thr Phe Ser Lys Arg Arg Ser Gly Leu Ile Lys Lys Ala
            20                  25                  30

Arg Glu Leu Ser Ile Leu Cys Asp Val Asp Val Ala Val Leu Val Phe
        35                  40                  45

Ser Asn Arg Gly Arg Leu Tyr Glu Phe Val Asn Ser Ser Ser Ser Ser
    50                  55                  60

Ser Leu Ser Gln Ile Leu Lys Arg Tyr Gln Asp Ser Thr Ala Ala Asp
65                  70                  75                  80

Gly Lys Ala Ser Ile Ala Ala Val Glu Thr Glu Gln Ser Ser Pro Ser
                85                  90                  95

Ser Cys Ala Glu Val Gln Thr Cys Gly Glu Leu Val Lys Ser Val Glu
            100                 105                 110
```

```
Arg Tyr Leu Glu Gly Pro Glu Leu Glu Asn Leu Arg Leu Glu Asp Phe
    115                 120                 125

Met Arg Leu Glu Arg Gln Leu Ala Asp Ala Leu Val Gln Thr Arg Thr
130                 135                 140

Arg Lys Thr Gln Leu Met Leu Glu Ser Ile Gly Thr Leu Ser Glu Gln
145                 150                 155                 160

Glu Lys Leu Leu Lys Gln Glu Asn Glu Gln Leu Lys Asp Val Ala
                165                 170                 175

Asn Leu Ile Gly Ile Pro Lys Ser Arg Asn His Lys Asp Leu Gly Val
            180                 185                 190

Asn Asn Leu Met Glu Val Asp Ala Asp Arg Gln Tyr Ser Gln Pro Leu
        195                 200                 205

Arg Thr Leu Pro Leu Leu Arg
    210                 215

<210> SEQ ID NO 25
<211> LENGTH: 705
<212> TYPE: DNA
<213> ORGANISM: Beta vulgaris
<220> FEATURE:
<221> NAME/KEY: CDS
<222> LOCATION: (63)..(665)

<400> SEQUENCE: 25
aaaggacaga gagagtgaga gaaattgcag cgacgaagaa agagaaaggt atttggataa        60 gg atg gga aga agg aag ata gag atg aaa aga att gaa gat aaa agt       107
   Met Gly Arg Arg Lys Ile Glu Met Lys Arg Ile Glu Asp Lys Ser
   1               5                   10                  15 agt cgt caa gtt aca ttt tca aag cgg cgt tct ggt ctt atc aaa aaa       155
Ser Arg Gln Val Thr Phe Ser Lys Arg Arg Ser Gly Leu Ile Lys Lys
            20                  25                  30 gct cgc gaa ctc tct atc ctt tgt gat gtc gat gtt gct gtt ctt gtt       203
Ala Arg Glu Leu Ser Ile Leu Cys Asp Val Asp Val Ala Val Leu Val
        35                  40                  45 ttc tct aat cgt ggt cgt ctt tac gaa ttc gtc aat agt tct tct tct       251
Phe Ser Asn Arg Gly Arg Leu Tyr Glu Phe Val Asn Ser Ser Ser Ser
    50                  55                  60 tcc agt ttg tct cag att ctt aag cgc tat caa gat tcc act gca gca       299
Ser Ser Leu Ser Gln Ile Leu Lys Arg Tyr Gln Asp Ser Thr Ala Ala
65                  70                  75 gac ggg aaa gct tca ata gct gct gtt gaa aca gag cag agt tca cct       347
Asp Gly Lys Ala Ser Ile Ala Ala Val Glu Thr Glu Gln Ser Ser Pro
80                  85                  90                  95 tct agt tgt gca gaa gtc caa aca tgt ggt gag cta gta aaa tca gtt       395
Ser Ser Cys Ala Glu Val Gln Thr Cys Gly Glu Leu Val Lys Ser Val
                100                 105                 110 gaa agg tac cta gaa gga cca gag ctt gaa aat ctt agg ctt gag gac       443
Glu Arg Tyr Leu Glu Gly Pro Glu Leu Glu Asn Leu Arg Leu Glu Asp
            115                 120                 125 ttc atg agg ctg gag agg caa cta gct gat gcc ctt gta cag acc aga       491
Phe Met Arg Leu Glu Arg Gln Leu Ala Asp Ala Leu Val Gln Thr Arg
        130                 135                 140 acc cga aag gag aag ctg ttg aaa caa gag aat gaa cag ttg aag gat       539
Thr Arg Lys Glu Lys Leu Leu Lys Gln Glu Asn Glu Gln Leu Lys Asp
    145                 150                 155 gag gta gca aat ctg ata ggc att ccc aag agc cga aac cat aag gat       587
Glu Val Ala Asn Leu Ile Gly Ile Pro Lys Ser Arg Asn His Lys Asp
160                 165                 170                 175 tta ggg gtt aac aac ttg atg gag gtg gat gct gat aga caa tac tct       635
Leu Gly Val Asn Asn Leu Met Glu Val Asp Ala Asp Arg Gln Tyr Ser
```

```
                180               185               190
cag cca ctc aga aca ctt cca ctg ctg agg taactgctgt aagagtcggc      685
Gln Pro Leu Arg Thr Leu Pro Leu Leu Arg
        195                 200 attgagcagc attttgsmct                                              705

<210> SEQ ID NO 26
<211> LENGTH: 201
<212> TYPE: PRT
<213> ORGANISM: Beta vulgaris

<400> SEQUENCE: 26

Met Gly Arg Arg Lys Ile Glu Met Lys Arg Ile Glu Asp Lys Ser Ser
1               5                   10                  15

Arg Gln Val Thr Phe Ser Lys Arg Ser Gly Leu Ile Lys Lys Ala
            20                  25                  30

Arg Glu Leu Ser Ile Leu Cys Asp Val Asp Val Ala Val Leu Val Phe
        35                  40                  45

Ser Asn Arg Gly Arg Leu Tyr Glu Phe Val Asn Ser Ser Ser Ser
    50                  55                  60

Ser Leu Ser Gln Ile Leu Lys Arg Tyr Gln Asp Ser Thr Ala Ala Asp
65                  70                  75                  80

Gly Lys Ala Ser Ile Ala Ala Val Glu Thr Glu Gln Ser Ser Pro Ser
                85                  90                  95

Ser Cys Ala Glu Val Gln Thr Cys Gly Glu Leu Val Lys Ser Val Glu
            100                 105                 110

Arg Tyr Leu Glu Gly Pro Glu Leu Glu Asn Leu Arg Leu Glu Asp Phe
        115                 120                 125

Met Arg Leu Glu Arg Gln Leu Ala Asp Ala Leu Val Gln Thr Arg Thr
    130                 135                 140

Arg Lys Glu Lys Leu Leu Lys Gln Glu Asn Glu Gln Leu Lys Asp Glu
145                 150                 155                 160

Val Ala Asn Leu Ile Gly Ile Pro Lys Ser Arg Asn His Lys Asp Leu
                165                 170                 175

Gly Val Asn Asn Leu Met Glu Val Asp Ala Asp Arg Gln Tyr Ser Gln
            180                 185                 190

Pro Leu Arg Thr Leu Pro Leu Leu Arg
        195                 200

<210> SEQ ID NO 27
<211> LENGTH: 702
<212> TYPE: DNA
<213> ORGANISM: Beta vulgaris

<400> SEQUENCE: 27
aaaggacaga gagagtgaga gaaattgcag cgacgaagaa agagaaaggt atttggataa      60
ggatgggaag aaggaagata gagatgaaaa gaattgaaga taaaagtagt cgtcaagtta    120
cattttcaaa gcggcgttct ggtcttatca aaaaagctcg cgaactctct atcctttgtg    180
atgtcgatgt tgctgttctt gttttctcta atcgtggtcg tctttacgaa ttcgtcaata    240
gttcttcttc ttccagtttg tctcagattc ttaagcgcta tcagattcc actgcagcag    300 acgggaaagc ttcaatagct gctgttaaaa cagagagttc accttctagt gtgcagaag    360 tccaaacatg tggtgagcta gtaaaatcag ttgaaaggta cctagaagga ccagagcttg    420
aaaatcttag gcttgaggac ttcatgaggc tggagaggca actagctgat gcccttgtac    480
agaccagaac ccgaaaggag aagctgttga acaagagaa tgaacagttg aaggatgagg    540
```

```
tagcaaatct dataggcatt cccaagagcc gaaaccataa ggatttaggg gttaacaact        600
tgatggaggt ggatgctgat agacaatact ctcagccact cagaacactt ccactgctga        660
ggtaactgct gtaagagtcg gcattgagca gcattttgsm ct                           702
```

<210> SEQ ID NO 28
<211> LENGTH: 682
<212> TYPE: DNA
<213> ORGANISM: Beta vulgaris

<400> SEQUENCE: 28

```
aaaggacaga gagagtgaga gaaattgcag cgacgaagaa agagaaaggt atttggataa         60
ggatgggaag aaggaagata gagatgaaaa gaattgaaga taaaagtagt cgtcaagtta        120
cattttcaaa gcggcgttct ggtcttatca aaaaagctcg cgaactctct atcctttgtg        180
atgtcgatgt tgctgttctt gttttctcta atcgtggtcg tctttacgaa ttcgtcaata        240
gttcttcttc ttccagtttg tctcagattc ttaagcgcta tcaagattcc actgcagcag        300
acgggaaagc ttcaatagct gctgttgaaa cagagcagag ttcaccttct agttgtgcag        360
aagtccaaac atgtggtgag ctagtaaaat cagttgaaag gtacctagaa ggaccagagc        420
ttgaaaatct taggcttgag gacttcatga ggctggagag gcaactagct gatgcccttg        480
tacagaccag aacccgaaag actcaactta tgctagaatc tatcggaaca ctaagtgaac        540
aggagaagct gttgaaacaa gagaatgaac agttgaagga tgaggtagca aatctgatag        600
gcattcccaa gagccgaaac cataaggatt taggggttaa caacttgatg gaggtggatg        660
ctgatagaca atactctcag cc                                                682
```

<210> SEQ ID NO 29
<211> LENGTH: 640
<212> TYPE: DNA
<213> ORGANISM: Beta vulgaris

<400> SEQUENCE: 29

```
aaaggacaga gagagtgaga gaaattgcag cgacgaagaa agagaaaggt atttggataa         60
ggatgggaag aaggaagata gagatgaaaa gaattgaaga taaaagtagt cgtcaagtta        120
cattttcaaa gcggcgttct ggtcttatca aaaaagctcg cgaactctct atcctttgtg        180
atgtcgatgt tgctgttctt gttttctcta atcgtggtcg tctttacgaa ttcgtcaata        240
gttcttcttc ttccagtttg tctcagattc ttaagcgcta tcaagattcc actgcagcag        300
acgggaaagc ttcaatagct gctgttgaaa cagagcagag ttcaccttct agttgtgcag        360
aagtccaaac atgtggtgag ctagtaaaat cagttgaaag gtacctagaa ggaccagagc        420
ttgaaaatct taggcttgag gacttcatga ggctggagag gcaactagct gatgcccttg        480
tacagaccag aacccgaaag gagaagctgt tgaaacaaga gaatgaacag ttgaaggatg        540
aggtagcaaa tctgataggc attcccaaga gccgaaacca taaggattta ggggttaaca        600
acttgatgga ggtggatgct gatagacaat actctcagcc                              640
```

<210> SEQ ID NO 30
<211> LENGTH: 26
<212> TYPE: DNA
<213> ORGANISM: Artificial sequence
<220> FEATURE:
<223> OTHER INFORMATION: HiNK5277
<220> FEATURE:
<221> NAME/KEY: misc_feature
<222> LOCATION: (3)..(3)
<223> OTHER INFORMATION: n is a, c, g, or t

```
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: y is t/u or c
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: r is g or a
<220> FEATURE:
<221> NAME/KEY: misc_feature
<222> LOCATION: (24)..(24)
<223> OTHER INFORMATION: r is g or a

<400> SEQUENCE: 30
cgncgnaayg gnctnctnaa raargc                                          26

<210> SEQ ID NO 31
<211> LENGTH: 32
<212> TYPE: DNA
<213> ORGANISM: Artificial sequence
<220> FEATURE:
<223> OTHER INFORMATION: HiNK5279
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: y is t/u or c
<220> FEATURE:
<221> NAME/KEY: misc_feature
<222> LOCATION: (9)..(9)
<223> OTHER INFORMATION: r is g or a
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: y is t/u or c
<220> FEATURE:
<221> NAME/KEY: misc_feature
<222> LOCATION: (27)..(27)
<223> OTHER INFORMATION: y is t/u or c
<220> FEATURE:
<221> NAME/KEY: misc_feature
<222> LOCATION: (30)..(30)
<223> OTHER INFORMATION: n is a, c, g, or t
```

```
<400> SEQUENCE: 31
gcntaygarc tntcngtnct ntgygaygcn ga                              32

<210> SEQ ID NO 32
<211> LENGTH: 21
<212> TYPE: DNA
<213> ORGANISM: Artificial sequence
<220> FEATURE:
<223> OTHER INFORMATION: AGL20 A

<400> SEQUENCE: 32
gtctcgaact ttctaaacgg a                                          21

<210> SEQ ID NO 33
<211> LENGTH: 20
<212> TYPE: DNA
<213> ORGANISM: Artificial sequence
<220> FEATURE:
<223> OTHER INFORMATION: AGL20 B

<400> SEQUENCE: 33
gatcatctgc tcgttgttgg                                            20

<210> SEQ ID NO 34
<211> LENGTH: 22
<212> TYPE: DNA
<213> ORGANISM: Artificial sequence
<220> FEATURE:
<223> OTHER INFORMATION: HiNK023

<400> SEQUENCE: 34
cgcaagaccg gcaacaggat tc                                         22

<210> SEQ ID NO 35
<211> LENGTH: 23
<212> TYPE: DNA
<213> ORGANISM: Artificial sequence
<220> FEATURE:
<223> OTHER INFORMATION: gapCex5/6F

<400> SEQUENCE: 35
gctgctgctc acttgaaggg tgg                                        23

<210> SEQ ID NO 36
<211> LENGTH: 20
<212> TYPE: DNA
<213> ORGANISM: Artificial sequence
<220> FEATURE:
<223> OTHER INFORMATION: gapCex8R

<400> SEQUENCE: 36
cttccacctc tccagtcctt                                            20

<210> SEQ ID NO 37
<211> LENGTH: 25
<212> TYPE: DNA
<213> ORGANISM: Artificial sequence
<220> FEATURE:
<223> OTHER INFORMATION: HiNK 819

<400> SEQUENCE: 37
tctgcgtgga gtgaaaagta aagtg                                      25
```